(12) United States Patent
Bour et al.

(10) Patent No.: US 11,034,646 B2
(45) Date of Patent: Jun. 15, 2021

(54) METHOD FOR THE SYNTHESIS OF UNSYMMETRICAL TERTIARY AMINES

(71) Applicants: UNIVERSITE PARIS-SACLAY, Saint-Aubin (FR); CENTRE NATIONAL DE LA RECHERCHE SCIENTIFIQUE, Paris (FR)

(72) Inventors: Christophe Bour, Saint-Cheron (FR); Marie Jenny Jacqueline Vayer, Flavy le Martel (FR); Vincent Gandon, Arpajon (FR)

(73) Assignees: UNIVERSITE PARIS-SACLAY, Saint-Aubin (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/651,728

(22) PCT Filed: Sep. 28, 2018

(86) PCT No.: PCT/FR2018/052396
§ 371 (c)(1),
(2) Date: Mar. 27, 2020

(87) PCT Pub. No.: WO2019/063952
PCT Pub. Date: Apr. 4, 2019

(65) Prior Publication Data
US 2020/0255369 A1    Aug. 13, 2020

(30) Foreign Application Priority Data
Sep. 29, 2017   (FR) ...................... 1759117

(51) Int. Cl.
| | | |
|---|---|---|
| *C07C 209/16* | (2006.01) |
| *B01J 31/22* | (2006.01) |
| *C07C 213/02* | (2006.01) |
| *C07D 307/52* | (2006.01) |
| *C07D 317/58* | (2006.01) |
| *C07C 211/21* | (2006.01) |
| *C07C 211/27* | (2006.01) |
| *C07C 211/29* | (2006.01) |
| *C07C 217/58* | (2006.01) |
| *C07C 217/84* | (2006.01) |

(52) U.S. Cl.
CPC ......... *C07C 209/16* (2013.01); *B01J 31/2295* (2013.01); *C07C 213/02* (2013.01); *C07D 307/52* (2013.01); *C07D 317/58* (2013.01); *B01J 2531/842* (2013.01); *B01J 2540/10* (2013.01); *C07C 211/21* (2013.01); *C07C 211/27* (2013.01); *C07C 211/29* (2013.01); *C07C 217/58* (2013.01); *C07C 217/84* (2013.01)

(58) Field of Classification Search
CPC ... C07C 209/16; C07C 213/02; B01J 31/2295
See application file for complete search history.

(56) References Cited

PUBLICATIONS

Moulin et al. Chemistry A European Journal, (2013), 19(52), p. 17881-17890.*
Imine in Wikipedia, downloaded Aug. 27, 2020.*
International Search Report, dated Mar. 1, 2019, from corresponding PCT application No. PCT/FR2018/052396.
French Search Report, dated Jun. 12, 2018, from corresponding French application No. FR 1759117.
Campos et al.; Methanol Dehydrogenation by Iridium N-Heterocyclic Carbene Complexes; Inorganic Chemistry; Jun. 15, 2015; pp. 5079-5084; vol. 54, No. 11.
Moulin et al.; Bifunctional (Cyclopentadienone)lron-Tricarbonyl Complexes: Synthesis, Computational Studies and Application in Reductive Amination; Chemistry—A European Journal; Nov. 15, 2013; pp. 17881-17890; vol. 19, No. 52.

* cited by examiner

*Primary Examiner* — Yong L Chu
(74) *Attorney, Agent, or Firm* — Nixon & Vanderhye

(57) ABSTRACT

Disclosed is a new method for the synthesis of unsymmetrical tertiary amines using alcohol and an imine, and to new tertiary amines.

9 Claims, No Drawings

METHOD FOR THE SYNTHESIS OF UNSYMMETRICAL TERTIARY AMINES

The present invention relates to a new method for the synthesis of unsymmetrical tertiary amines using an alcohol and an imine, as well as novel tertiary amines.

The development of simple reactions for C—N bond formation is an important challenge to chemists. Substituted amines have widespread applications in the synthesis of drugs, dyes, detergents, perfumes, pharmaceuticals, emulsifiers, crop protection agents, etc.

Among the various strategies for the synthesis of amines, the development of direct amination reactions of alcohols for the rapid generation of secondary or tertiary amines, from simple and readily available starting materials, is at the forefront of fine chemical synthesis and involves a high potential for industrial development.

Among these methods, the direct amination of alcohols by borrowing of hydrogen (or hydrogen transfer) has been recognized as one of the most practical for the industrial production of trisubstituted alkylamines. This atom efficient reaction and the wide availability of the alcohols, combined with the fact that water is the only byproduct of these reactions, responding to general principles of green chemistry, are the reasons for its widespread use.

This amination has been performed for the first time with late transition metals of the second and third periods, which were rapidly followed by much more elaborate complexes (Ru, Rh, Ir, Os). The current trend is to replace these noble elements with less expensive and more abundant transition metals of the first period. In this respect, significant improvements have recently been made using manganese, iron or cobalt catalysts. However, there is still a significant need for more active catalysts working in milder conditions, which allow greater functional tolerance of the substrate and improve the selectivity and TON (Turn-Over Number).

If we wish to access the synthesis of tertiary amines by this strategy, we can only have access to trisubstituted amines with 1 or 2 different groups. However, there are no direct amination methods to access tertiary amines having 3 different substituents. The direct conversion of primary amines, via the synthesis of imines, to tertiary amines bearing three different substituents is thus unknown to date.

One of the aims of the invention is the provision of a new method for the synthesis of tertiary trisubstituted asymmetric amines, simple to implement, fast and applicable to a wide variety of substrates.

One of the other aims of the invention is the possibility of using a catalyst derived from an abundant and inexpensive metal allowing to work under mild conditions.

One of the other aims of the invention is the ability to access the synthesis of a wide variety of tertiary amines, in a simple manner.

This new method has the advantages of being simple to implement, fast, applicable to a wide variety of substrates, using a catalyst derived from an abundant and inexpensive metal and allowing to work under mild conditions.

The present invention relates to the use of an alcohol, in particular primary or secondary, with the exception of methanol, and of an imine in the implementation of a method of preparation of tertiary amines.

Within the meaning of the invention, the expression "primary alcohol" refers to a compound of formula R—O—H wherein the carbon atom carrying the hydroxyl group also carries two hydrogen atoms.

Within the meaning of the invention, the expression "secondary alcohol" refers to a compound of formula R—O—H wherein the carbon atom carrying the hydroxyl group carries a single hydrogen atom.

Within the meaning of the invention, the expression "tertiary amine" refers to a compound of formula N—$R_3$ in which R is not a hydrogen atom.

The present invention also relates to the use of an alcohol, in particular primary or secondary, with the exception of methanol, and of an imine in the implementation of a method of preparation of tertiary amines, in particular carrying three different substituents.

According to another embodiment, the invention relates to the use of an alcohol, in particular primary or secondary, with the exception of methanol, and of an imine in the implementation of a method of preparation of tertiary amines, wherein the prepared tertiary amine carries three all different substituents with respect to each other and different from a hydrogen atom.

According to another embodiment, the invention relates to the use of an alcohol of formula (C)

$$R_4OH \qquad (C)$$

wherein $R_4$ represents a $C_2$ to $C_{10}$ alkyl, or a $C_3$ to $C_{10}$ cycloalkyl and of an imine of formula (D)

(D)

wherein $R_1$ and $R_2$ represent a hydrogen, aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
in the implementation of a method of preparation of tertiary amines of formula (E)

(E)

wherein $R_1$, $R_2$, $R_3$, $R_4$ are as defined above.

Within the meaning of the invention, the expression "$C_1$ to $C_{10}$" refers to an acyclic saturated carbon chain, linear or branched, comprising 1 to 10 carbon atoms. Examples of $C_1$ to $C_{10}$ alkyls include methyl, ethyl, propyl, butyl, pentyl, hexyl or heptyl.

Within the meaning of the invention, the expression "$C_2$ to $C_{10}$" refers to an acyclic saturated carbon chain, linear or branched, comprising 2 to 10 carbon atoms. Examples of $C_2$ to $C_{10}$ alkyls include ethyl, propyl, butyl, pentyl, hexyl or heptyl. The definition of propyl, butyl, pentyl, hexyl or heptyl includes all possible isomers. For example, the term butyl comprises n-butyl, iso-butyl, sec-butyl and tert-butyl. The alkyl may be substituted at different positions with one or more functional groups such as halogen, alkoxyl, amino, nitro, cyano, trifluoromethyl or carboxylic ester.

Within the meaning of the present invention, the expression "$C_3$ to $C_{10}$ cycloalkyl" denotes a mono-, bi- or tri-cycle, saturated or partially saturated, comprising from 3 to 10 carbon atoms.

Within the meaning of the invention, the expression "$C_1$ to $C_{10}$ carbonyl derivative" denotes a compound comprising 1 to 10 carbon atoms and having a double bond between a carbon atom and an oxygen atom.

Within the meaning of the invention, the expression "$C_3$ to $C_{10}$ formate" means a compound of formula HCOOR comprising 3 to 10 carbon atoms.

According to the above embodiment, the invention relates to the use of an alcohol of formula (C), that can be a primary or secondary alcohol, and of an imine of formula (D), that can be an aldimine or a ketimine.

Within the meaning of the invention, the expression "aldimine" denotes an imine of formula (D)

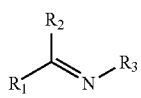
(D)

wherein $R_2$ represents a hydrogen.

Within the meaning of the invention, the expression "ketimine" denotes an imine of formula (D)

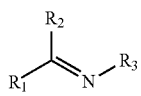
(D)

wherein $R_2$ is not a hydrogen atom.

According to a particular embodiment, the invention relates to the use of a primary alcohol of formula (C)

$R_4OH$ (C)

wherein $R_4$ represents a $C_2$ to $C_{10}$ alkyl
and of an imine of formula (D)

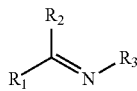
(D)

wherein $R_1$ represents an aryl, allyl, $C_1$ to $C_{10}$ alkyl, or $C_3$ to $C_{10}$ cycloalkyl,
$R_2$ represents a hydrogen,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
in the implementation of a method of preparation of tertiary amines of formula (E)

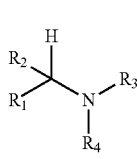
(E)

wherein $R_1$, $R_2$, $R_3$, $R_4$ are as defined above.

According to another particular embodiment, the invention relates to the use of a primary alcohol of formula (C)

$R_4OH$ (C)

wherein $R_4$ represents a $C_2$ to $C_{10}$ alkyl,
and of an imine of formula (D)

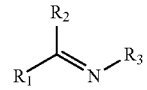
(D)

wherein $R_1$ and $R_2$ represent an aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
in the implementation of a method of preparation of tertiary amines of formula (E)

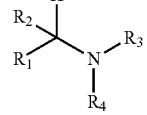
(E)

wherein $R_1$, $R_2$, $R_3$, $R_4$ are as defined above.

According to another particular embodiment, the invention relates to the use of a secondary alcohol of formula (C)

$R_4OH$ (C)

wherein $R_4$ represents a $C_2$ to $C_{10}$ alkyl, or a $C_3$ to $C_{10}$ cycloalkyl, and of an imine of formula (D)

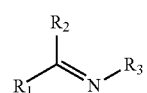
(D)

wherein $R_1$ represents an aryl, allyl, $C_1$ to $C_{10}$ alkyl, or $C_3$ to $C_{10}$ cycloalkyl,
$R_2$ represents a hydrogen,
$R_3$ represents an aryl, allyl, $C_1$ to $C_{10}$ alkyl, $C_3$ to $C_{10}$ cycloalkyl, a $C_1$ to $C_{10}$ carbonyl derivative of, or a $C_3$ to $C_{10}$ formate,
in the implementation of a method of preparation of tertiary amines of formula (E)

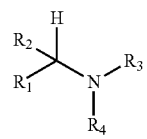
(E)

wherein $R_1$, $R_2$, $R_3$, $R_4$ are as defined above.

According to another particular embodiment, the invention relates to the use of a secondary alcohol of formula (C)

(C)

wherein $R_4$ represents a $C_2$ to $C_{10}$ alkyl, or a $C_3$ to $C_{10}$ cycloalkyl, and of an imine of formula (D)

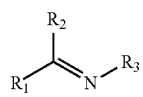

(D)

wherein $R_1$ and $R_2$ represent an aryl, allyl, $C_1$ to $C_{10}$ alkyl, or $C_3$ to $C_{10}$ cycloalkyl, $R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, in the implementation of a method of preparation of tertiary amines of formula (E)

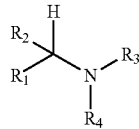

(E)

wherein $R_1$, $R_2$, $R_3$, $R_4$ are as defined above.

According to another embodiment, the invention relates to the use of an alcohol, in particular primary or secondary, and of an imine in the implementation of a method of preparation of tertiary amines wherein the preparation of tertiary amines is performed in the presence of a catalyst comprising an iron(0) complex.

Within the meaning of the invention, the expression "catalyst" refers to a compound that allows, increases the speed of a chemical reaction.

Within the meaning of the invention, the expression "iron(0) complex" denotes a chemical structure in which an iron atom in the oxidation state 0 is linked to multiple ligands.

Indeed, the inventors were able to go beyond the conventional reactivity of alcohols using iron(0) catalysts which are able to catalyze the addition of primary alcohols and secondary on imines by N-alkylation. This method has no literature precedent and allows for the synthesis of amines trisubstituted with three different groups, that are inaccessible by conventional methods.

According to another embodiment, the invention relates to the use of an alcohol, in particular primary or secondary, and of an imine in the implementation of a method of preparation of tertiary amines, wherein the preparation of tertiary amines is performed in the presence of a catalyst comprising an iron(0) complex chosen from the following formulas:

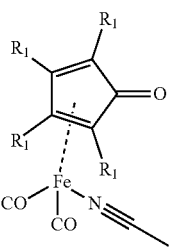

$R_1$ = Ph, tBu

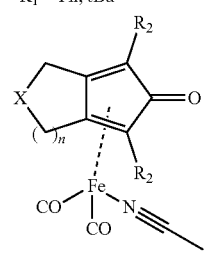

X = $CH_2$, $C(CO_2Me)$, O, NTs, $SO_2Ph$,
$R_2$ = Ph, TMS, TBDMS, TIPS
n = 0, 1, 2, 3 in which

Ts=tosyl

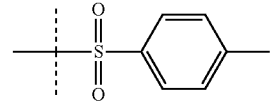

TMS=trimethylsilyl

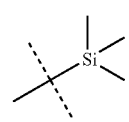

TBDMS=tert-butyldimethylsilyl

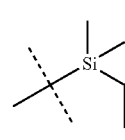

TIPS=triisopropylsilyl

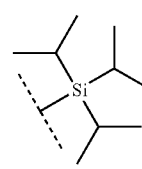

and preferably being of the following formula (B):

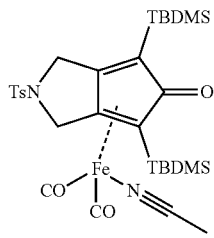
(B)

in which
TBDMS=tert-butyldimethylsilyl

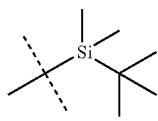

Ts=tosyl

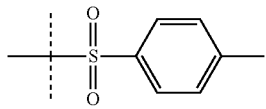

The catalyst used is either the catalyst of formula (B) prepared prior to the preparation of the tertiary amines, or the catalyst formed in situ during this preparation via the addition of trimethylamine oxide to the complex of formula (A):

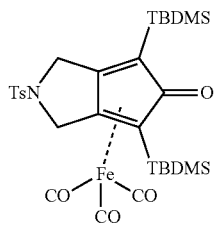
(A)

This cyclopentadienone tricarbonyl-type catalyst of formula (A) must first be activated by the addition of an additive, trimethylamine oxide, to remove a CO type ligand, which makes it active but this step requires the use of a glove box. The inventors have demonstrated that the preformed catalyst of formula (B), through stabilization of an acetonitrile ligand, could be manipulated in ambient air, and was equally active in catalysis.

According to another embodiment, the invention relates to the use of an alcohol, in particular primary or secondary, and of an imine, in the implementation of a method of preparation of tertiary amines wherein the preparation of tertiary amines is performed in the presence of a catalyst comprising an iron(0) complex chosen from the following formulas:

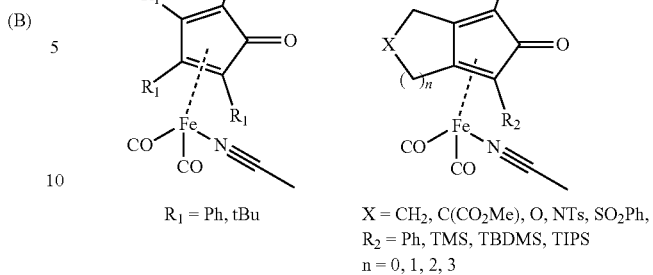

$R_1$ = Ph, tBu

X = $CH_2$, $C(CO_2Me)$, O, NTs, $SO_2Ph$,
$R_2$ = Ph, TMS, TBDMS, TIPS
n = 0, 1, 2, 3 in which
Ts=tosyl

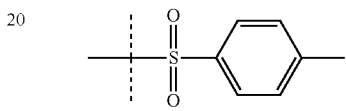

TMS=trimethylsilyl

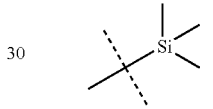

TBDMS=tert-butyldimethylsilyl

TIPS=triisopropylsilyl

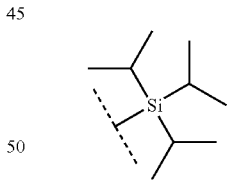

and preferably being of the following formula (B):

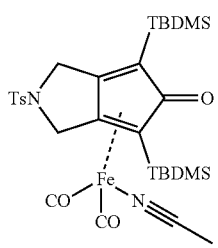
(B)

in which
TBDMS=tert-butyldimethylsilyl

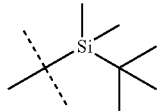

Ts=tosyl

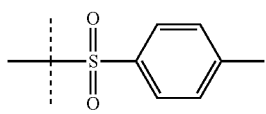

Other examples of catalysts that can be used are the following:

CHBO477

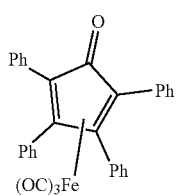

CHBO519

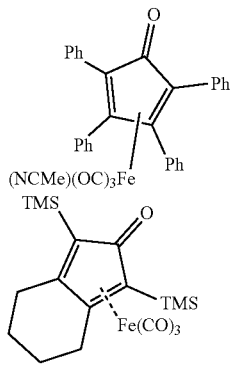

Knölker

CHBO466

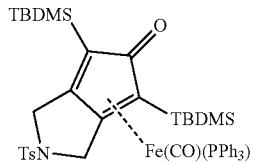

According to another embodiment, the invention relates to the use of an alcohol, in particular primary or secondary, and of an imine in the implementation of a method of preparation of tertiary amines wherein the preparation of amino tertiary is performed in the presence of a catalyst comprising an iron(0) complex, wherein the catalyst used is either the complex of formula (B) formed prior to the preparation of tertiary amines, or the catalyst formed in situ during said preparation of tertiary amines by adding trimethylamine oxide to the complex of formula (A):

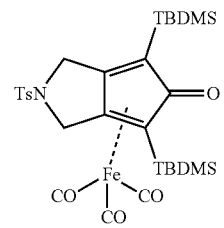

(A)

According to a particular embodiment, the invention relates to the use of an alcohol, in particular primary or secondary, and of an imine in the implementation of a tertiary amine preparation method, wherein the alcohol of formula (C) is chosen from ethanol, n-propanol, isopropanol, n-butanol, sec-butanol, isobutanol, amyl alcohol, isopentanol, neopentyl alcohol, methyl-n-propylcarbinol, hexan-1-ol, heptan-1-ol, octan-1-ol, nonan-1-ol, decan-1-ol, ethylene glycol.

According to another particular embodiment, the aforementioned imine is chosen from

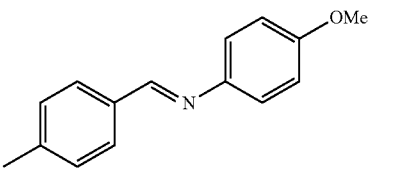

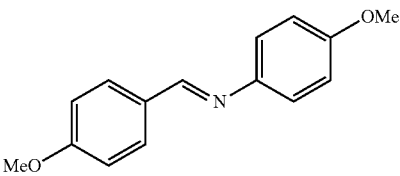

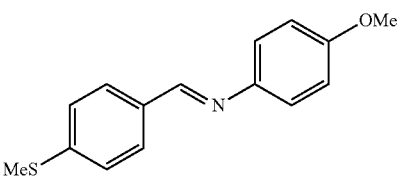

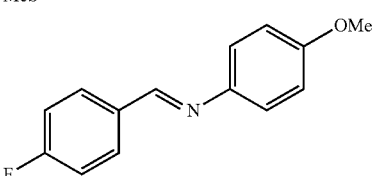

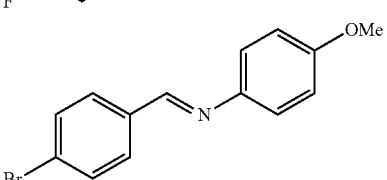

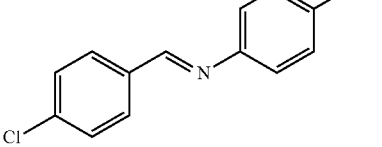

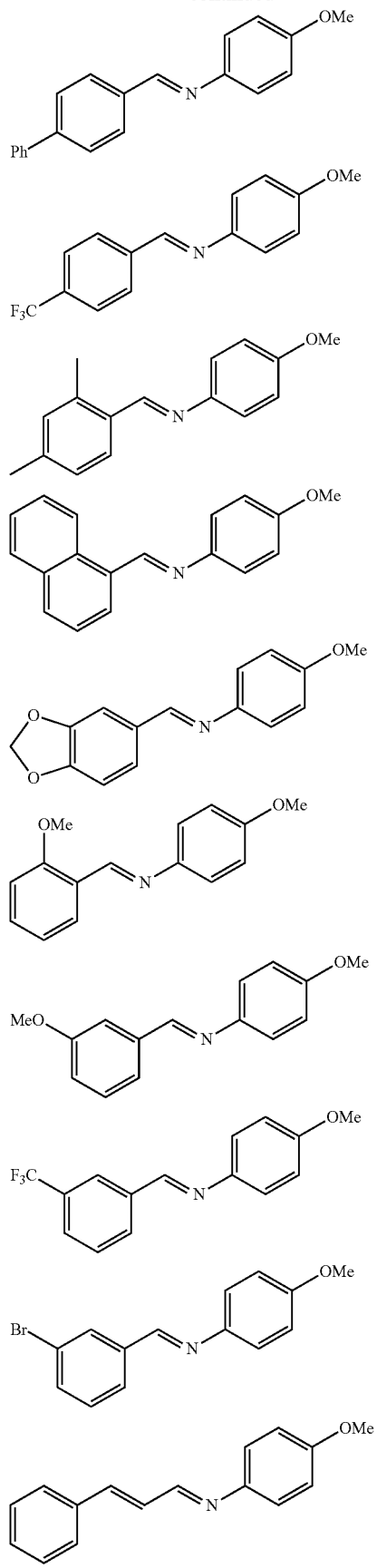
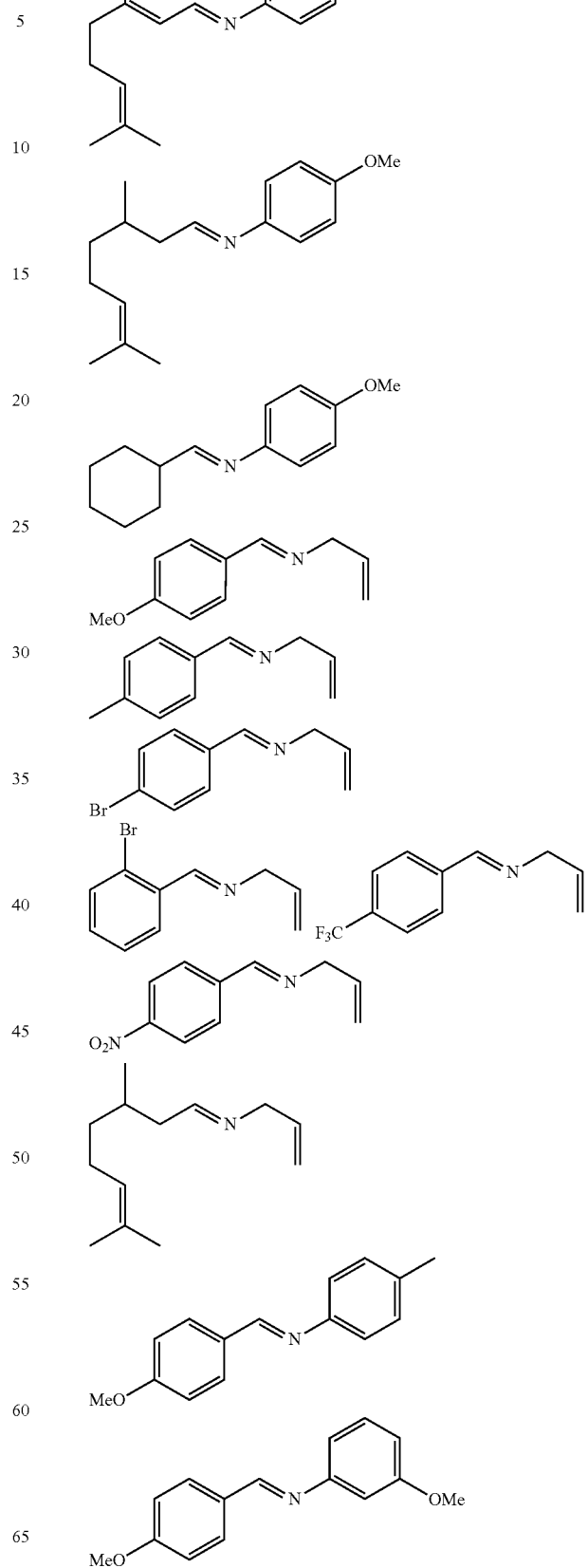

-continued

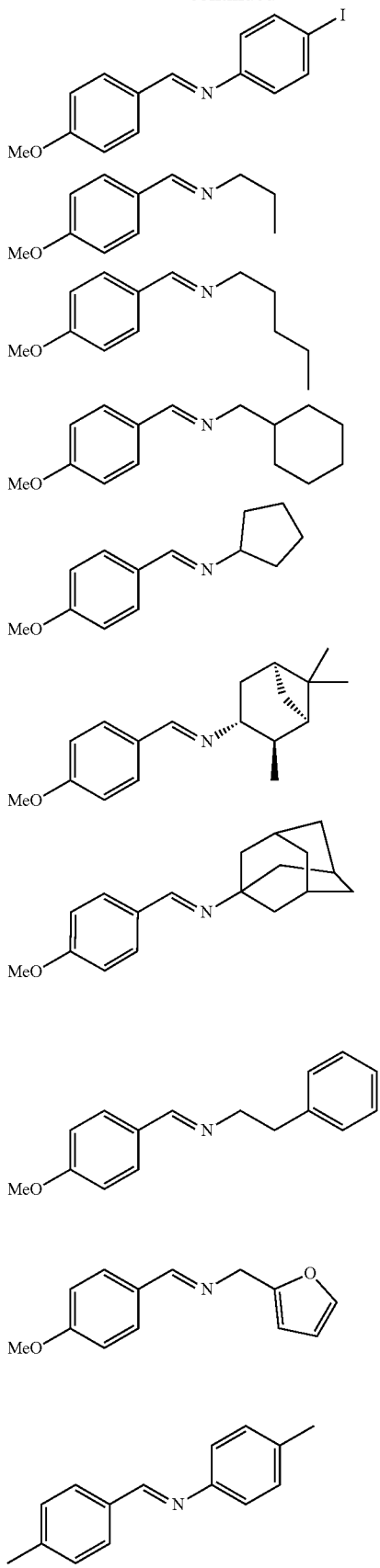

The present invention also concerns a method of preparation of tertiary amines of formula (E)

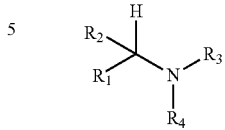
(E)

wherein $R_1$ and $R_2$ represent a hydrogen, aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
$R_4$ represents a $C_2$ to $C_{10}$ alkyl, or $C_3$ to $C_{10}$ cycloalkyl, said tertiary amine of formula (E) carrying in particular three different substituents, different from a hydrogen atom;
comprising a step of alkylation of an alcohol of formula (C)

$$R_4OH \quad (C)$$

wherein $R_4$ is as defined above,
on an imine of formula (D)

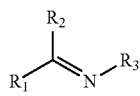
(D)

wherein $R_1$, $R_2$ and $R_3$ are as defined above,
to obtain the compound of formula (E) as defined above.

According to the above embodiment, the invention relates to a method of preparation of tertiary amines of formula (E) comprising a step of alkylation of an alcohol of formula (C) that can be a primary or secondary alcohol on an imine of formula (D) that can be an aldimine or a ketimine.

According to a particular embodiment, the present invention relates to a method of preparation of tertiary amines of formula (E)

(E)

wherein $R_1$ represents an aryl, allyl, $C_1$ to $C_{10}$ alkyl or $C_3$ to $C_{10}$ cycloalkyl,
$R_2$ represents a hydrogen,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
$R_4$ represents a $C_2$ to $C_{10}$ alkyl;
comprising a step of alkylation of an alcohol of formula (C)

$$R_4OH \quad (C)$$

wherein $R_4$ is as defined above,
on an imine of formula (D)

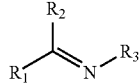
(D)

wherein $R_1$, $R_2$ and $R_3$ are as defined above,
to obtain the compound of formula (E) as defined above.

According to another particular embodiment, the present invention relates to a method of preparation of tertiary amines of formula (E)

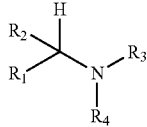
(E)

wherein $R_1$ and $R_2$ represent an aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
$R_4$ represents a $C_2$ to $C_{10}$ alkyl;
comprising a step of alkylation of an alcohol of formula (C)

$R_4OH$ (C)

wherein $R_4$ is as defined above,
on an imine of formula (D)

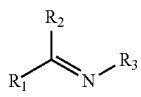
(D)

wherein $R_1$, $R_2$ and $R_3$ are as defined above,
to obtain the compound of formula (E) as defined above.

According to a particular embodiment, the present invention relates to a method of preparation of tertiary amines of formula (E)

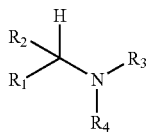
(E)

wherein $R_1$ is an aryl, allyl, $C_1$ to $C_{10}$ alkyl, or $C_3$ to $C_{10}$ cycloalkyl,
$R_2$ represents a hydrogen,
$R_3$ represents an aryl, allyl, $C_1$ to $C_{10}$ alkyl, $C_3$ to $C_{10}$ cycloalkyl, a $C_1$ to $C_{10}$ carbonyl derivative or a $C_3$ to $C_{10}$ formate,
$R_4$ represents a $C_2$ to $C_{10}$ alkyl or a $C_3$ to $C_{10}$ cycloalkyl;
comprising a step of alkylation of an alcohol of formula (C)

$R_4OH$ (C)

wherein $R_4$ is as defined above,
on an imine of formula (D)

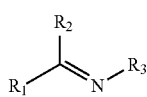
(D)

wherein $R_1$, $R_2$ and $R_3$ are as defined above,
to obtain the compound of formula (E) as defined above.

According to a particular embodiment, the present invention relates to a method of preparation of tertiary amines of formula (E)

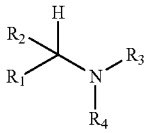
(E)

wherein $R_1$ and $R_2$ represent an aryl, allyl, $C_1$ to $C_{10}$ alkyl, or $C_3$ to $C_{10}$ cycloalkyl,
$R_3$ represents an aryl, allyl, alkyl $C_1$ to $C_{10}$ alkyl, $C_3$ to $C_{10}$ cycloalkyl, a $C_1$ to $C_{10}$ carbonyl derivative, or a $C_3$ to $C_{10}$ formate,
$R_4$ represents a $C_2$ to $C_{10}$ alkyl, or $C_3$ to $C_{10}$ cycloalkyl;
comprising a step of alkylation of an alcohol of formula (C)

$R_4OH$ (C)

wherein $R_4$ is as defined above,
on an imine of formula (D)

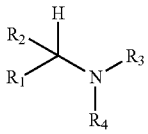
(D)

wherein $R_1$, $R_2$ and $R_3$ are as defined above,
to obtain the compound of formula (E) as defined above.

According to another embodiment, the invention relates to a method of preparation of tertiary amines of formula (E)

wherein the tertiary amine of formula (E) carries three different substituents and wherein $R_1$ and $R_2$ represent a hydrogen, aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
$R_4$ is $C_2$ to $C_{10}$ alkyl, or $C_3$ to $C_{10}$ cycloalkyl.

According to another embodiment, the invention relates to a method of preparation of tertiary amines of formula (E), wherein the alcohol of formula (C) is chosen from ethanol, n-propanol, isopropanol, n-butanol, sec-butanol, isobutanol, amyl alcohol, isopentanol, neopentyl alcohol, methyl-n-propylcarbinol, hexan-1-ol, heptan-1-ol, octan-1-ol, nonan-1-ol, decan-1-ol, ethylene glycol.

According to another embodiment, the invention relates to a method of preparation of tertiary amines of formula (E), wherein the step of alkylation is catalyzed by an iron(0) complex.

According to another embodiment, the invention relates to a method of preparation of tertiary amines of formula (E), wherein the step of alkylation is catalyzed, in particular by an iron(0) complex, chosen from the following formulas:

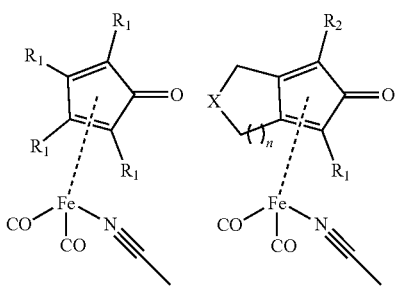

R₁ = Ph, tBu

X = CH₂, C(CO₂Me), O, NTs, SO₂Ph,
R₂ = Ph, TMS, TBDMS, TIPS
n = 0, 1, 2, 3 wherein
Ts=tosyl

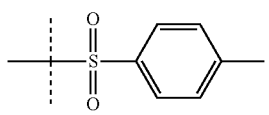

TMS=trimethylsilyl

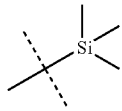

TBDMS=tert-butyldimethylsilyl

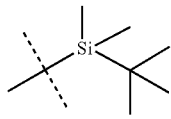

TIPS=triisopropylsilyl

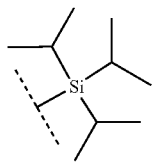

and preferably being of the following formula (B):

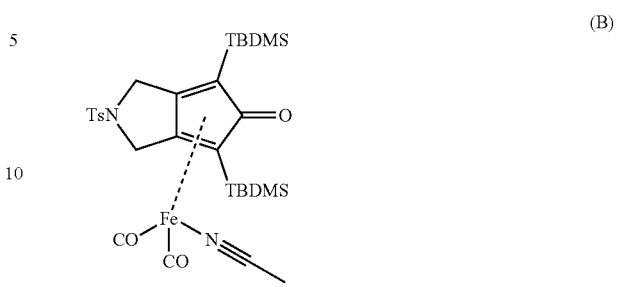

(B)

in which
TBDMS=tert-butyldimethylsilyl

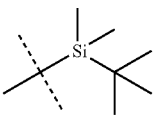

Ts=tosyl

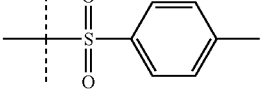

According to another embodiment, the invention relates to a method of preparation of tertiary amines of formula (E), wherein the step of alkylation is catalyzed by the complex of formula (B).

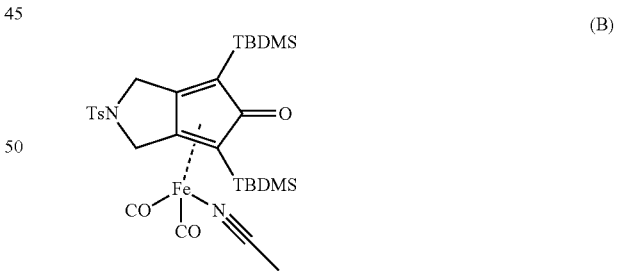

(B)

According to another embodiment, the invention relates to a method of preparation of tertiary amines of formula (E), wherein the step of alkylation is catalyzed either by the complex of formula (B) formed prior to the preparation of tertiary amines, or the catalyst formed in situ during said preparation of tertiary amines by adding trimethylamine oxide to the complex of formula (A).

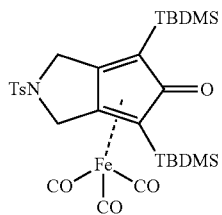
(A)

According to another embodiment, the invention relates to a method of preparation of tertiary amines of formula (E), wherein the step of alkylation is performed at a temperature of 80° C. to 130° C., and preferably at 110° C.

According to another embodiment, the invention relates to a method of preparation of tertiary amines of formula (E), wherein the step of alkylation is performed in an organic solvent.

Said organic solvent can be:
- a single solvent chosen from ethanol, ethylene glycol, tetrahydrofuran, dichloroethane, toluene, methoxycyclopentane, diethyl ether.
- a mixture of solvents chosen from the above mentioned solvents or
- the alcohol of formula (C) used as a solvent and as a reactant in the method of preparation of tertiary amines of formula (E).

According to another embodiment, the invention relates to a method of preparation of tertiary amines of formula (E), wherein the step of alkylation is performed in ethanol or ethylene glycol used as solvent and as reactant, or in a mixture of solvents composed in particular of THF and of ethanol or of ethylene glycol, ethanol or ethylene glycol being used as a solvent and reagent.

The use of ethanol, and more generally the alcohol of formula (C), both as a solvent and as a reactant in this method of preparation of tertiary amines of formula (E) makes it possible to carry out the reaction in the presence of a large excess of one of the two reactants, which promotes the reaction. The second interest is to avoid the use of another solvent, which makes the reaction more simple to implement and more economic.

According to another embodiment, the invention relates to a method of preparation of tertiary amines of formula (E), wherein the primary alcohol of formula (C), in particular ethanol or ethylene glycol is also used as solvent for the step of alkylation, in particular in a number of equivalents higher than 10 equivalents, and preferably 85 equivalents.

The use of a solvent composed of primary alcohol of formula (C) in admixture with another solvent in the method of preparation of tertiary amines of formula (E) can be carried out according to the solvent/primary alcohol (C) proportions ranging from 1/1 to 13/1.

When the primary alcohol of formula (C) is used both as solvent and as reactant in the method of preparation of tertiary amines of formula (E), at least 10 equivalents of primary alcohol of formula (C) are used and preferably 85 equivalents.

When an organic solvent other than the primary alcohol of formula (C) is used, 3 equivalents of primary alcohol of formula (C) are used as reagent.

According to another embodiment, the invention relates to a method of preparation of tertiary amines of formula (E), wherein the concentration of imine of formula (D) is comprised from 0.05 M to 0.4 M, in particular of 0.1 M, 0.2 M, 0.3 M, 0.4 M, and is preferably 0.2 M.

According to another embodiment, the invention relates to a method of preparation of tertiary amines formula (E), wherein the amount of catalyst is comprised from 1 to 20 mol %, in particular from 1 to 5 mol %, 5 to 10 mol %, 10 to 15 mol %, 15 to 20 mol %, and is preferably 5 mol %, relative to the molar amount of imine.

According to a preferred embodiment, the invention relates to a method of preparation of tertiary amines of formula (E), wherein the step of alkylation is performed at a temperature of 110° C. for 24 hours in ethanol with a concentration of imine of formula (D) of 0.2 M and a quantity of catalyst of 5 mol %.

According to another embodiment, the invention relates to a method of preparation of tertiary amines of formula (E), wherein the imine of formula (D) is either formed prior to the preparation of the tertiary amines, or is formed in situ during said preparation of tertiary amines by a method comprising contacting an aldehyde or ketone of formula (F)

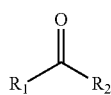
(F)

wherein $R_1$, $R_2$ represents a hydrogen, aryl, allyl, $C_1$ to $C_{10}$ alkyl, or $C_3$ to $C_{10}$ cycloalkyl, and an amine of formula (G)

$R_3-NH_2$ (G)

wherein $R_3$ represents an aryl, allyl, $C_1$ to $C_{10}$ alkyl, $C_3$ to $C_{10}$ cycloalkyl, a $C_1$ to $C_{10}$ carbonyl derivative or a $C_3$ to $C_{10}$ formate.

According to the above embodiment, the invention relates to a method of preparation of tertiary amines of formula (E), comprising a step of preparing tertiary amines of formula (E) comprising a step of alkylation of an alcohol of formula (C) to an imine of formula (D) wherein the imine of formula (D) is either formed prior to the preparation of tertiary amines, or formed in situ during said preparation of tertiary amines by a method comprising contacting an aldehyde or a ketone of formula (F), and an amine of formula (G), the step of alkylation being performed in the presence of a catalyst of formula (B) either preformed or formed in situ in a first step prior to the step of alkylation.

According to another embodiment, the invention relates to a method of preparation of tertiary amines of formula (E), comprising a step of preparing tertiary amines of formula (E)

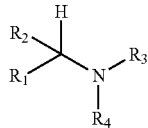
(E)

wherein $R_1$ and $R_2$ represent a hydrogen, aryl, allyl, $C_1$ to $C_{10}$ alkyl, or $C_3$ to $C_{10}$ cycloalkyl, $R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, $R_4$ represents a $C_2$ to $C_{10}$ alkyl, or a $C_3$ to $C_{10}$ cycloalkyl; comprising a step of alkylation of an alcohol of formula (C)

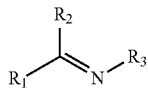  (C)

wherein $R_4$ is as defined above,
on an imine of formula (D)

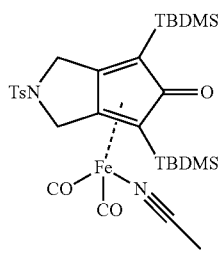  (D)

wherein $R_1$, $R_2$ and $R_3$ are as defined above,
in the presence of a catalyst of formula (B)

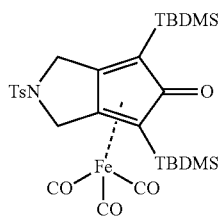  (B)

to obtain the compound of formula (E) as defined above, or
comprising a first step of preparing of the catalyst
comprising a step of adding trimethylamine oxide on the complex of formula (A)

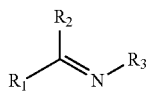  (A)

and a second step of alkylation of an alcohol of formula (C)

R$_4$OH  (C)

wherein $R_4$ represents a $C_2$ to $C_{10}$ alkyl, or a $C_3$ to $C_{10}$ cycloalkyl, on an imine of formula (D)

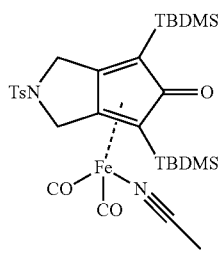  (D)

wherein $R_1$ and $R_2$ represent a hydrogen, aryl, allyl, $C_1$ to $C_{10}$ alkyl or a $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, in the presence of a catalyst of formula (B) prepared during the preceding step and as defined above, to obtain the compound of formula (E)

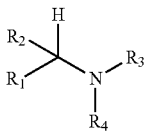  (E)

wherein $R_1$, $R_2$, $R_3$ and $R_4$ are as defined above, or
comprising a first step of preparing imines of formula (D)

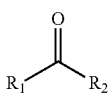  (D)

wherein $R_1$ and $R_2$ represent a hydrogen, aryl, allyl, $C_1$ to $C_{10}$ alkyl, or cycloalkyl $C_3$ to $C_{10}$,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
comprising a step of contacting with an aldehyde or a ketone of formula (F)

  (F)

wherein $R_1$ and $R_2$ are as defined above,
and an amine of formula (G)

  $R_3-NH_2$  (G)

wherein $R_3$ is as defined above,
to obtain the imine of formula (D) as defined above;
and a second step of alkylation of an alcohol of formula (C)

R$_4$OH  (C)

wherein $R_4$ represents a $C_2$ to $C_{10}$ alkyl, or a $C_3$ to $C_{10}$ cycloalkyl,
on an imine of formula (D) prepared in the preceding step and as defined above, in the presence of a catalyst of formula (B)

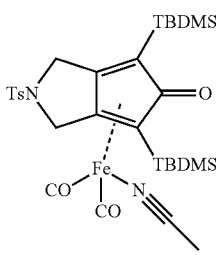  (B)

to obtain the compound of formula (E)

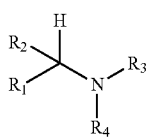
(E)

wherein $R_1$, $R_2$, $R_3$ and $R_4$ are as defined above, or
comprising a prior step of preparing of imines of formula (D)

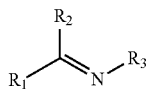
(D)

wherein $R_1$ and $R_2$ represent a hydrogen, aryl, allyl, $C_1$ to $C_{10}$ alkyl, or $C_3$ to $C_{10}$ cycloalkyl, $R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, comprising a step of contacting an aldehyde or ketone of formula (F)

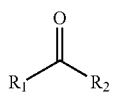
(F)

wherein $R_1$ and $R_2$ are as defined above,
and an amine of formula (G)

$R_3$—$NH_2$ (G)

wherein $R_3$ is as defined above,
to obtain the imine of formula (D) as defined above;
a prior step of preparing the catalyst
comprising a step of adding trimethylamine oxide to the complex of formula (A):

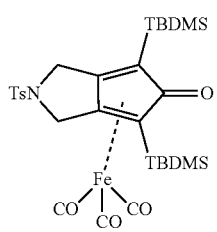
(A)

said two prior steps may occur in any order,
and a step of alkylation of an alcohol of formula (C)

$R_4OH$ (C)

wherein $R_4$ represents a $C_2$ to $C_{10}$ alkyl, or a $C_3$ to $C_{10}$ cycloalkyl, on an imine of formula (D) prepared in the previous step

(D)

wherein $R_1$, $R_2$ and $R_3$ are as defined above,
in the presence of catalyst of formula (B) prepared in the preceding step and as above,
to obtain the compound of formula (E)

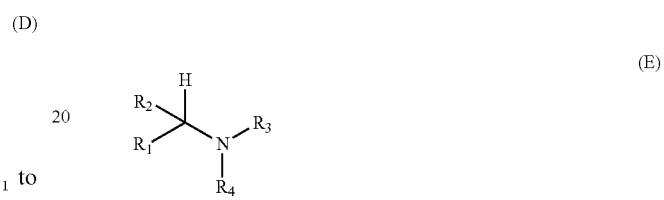
(E)

wherein $R_1$, $R_2$, $R_3$ and $R_4$ are as defined above.

According to another embodiment, the invention relates to a method of preparation of tertiary amines of formula (E), comprising a step of preparing tertiary amines of formula (E)

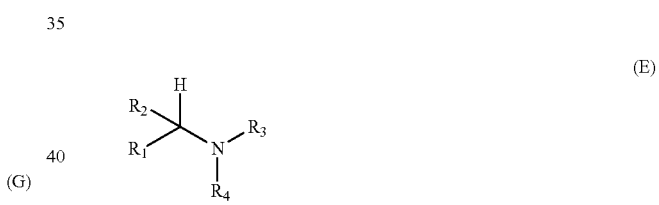
(E)

wherein $R_1$ and $R_2$ represent a hydrogen, aryl, allyl, $C_1$ to $C_{10}$ alkyl, or $C_3$ to $C_{10}$ cycloalkyl, $R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, $R_4$ represents a $C_2$ to $C_{10}$ alkyl or $C_3$ to $C_{10}$ cycloalkyl;
comprising a step of alkylation of an alcohol of formula (C)

$R_4OH$ (C)

wherein $R_4$ is as defined above,
on an imine of formula (D)

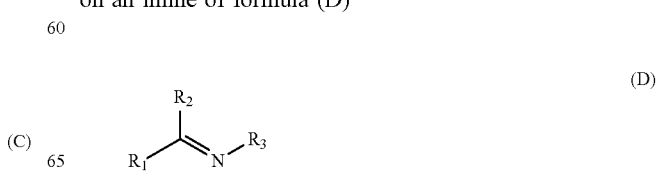
(D)

wherein $R_1$, $R_2$ and $R_3$ are as defined above,
in the presence of a catalyst of formula (B)

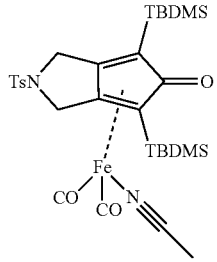
(B)

to obtain the compound of formula (E) as defined above.

According to a preferred embodiment, the invention relates to a method of preparation of tertiary amines of formula (E), comprising a step of alkylation of a primary alcohol of formula (C) to an imine of formula (D) in the presence of a catalyst of formula (B) formed prior to the preparation of the tertiary amines.

According to a preferred embodiment, the invention relates to a method of preparation of tertiary amines of formula (E), comprising a step of alkylation of a primary alcohol of formula (C) to an imine of formula (D) in the presence of a catalyst of formula (B), the imine of formula (D) and the catalyst of formula (B) being formed prior to the preparation of the tertiary amines.

According to another embodiment, the invention relates to a method of preparation of tertiary amines of formula (E), comprising a first step of preparing of the catalyst, comprising a step of addition of trimethyl amine oxide to the complex of formula (A)

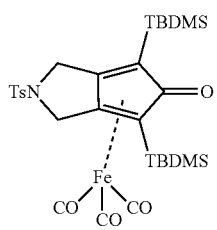
(A)

and a second step of alkylation of an alcohol of formula (C)

$R_4OH$ (C)

wherein $R_4$ represents a $C_2$ to $C_{10}$ alkyl, or a $C_3$ to $C_{10}$ cycloalkyl,
on an imine of formula (D)

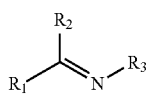
(D)

wherein $R_1$ and $R_2$ represent a hydrogen, aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, in the presence of a catalyst of formula (B) prepared in the preceding step and as defined above, to obtain the compound of formula (E)

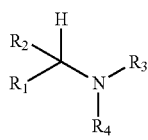
(E)

wherein $R_1$, $R_2$, $R_3$ and $R_4$ are as defined above.

According to another embodiment, the invention relates to a method of preparation of tertiary amines of formula (E), comprising a first step of preparing imines of formula (D)

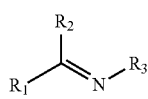
(D)

wherein $R_1$ and $R_2$ represent a hydrogen, aryl, allyl, $C_1$ to $C_{10}$ alkyl, or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
comprising a step of contacting with an aldehyde or a ketone of formula (F)

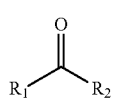
(F)

wherein $R_1$ and $R_2$ are as defined above,
and an amine of formula (G)

$R_3-NH_2$ (G)

wherein $R_3$ is as defined above,
to obtain the imine of formula (D) as defined above;
and a second step of alkylation of an alcohol of formula (C)

$R_4OH$ (C)

wherein $R_4$ represents a $C_2$ to $C_{10}$ alkyl, or a $C_3$ to $C_{10}$ cycloalkyl,
on an imine of formula (D) prepared in the preceding step and as defined above, in the presence of a catalyst of formula (B)

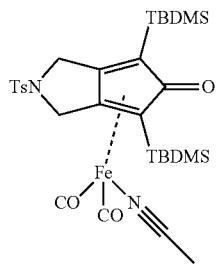
(B)

to obtain the compound of formula (E)

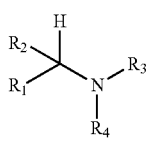
(E)

wherein $R_1$, $R_2$, $R_3$ and $R_4$ are as defined above.

According to another embodiment, the invention relates to a method of preparation of tertiary amines of formula (E), comprising a prior step of preparing of imines of formula (D)

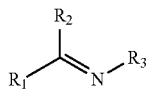
(D)

wherein $R_1$ and $R_2$ represent a hydrogen, aryl, allyl, $C_1$ to $C_{10}$ alkyl or $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative or a $C_3$ to $C_{10}$ formate,
comprising a step of contacting an aldehyde or ketone of formula (F)

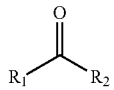
(F)

wherein $R_1$ and $R_2$ are as defined above,
and an amine of formula (G)

$R_3$—$NH_2$ (G)

wherein $R_3$ is as defined above,
to obtain the imine of formula of formula (D) as defined above;
a prior step of preparing of the catalyst,
comprising a step of adding trimethylamine oxide to the complex of formula (A):

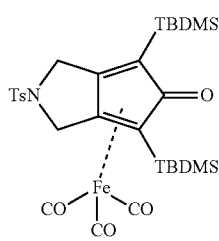
(A)

said two prior steps may occur in any order,
and a step of alkylation of a primary or secondary alcohol of formula (C)

$R_4OH$ (C)

wherein $R_4$ represents a $C_2$ to $C_{10}$ alkyl, or a $C_3$ to $C_{10}$ cycloalkyl on an imine of formula (D) prepared in the previous step

(D)

wherein $R_1$, $R_2$ and $R_3$ are as defined above,
in the presence of catalyst of formula (B) prepared in the preceding step and as defined above,
to obtain the compound of formula (E)

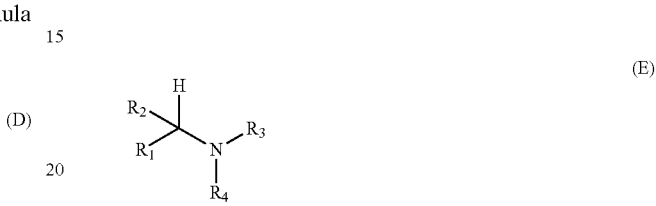
(E)

wherein $R_1$, $R_2$, $R_3$, and $R_4$ are as defined above.

According to a preferred embodiment of the invention, the imine of formula (D) is chosen from:

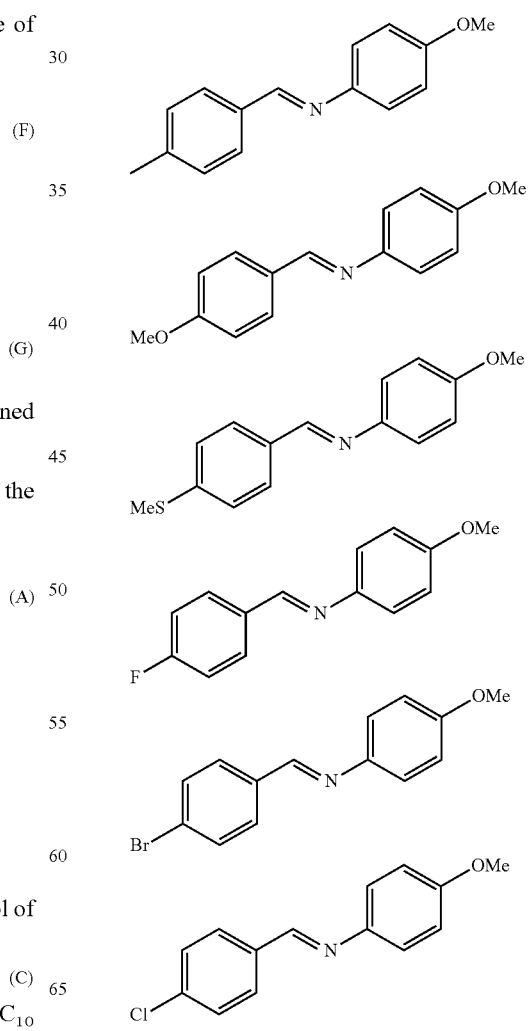

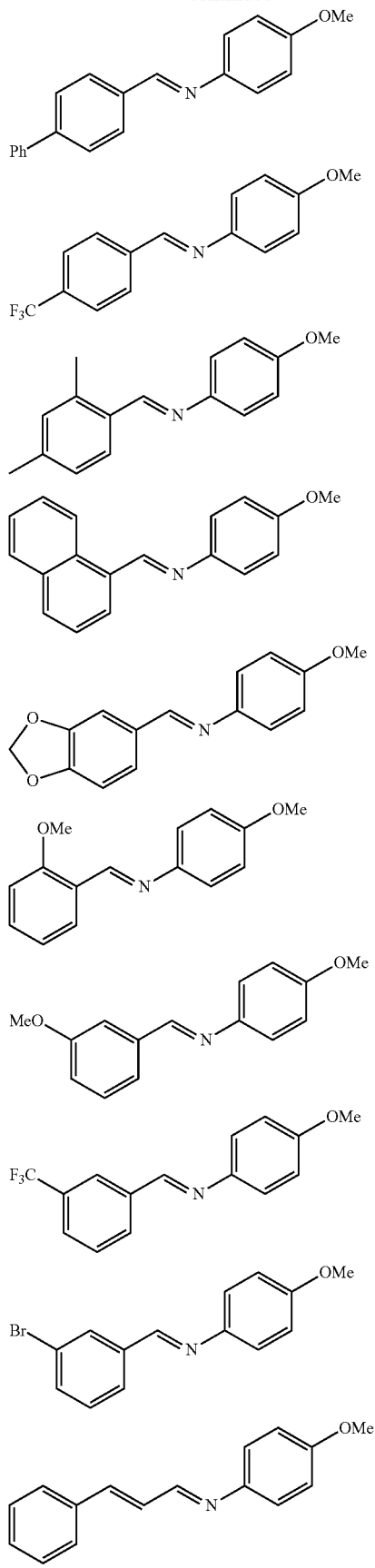
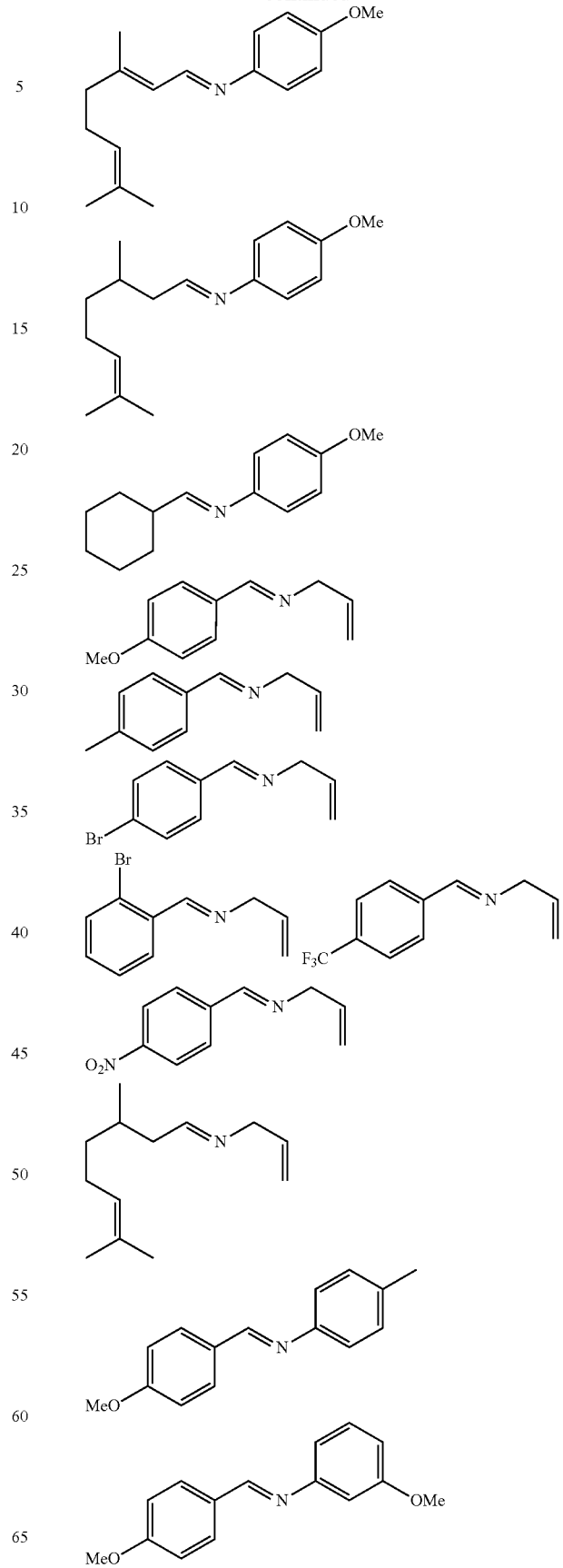

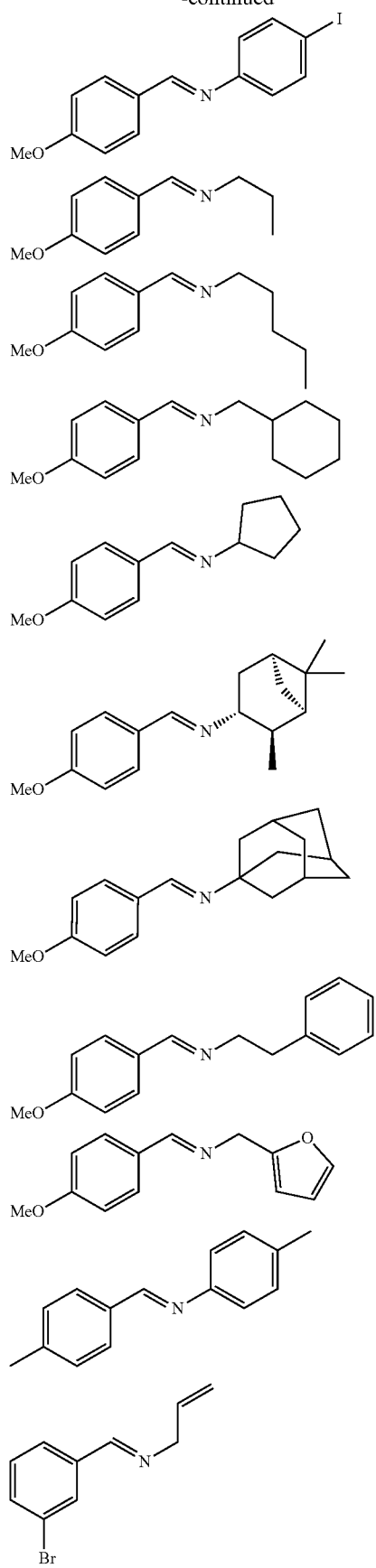
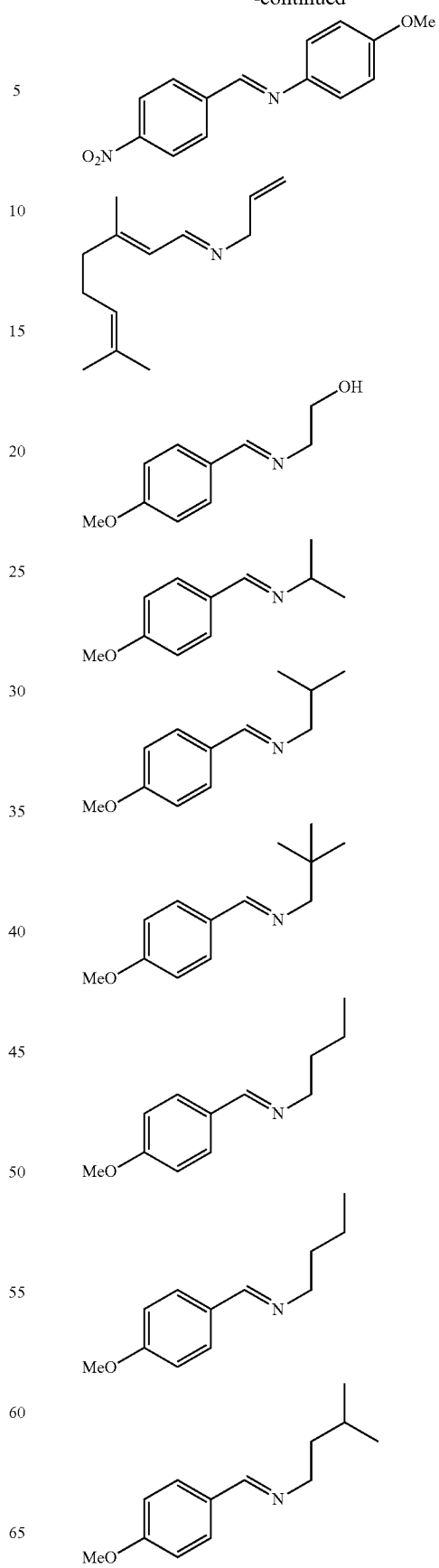

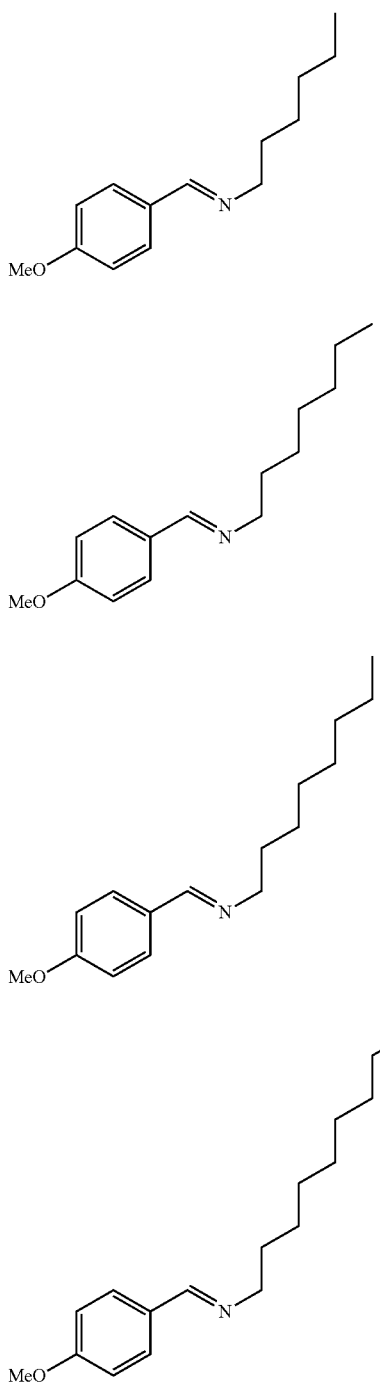
The present invention also relates to novel tertiary amines having one of the following formulas:
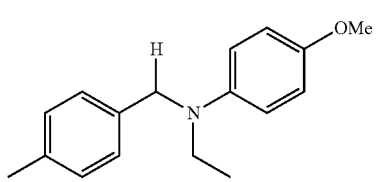
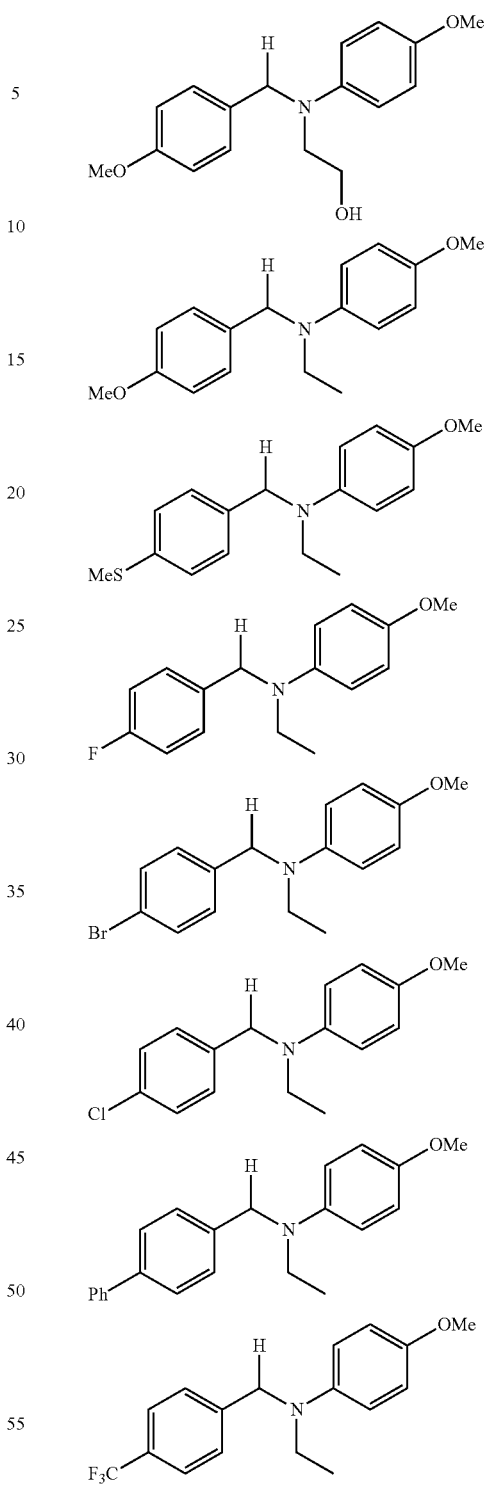
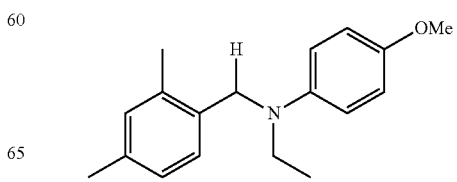

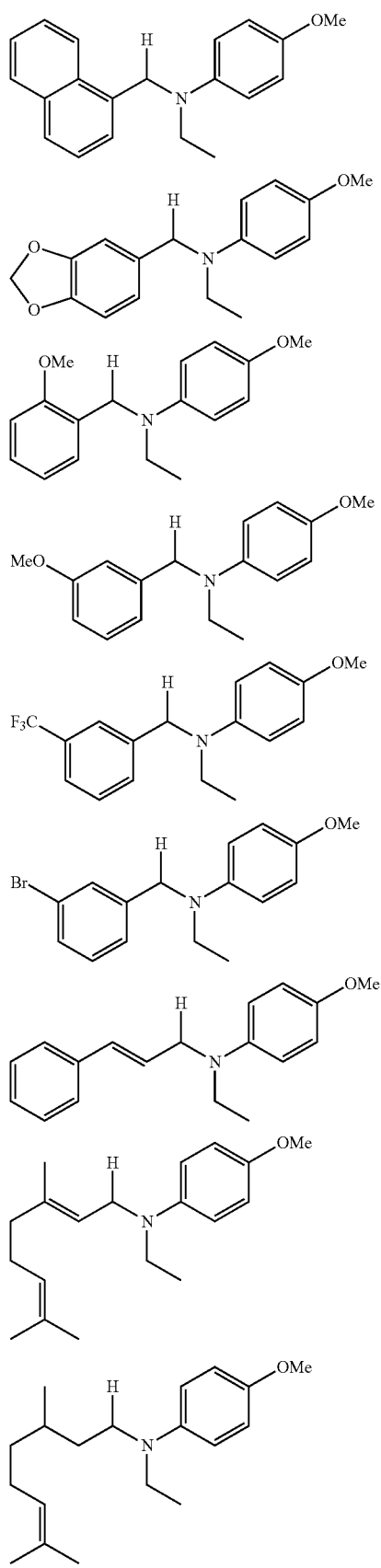
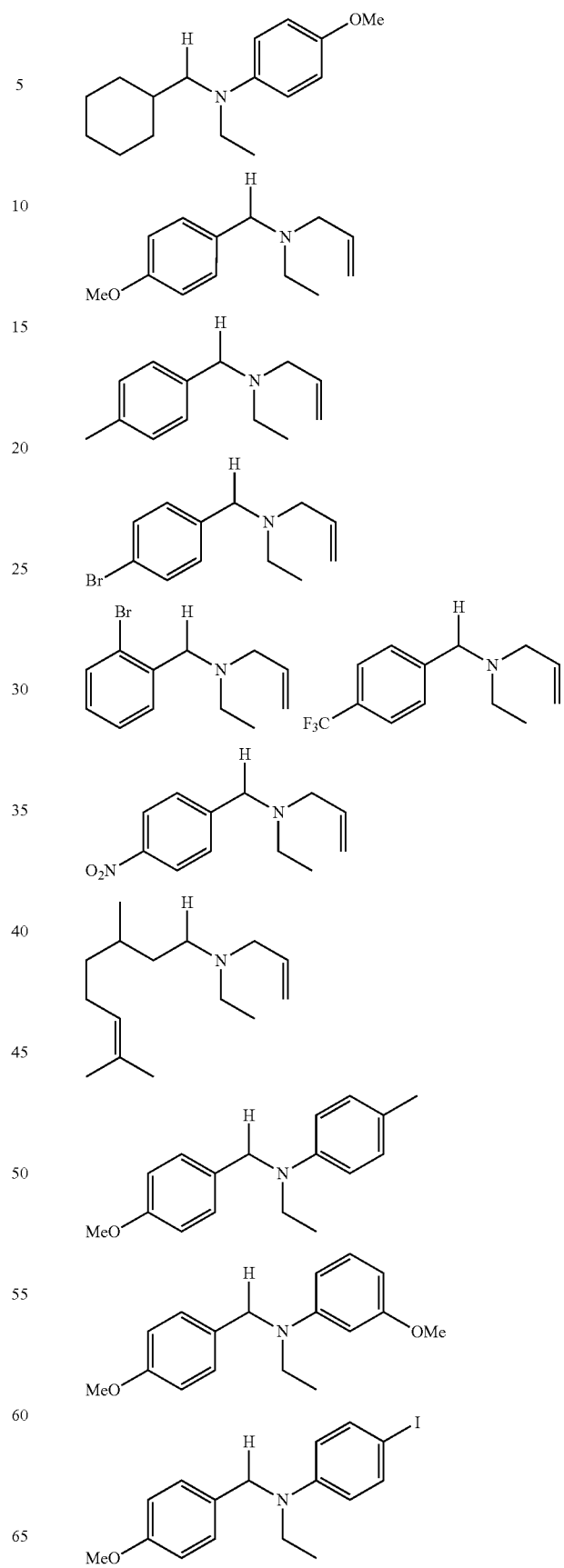

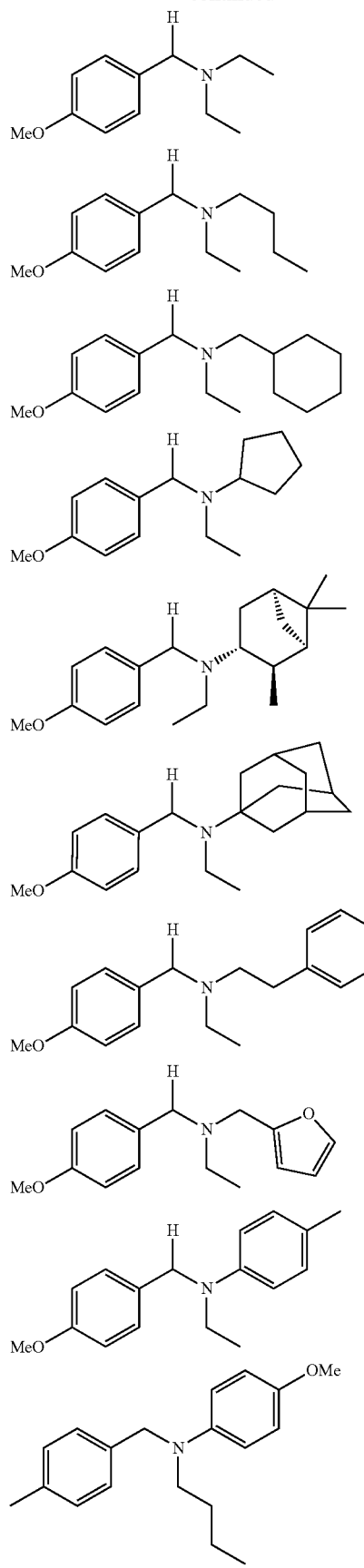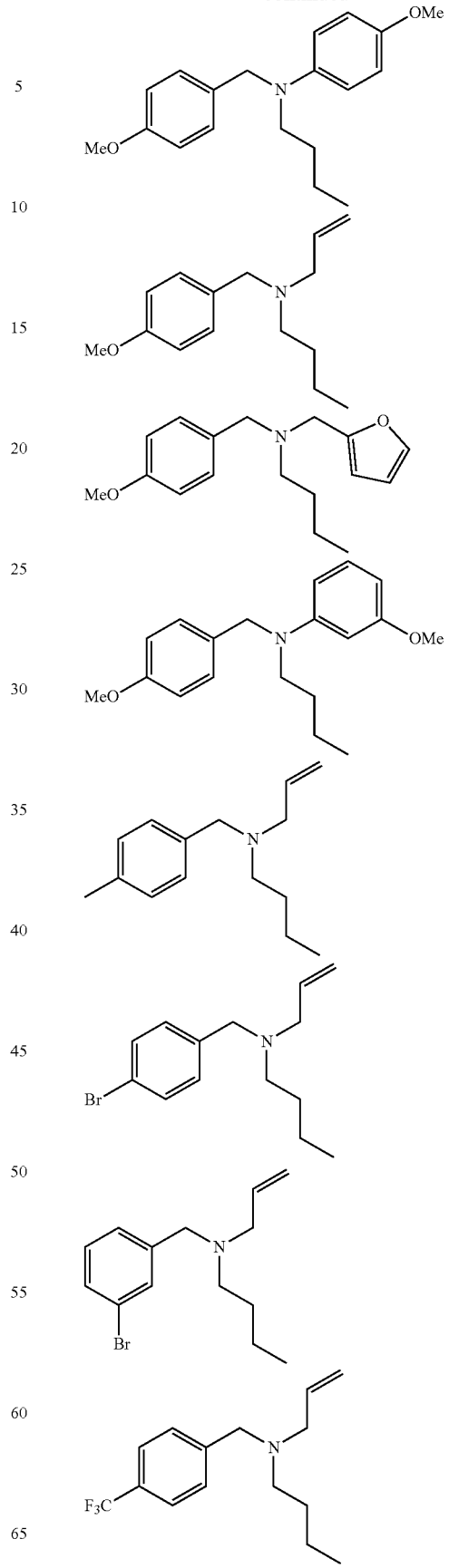

-continued
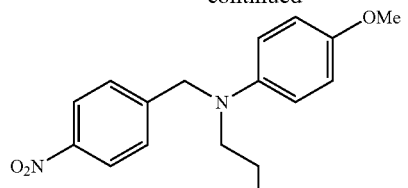
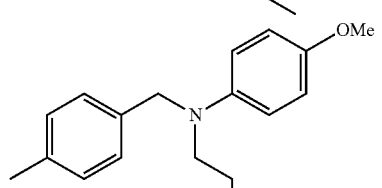
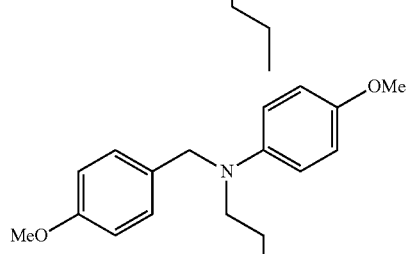
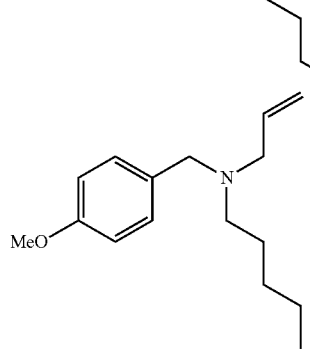
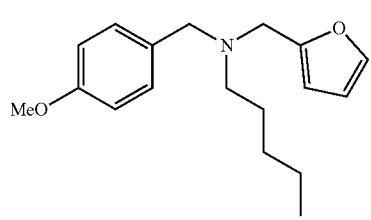
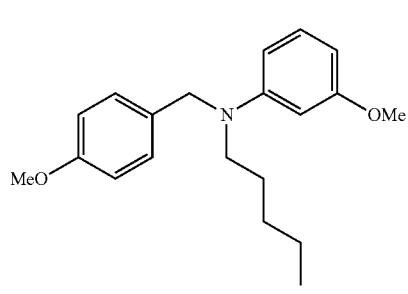
-continued
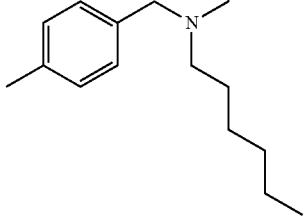
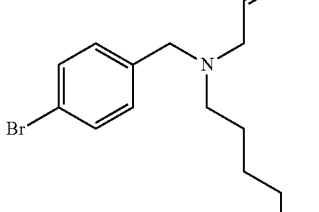
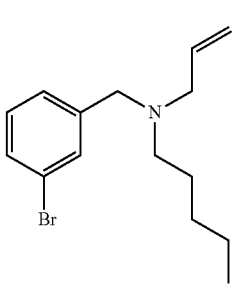
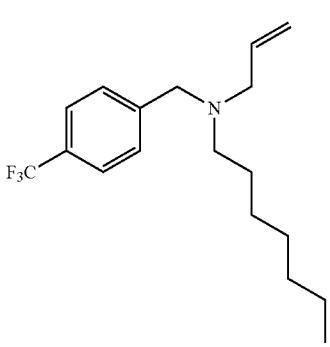
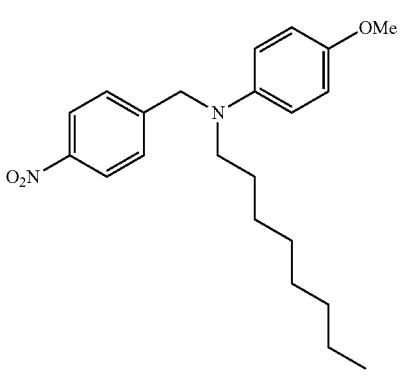

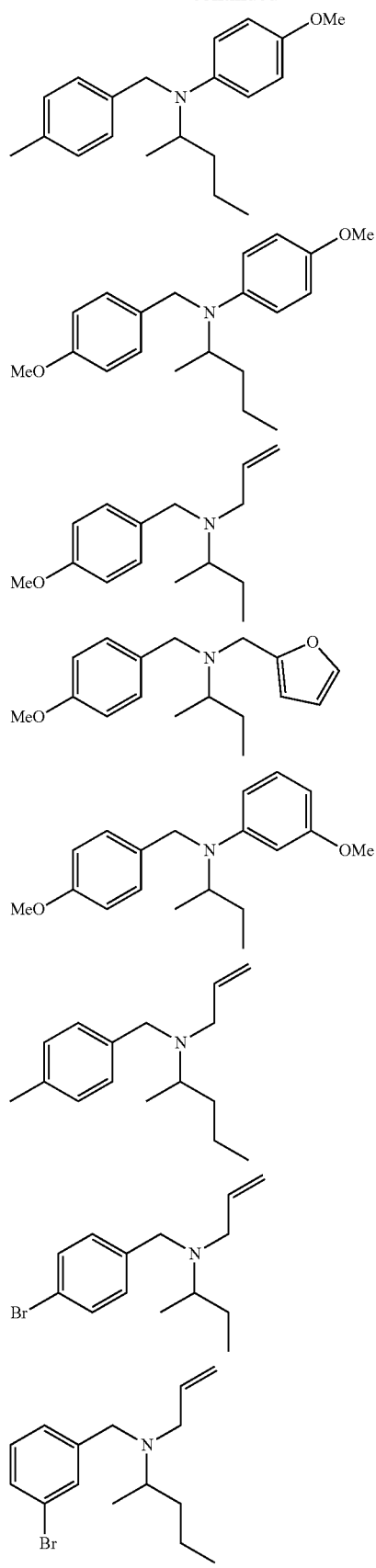
The present invention also concerns new tertiary amines of one of the following formula:
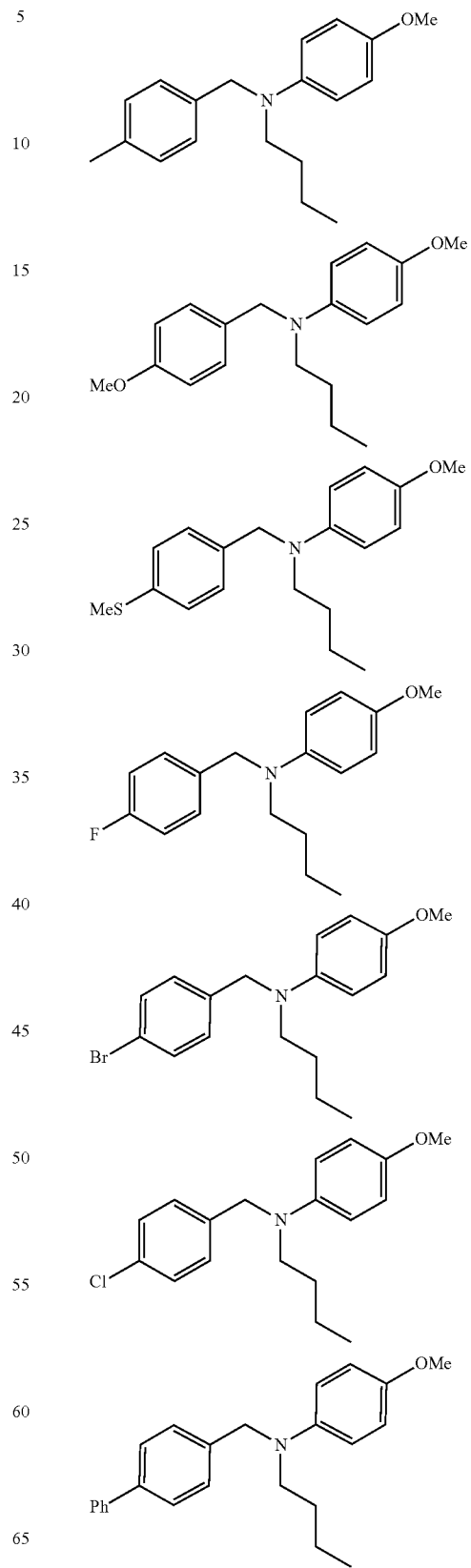

-continued
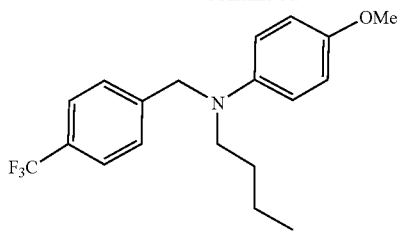
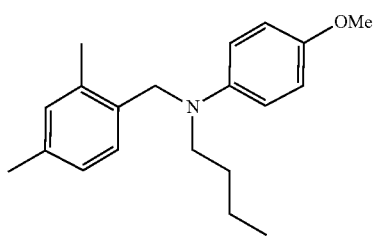
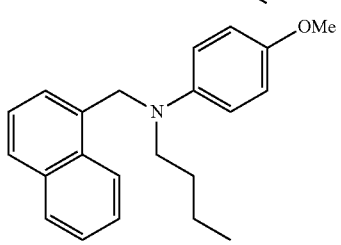
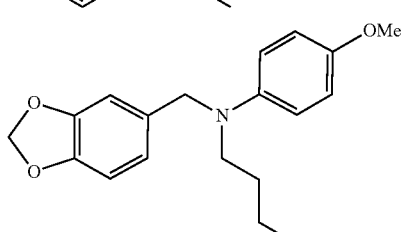
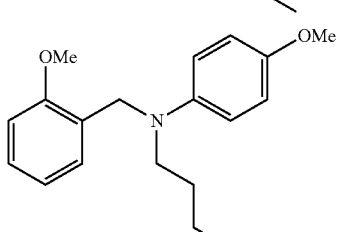
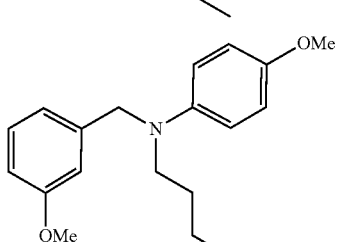
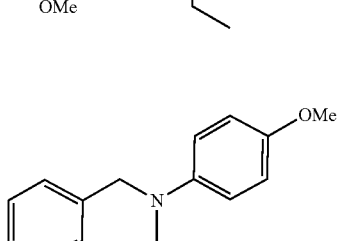
-continued
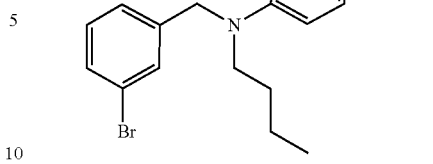
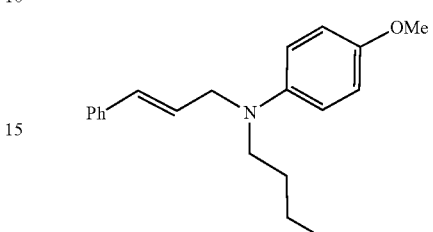
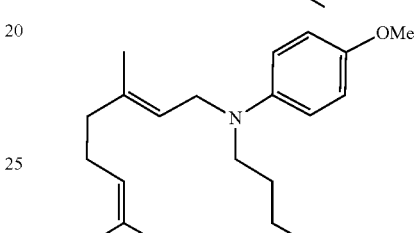
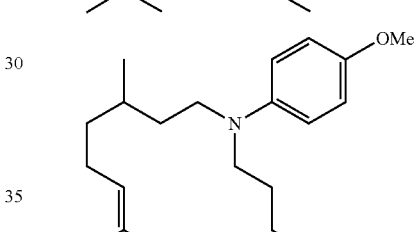
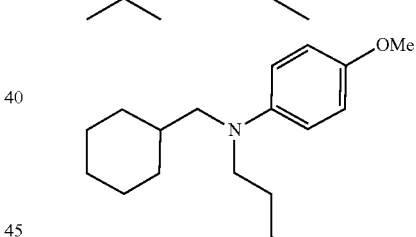
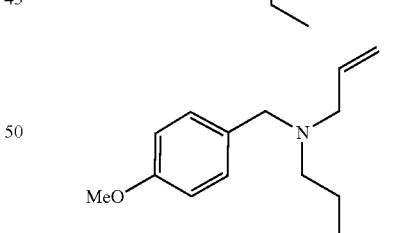
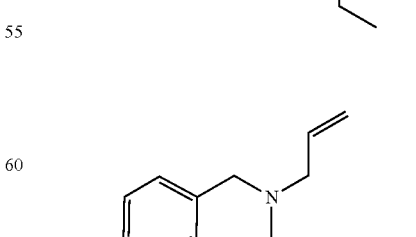

-continued
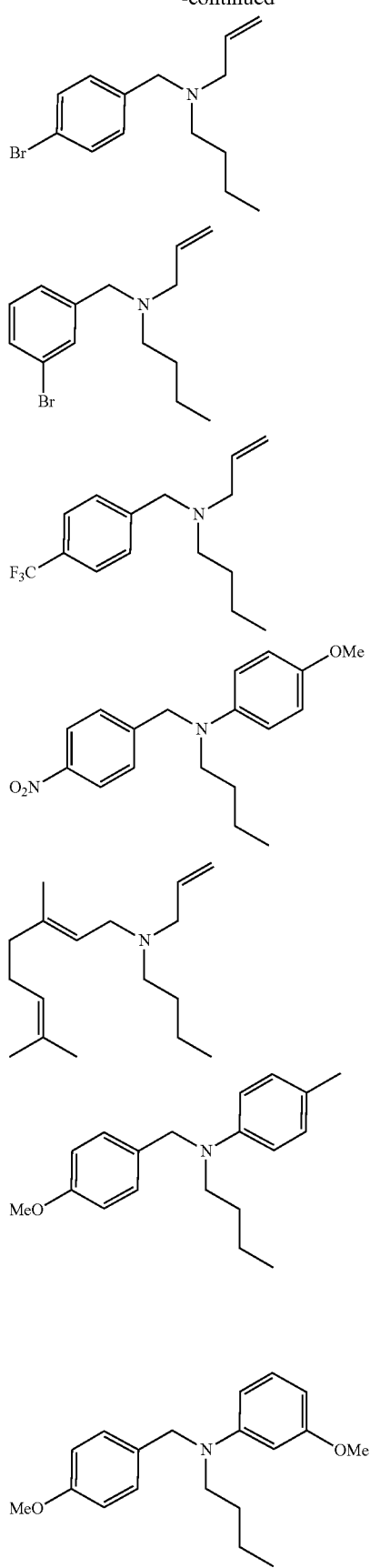
-continued
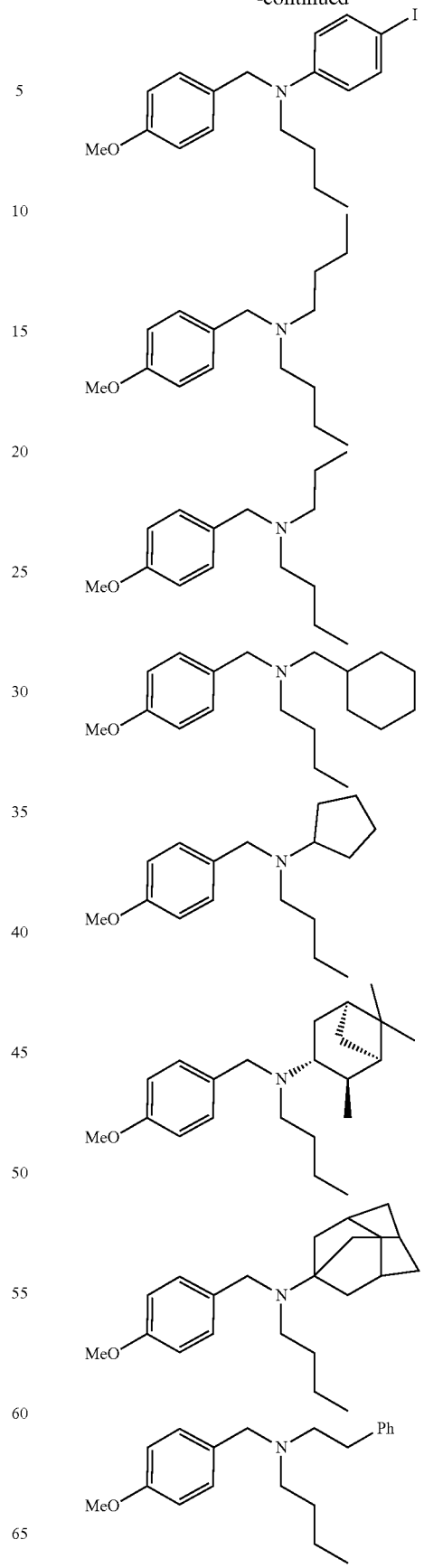

47
-continued
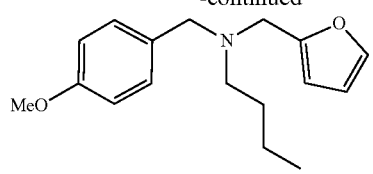
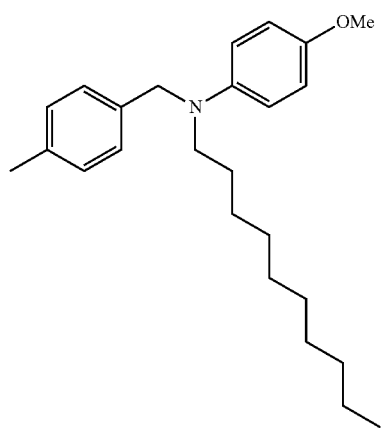
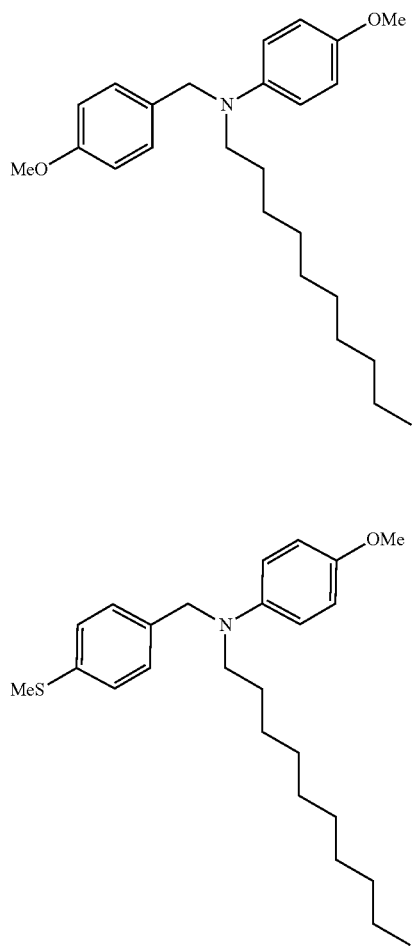
48
-continued
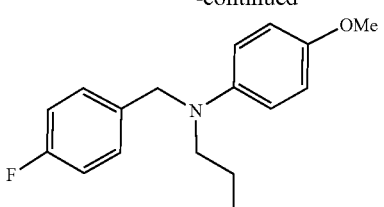
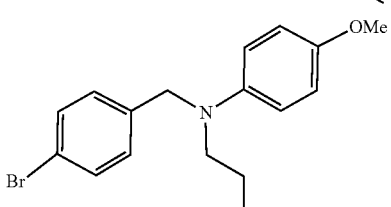
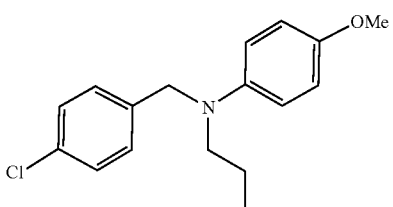
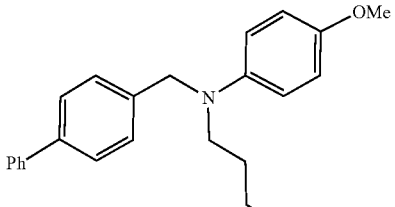

-continued
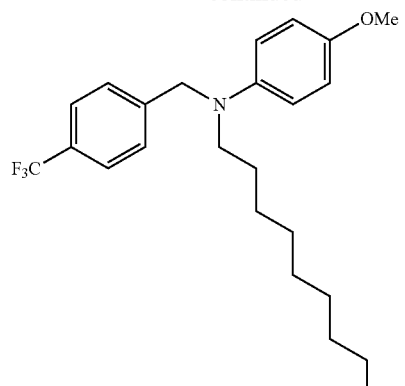
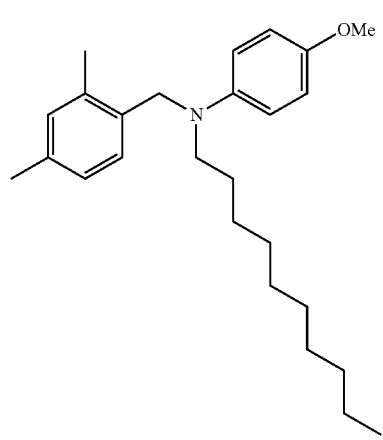
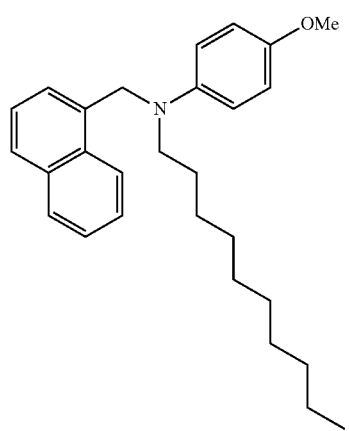
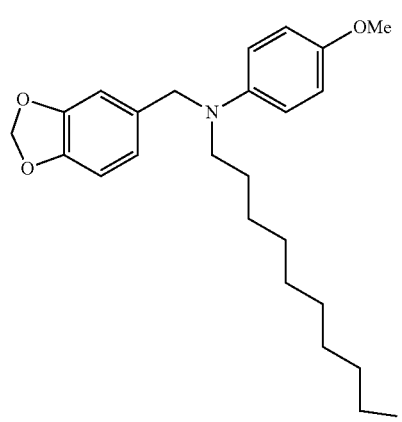
-continued
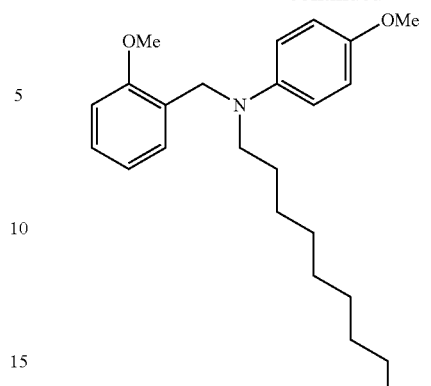
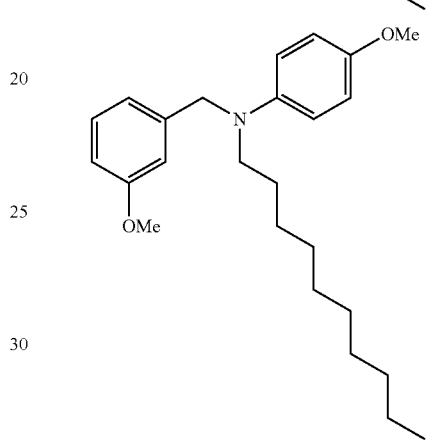
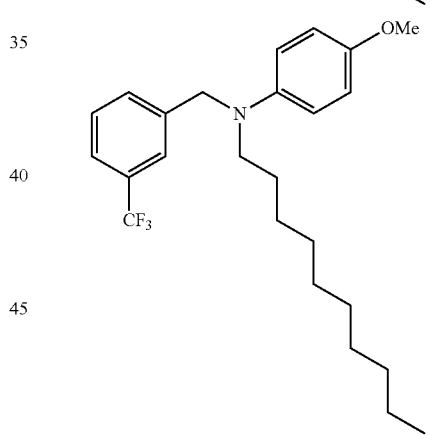
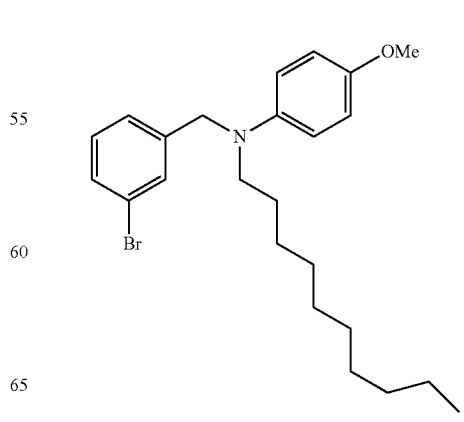

-continued
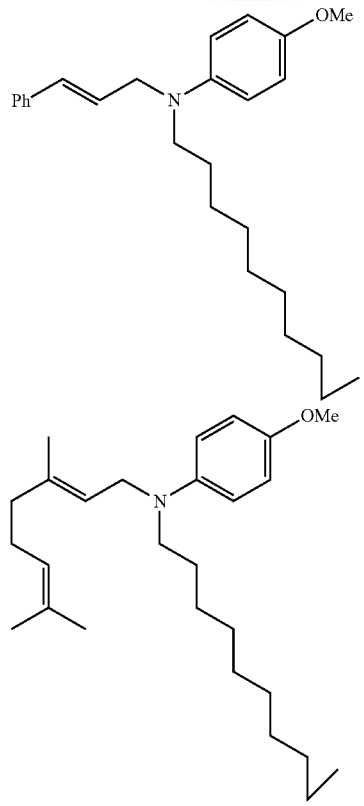
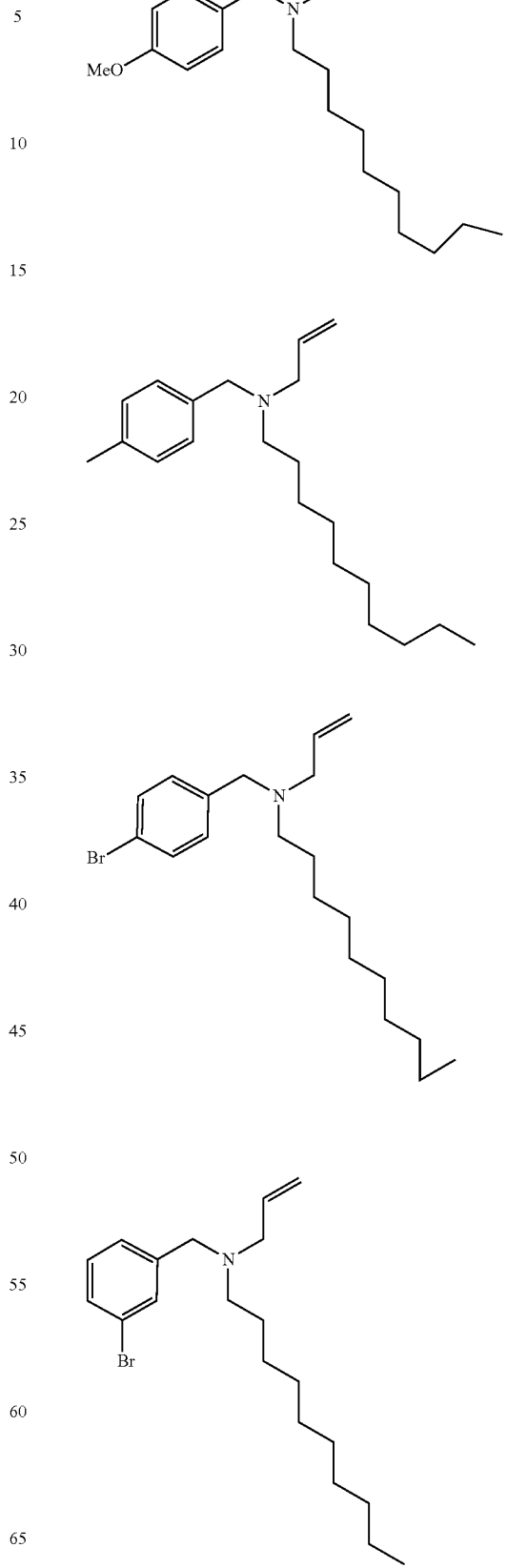

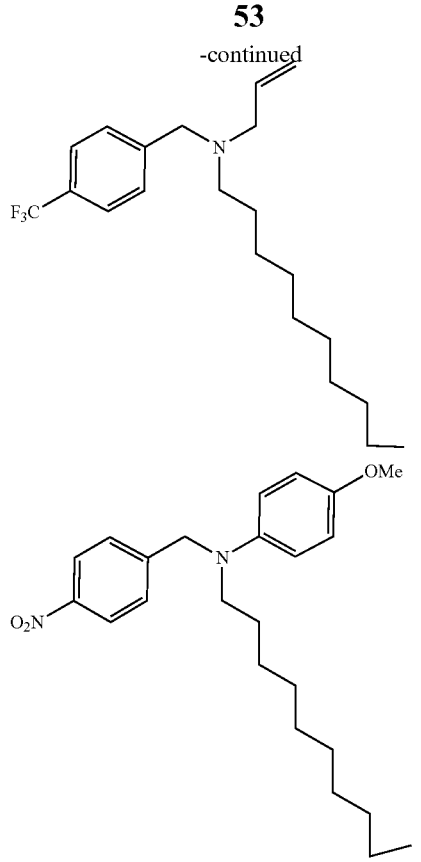
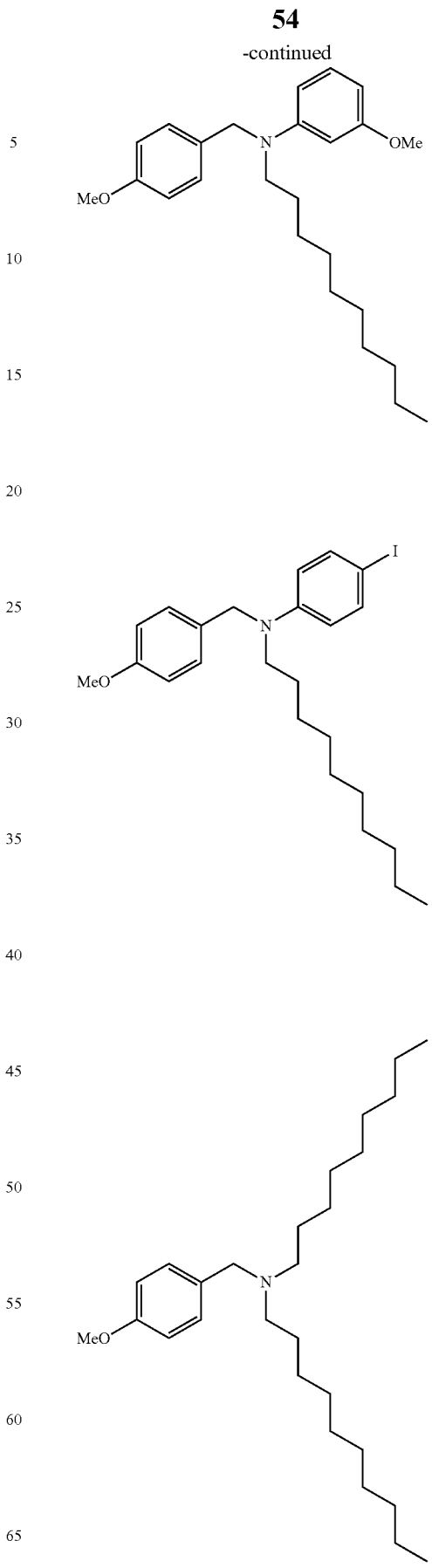

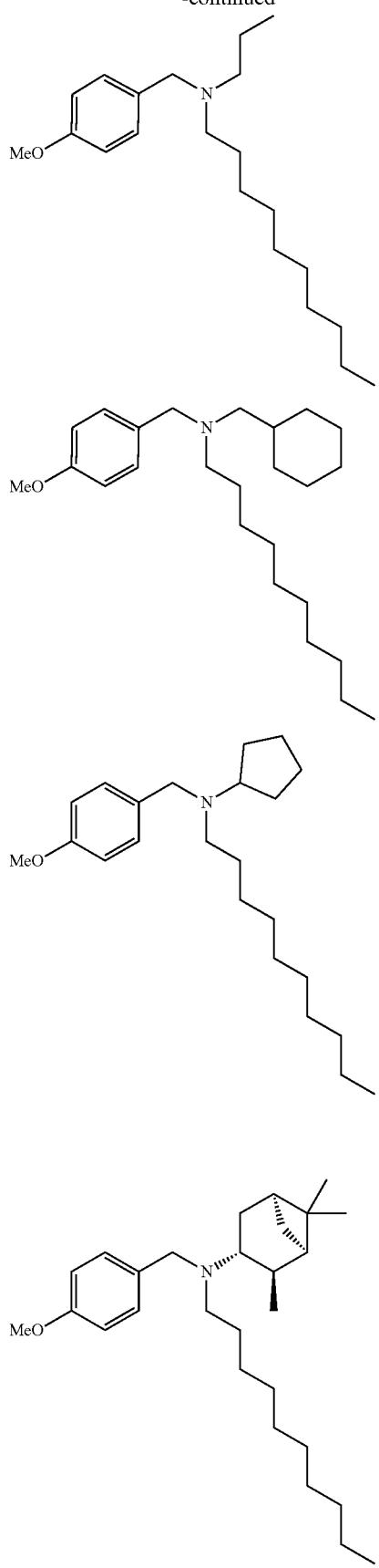
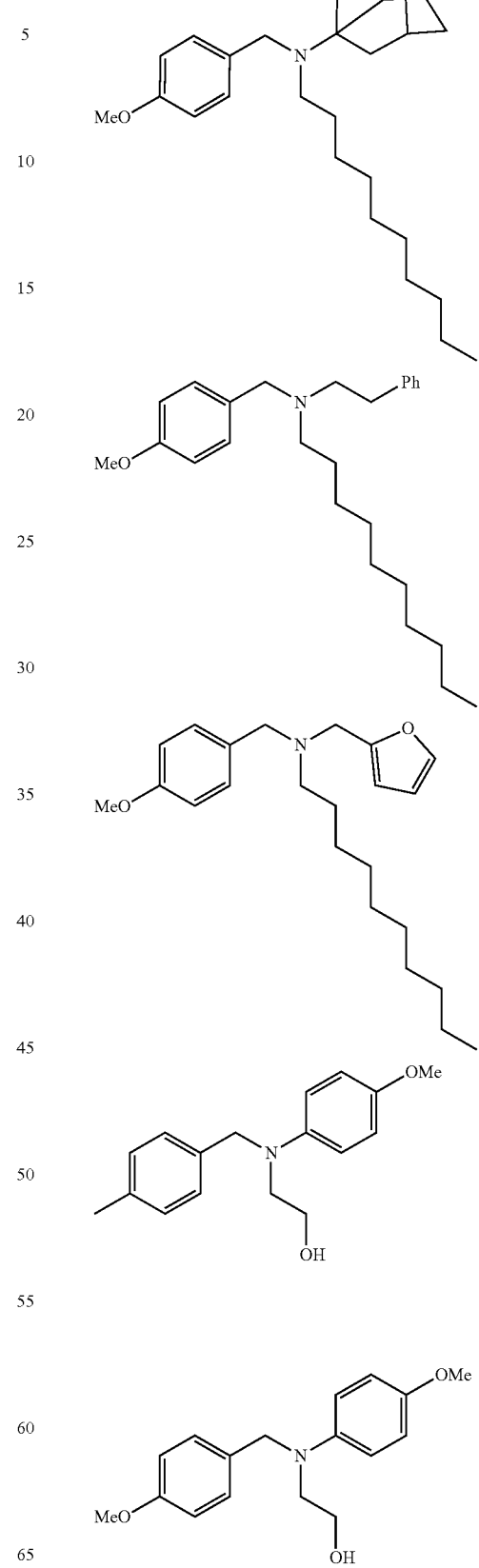

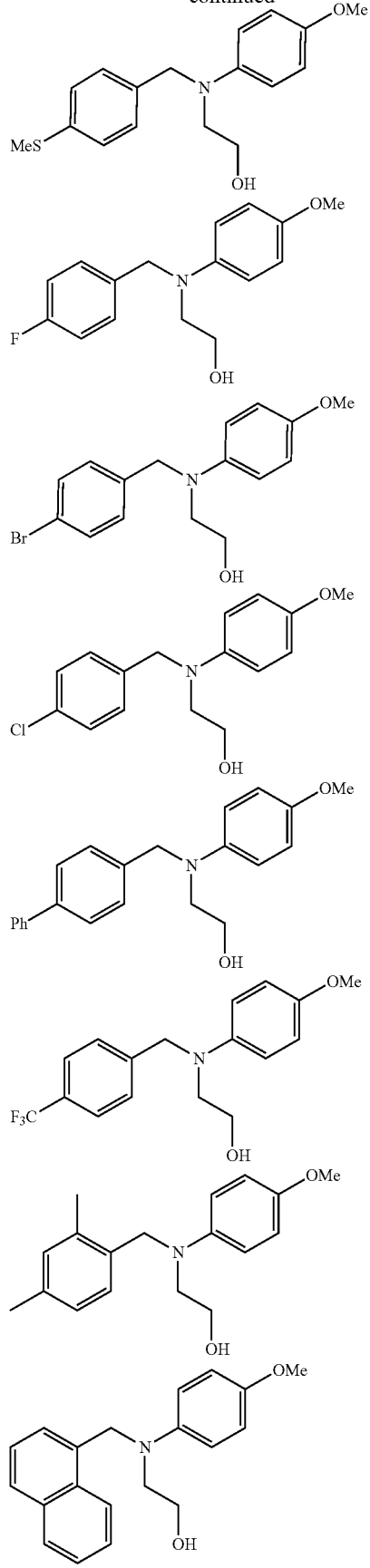
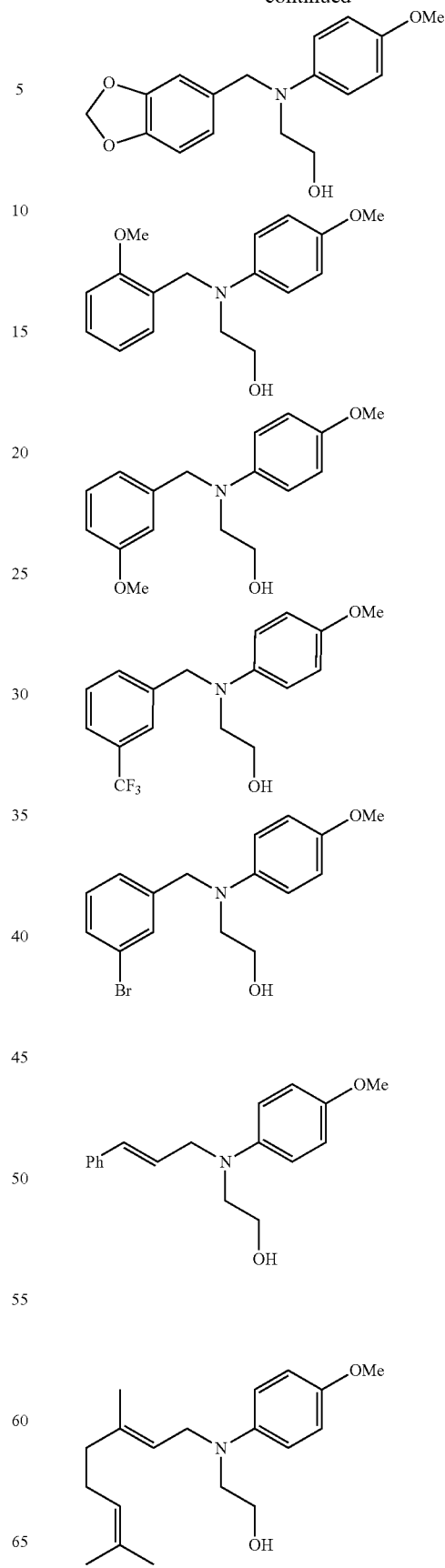

59
-continued
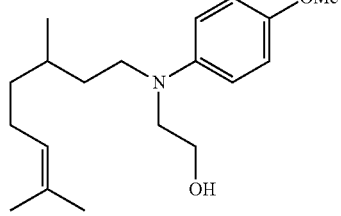
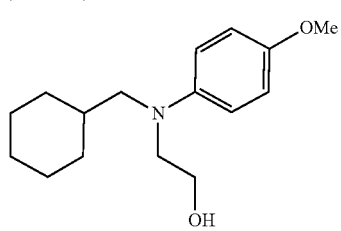
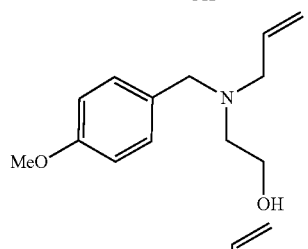
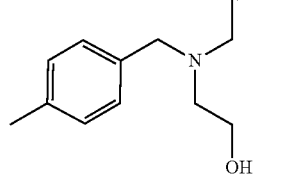
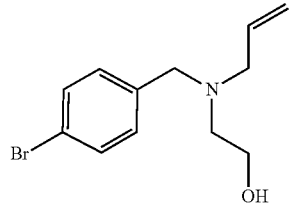
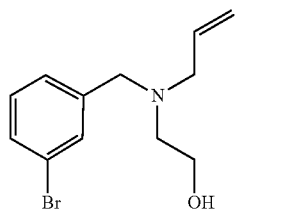
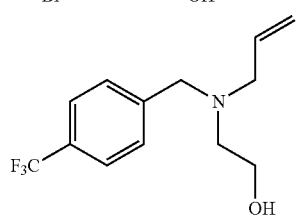
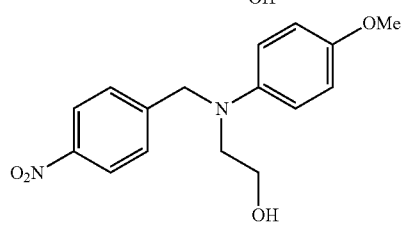
60
-continued
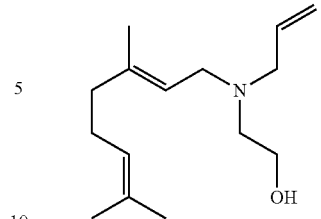
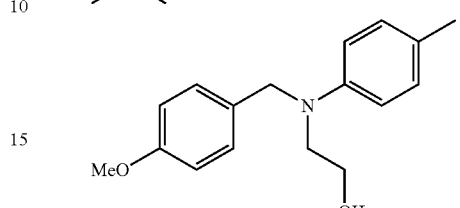
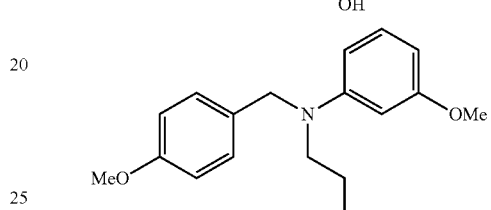
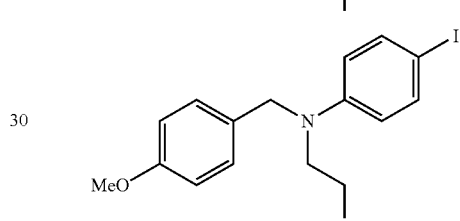
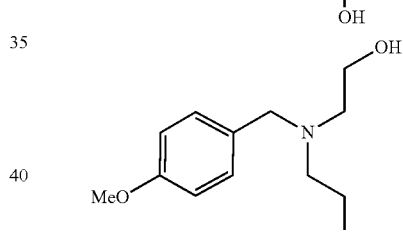
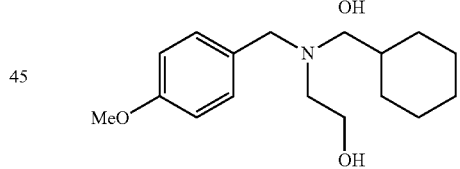
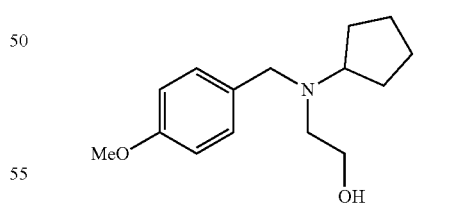
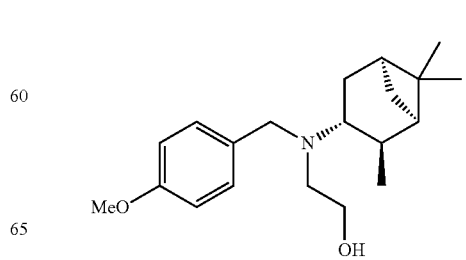

-continued
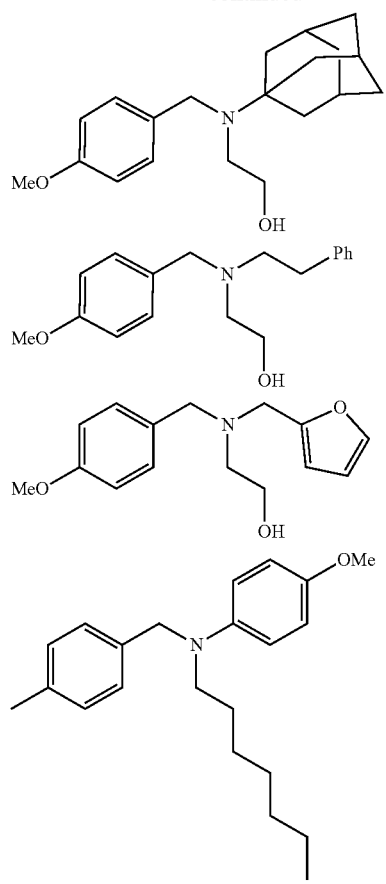
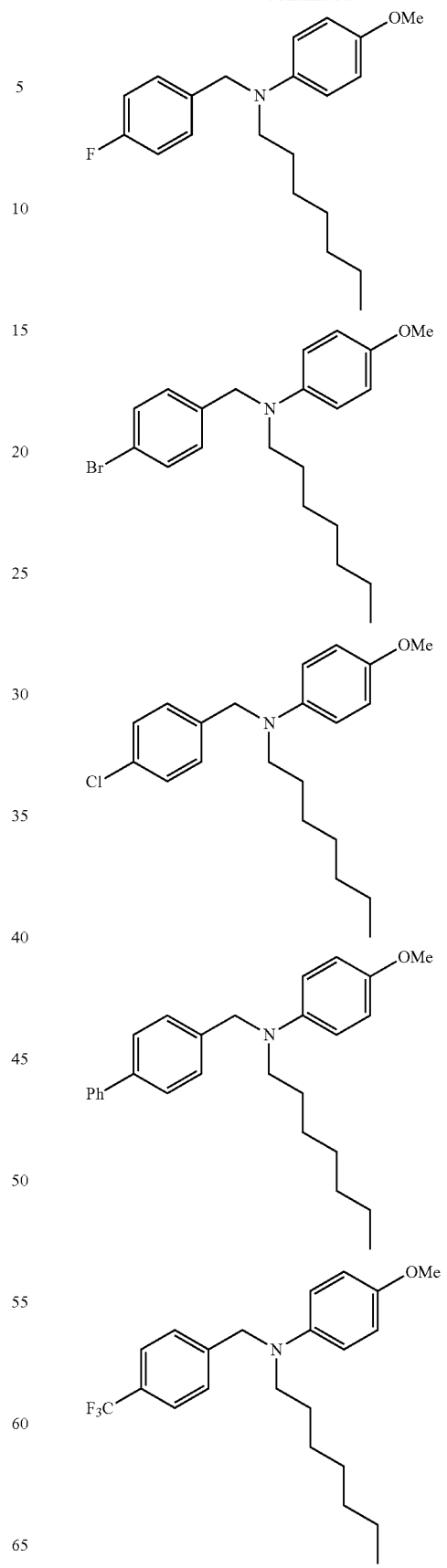

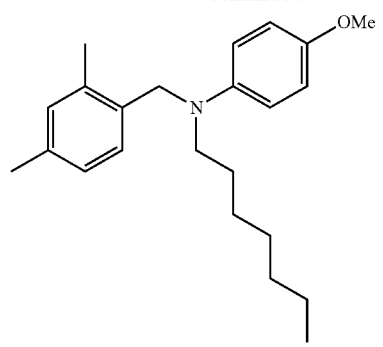
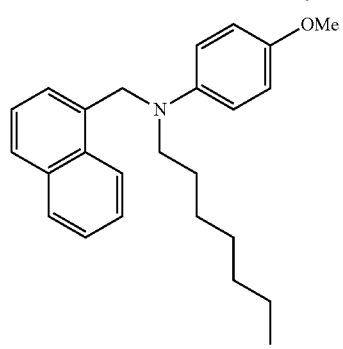
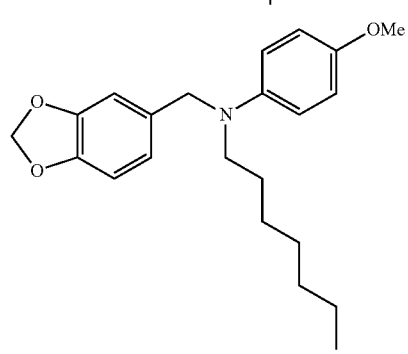
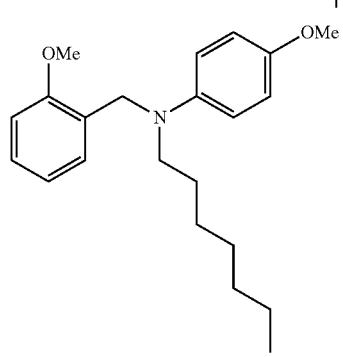
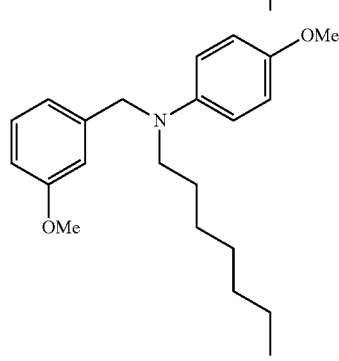
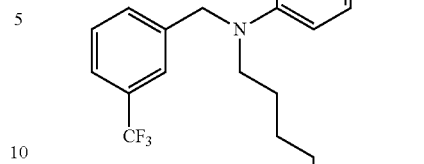
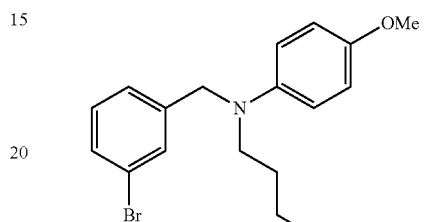
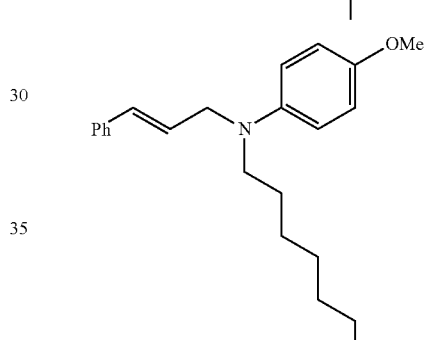
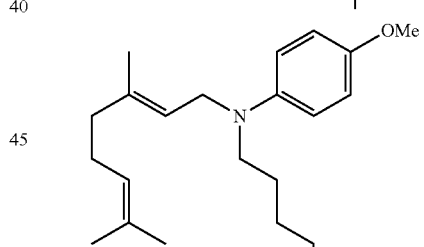
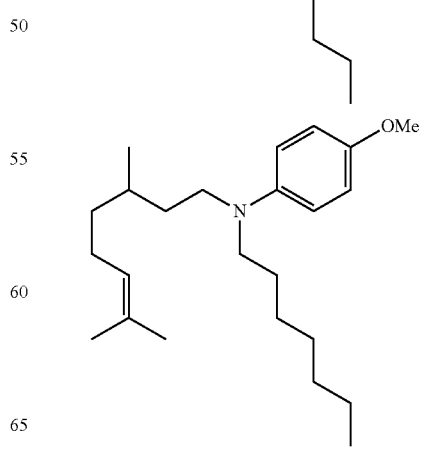

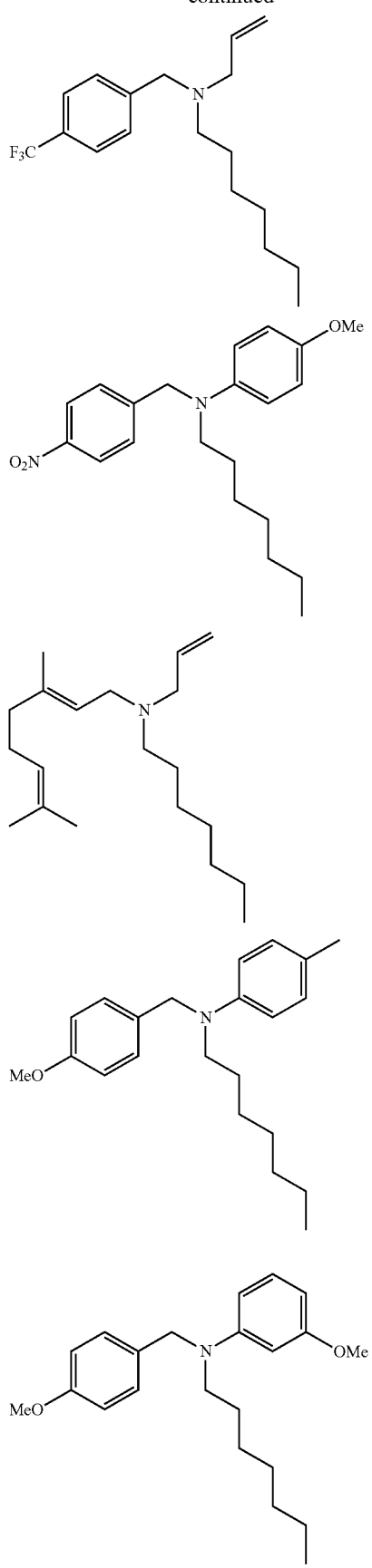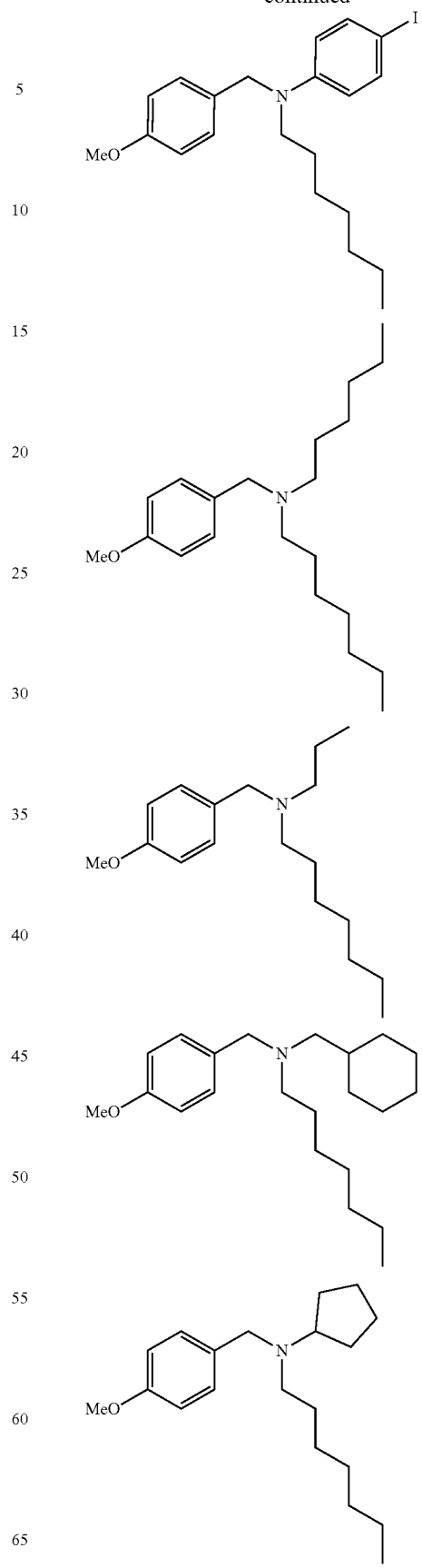

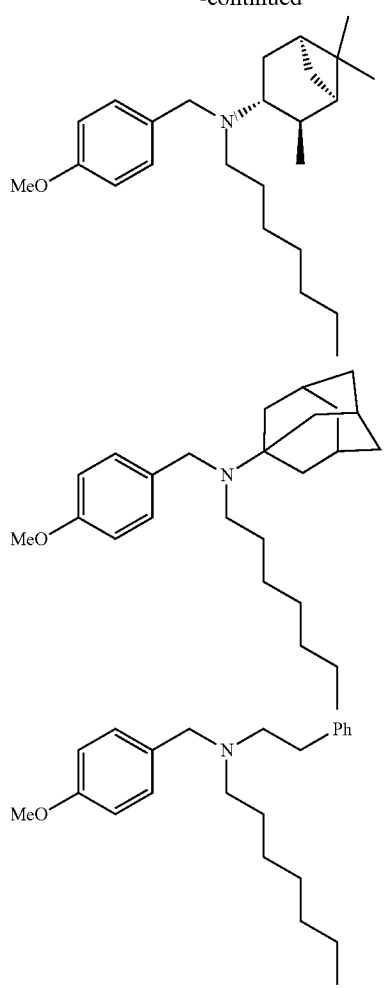
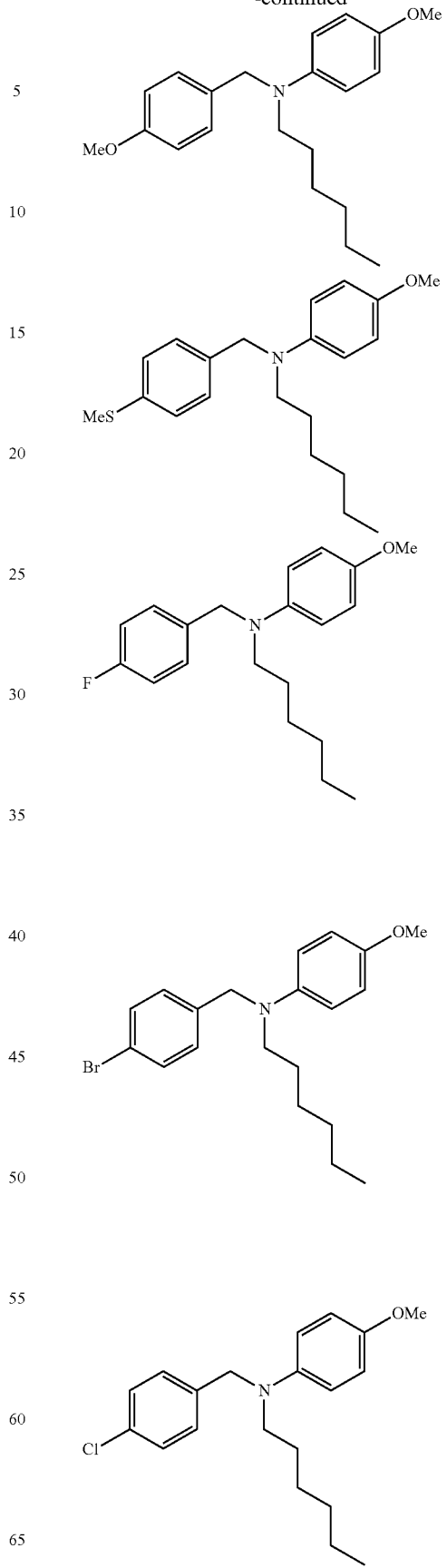

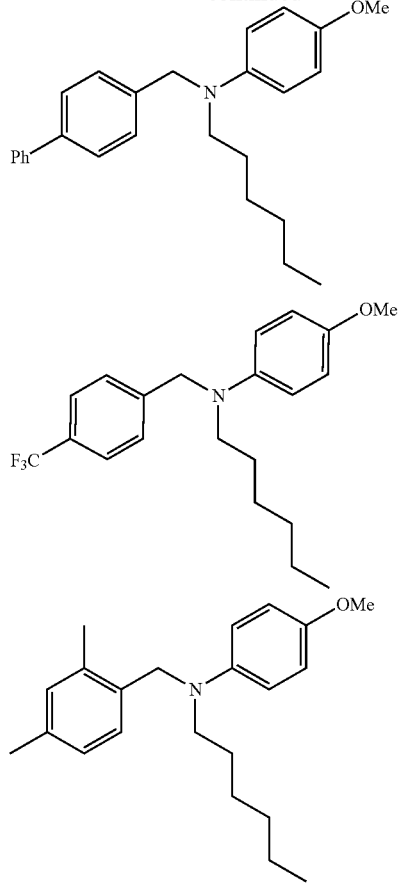
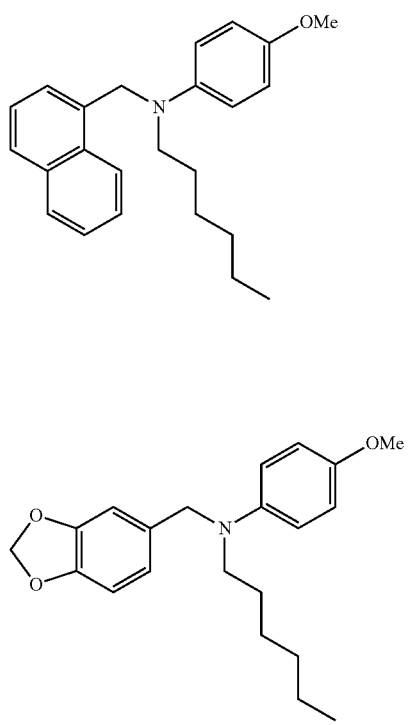
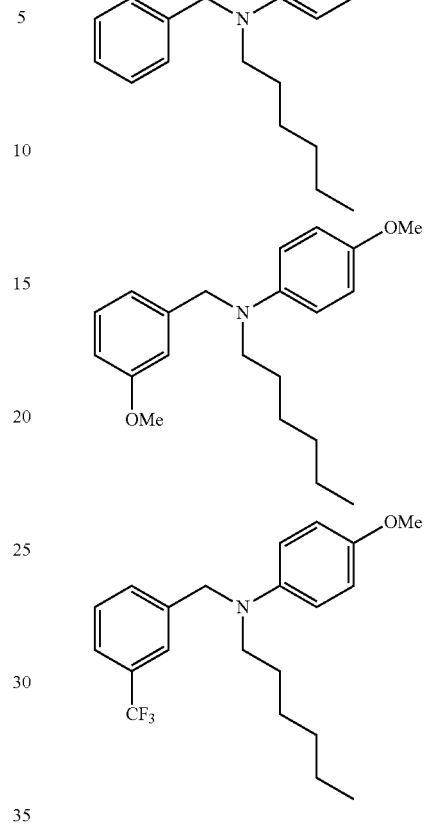

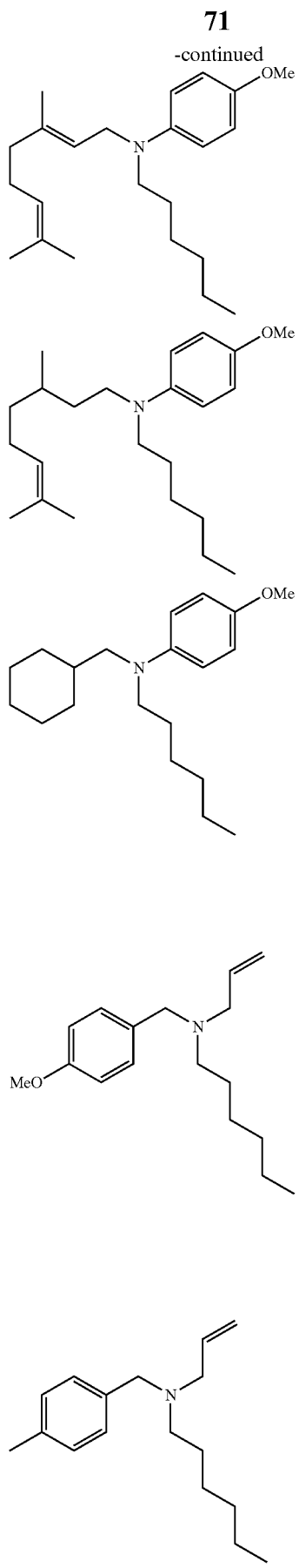
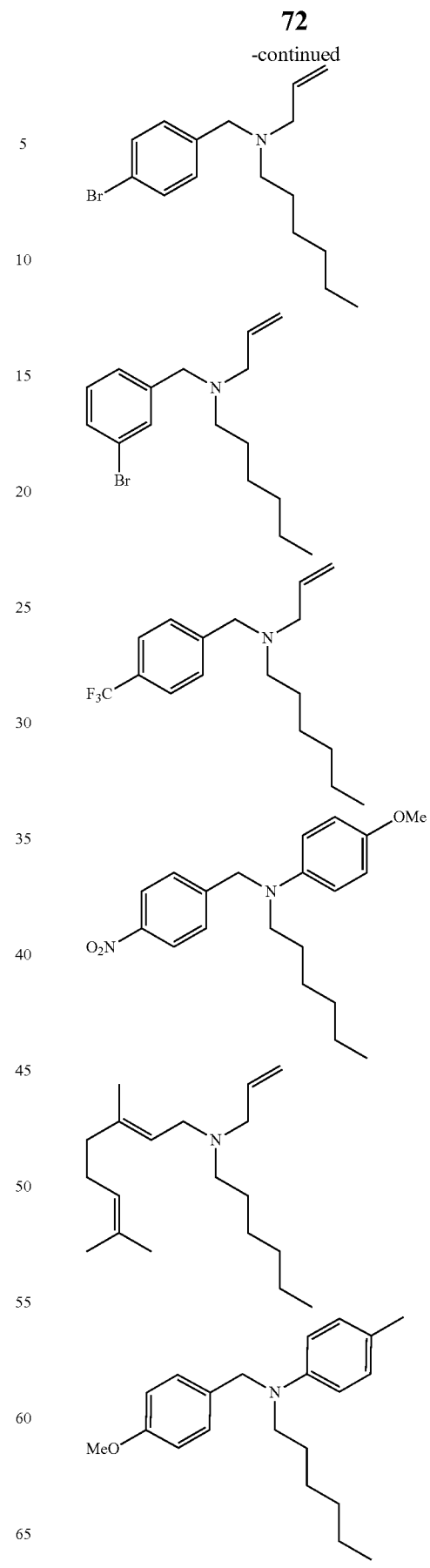

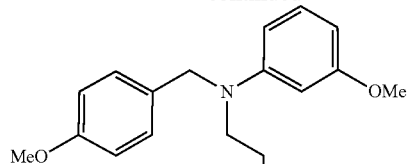
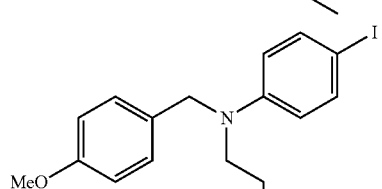
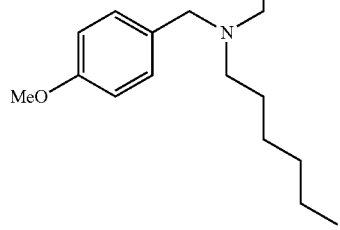
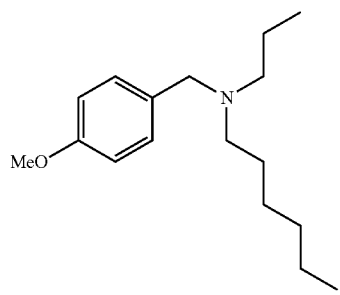
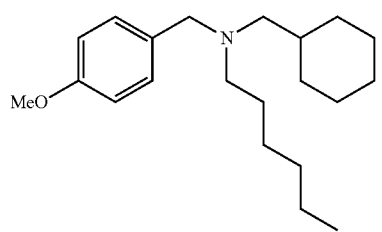
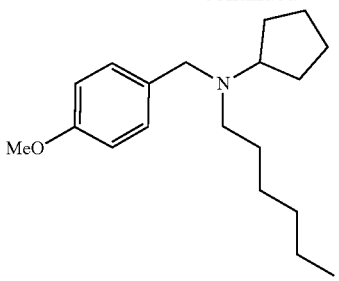
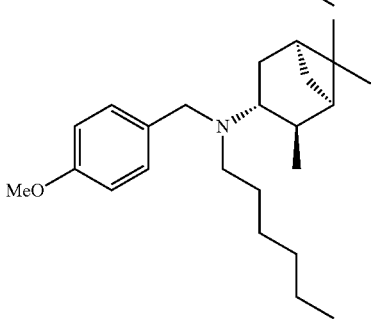
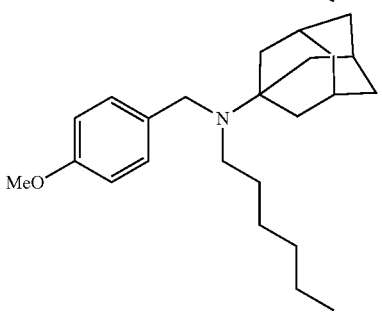
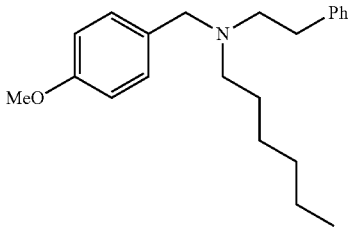
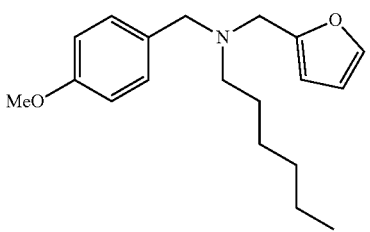
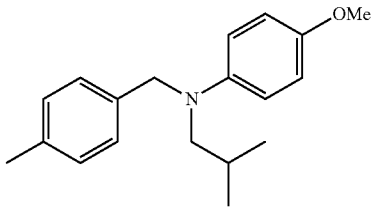

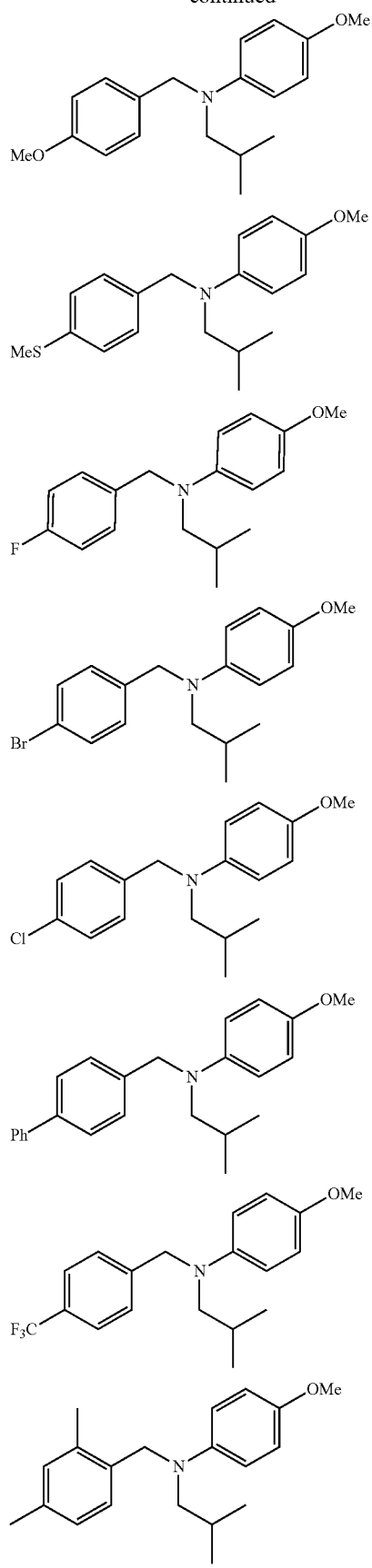
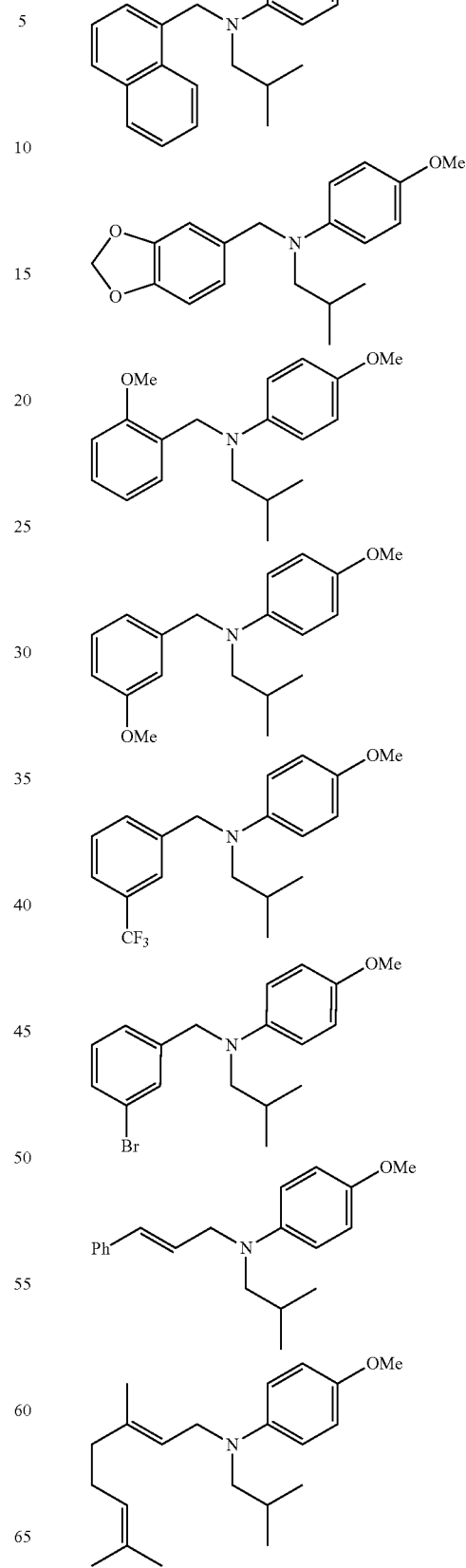

77
-continued
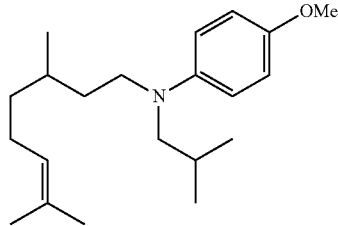
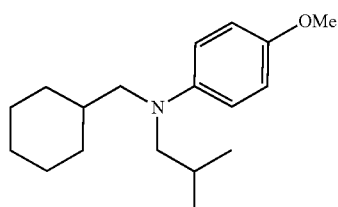
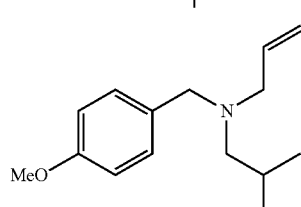
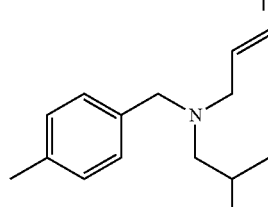
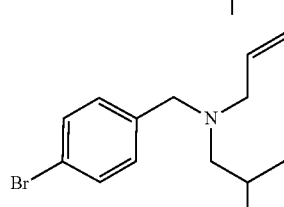
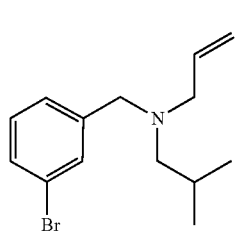
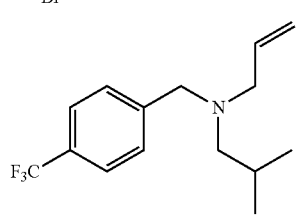
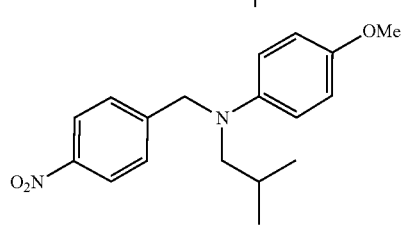
78
-continued
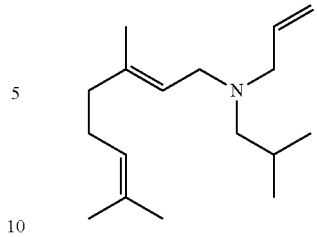
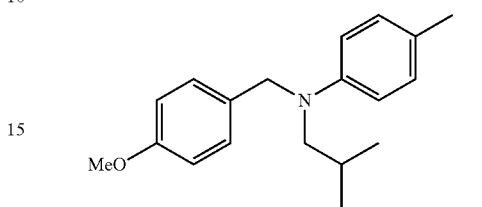
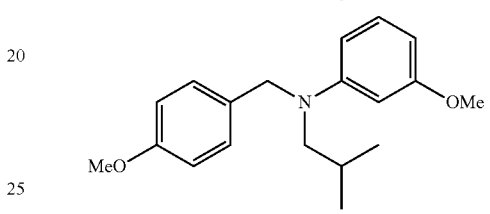
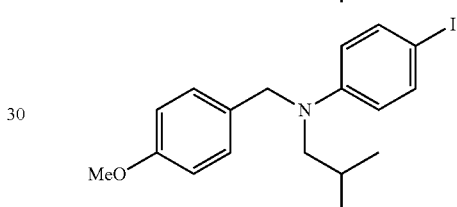
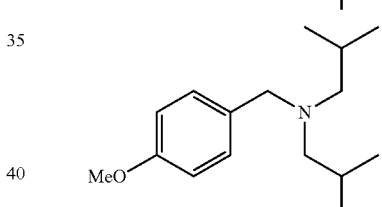
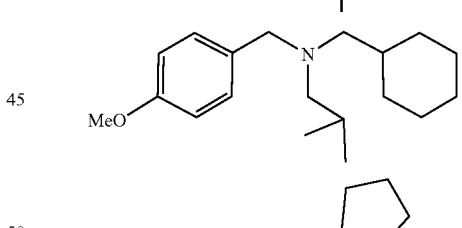
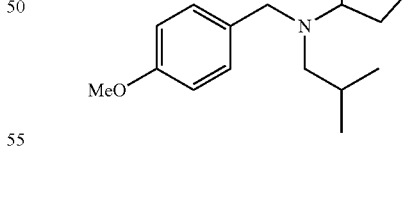
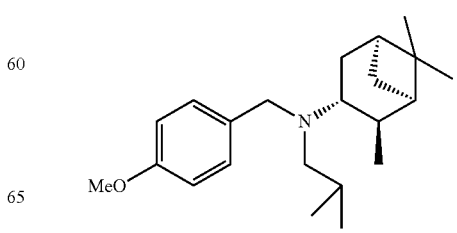

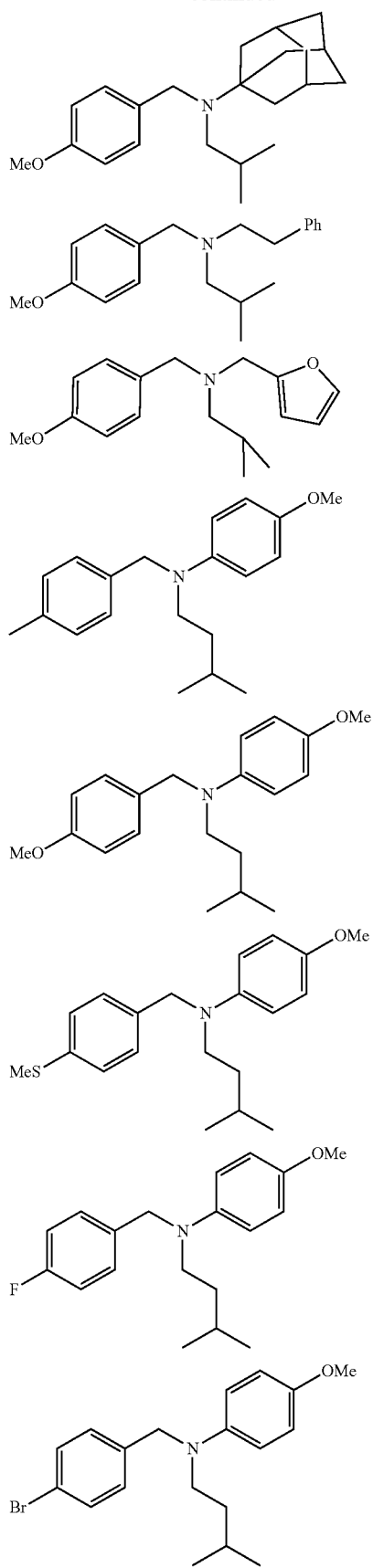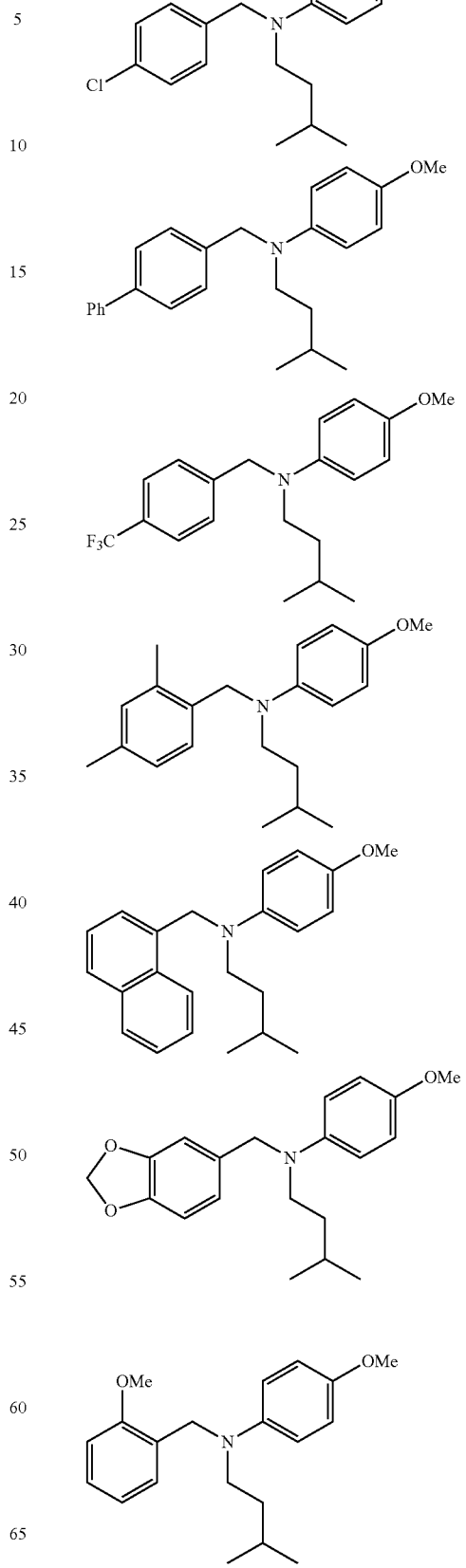

-continued
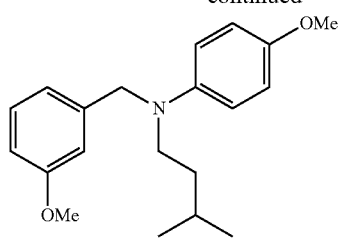
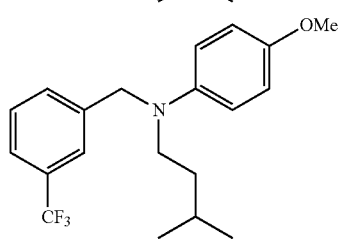
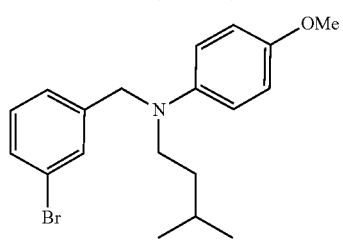
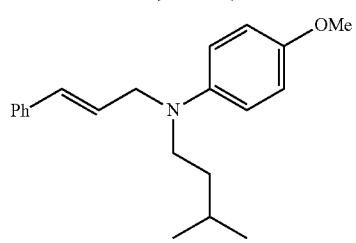
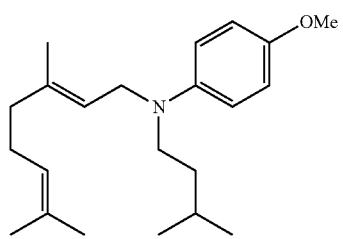
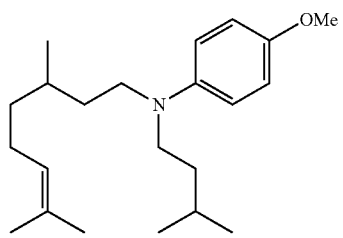
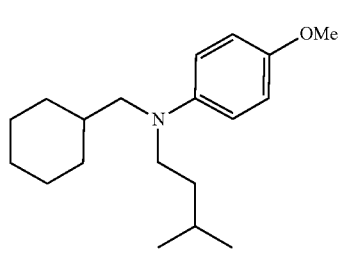
-continued
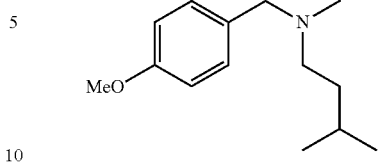
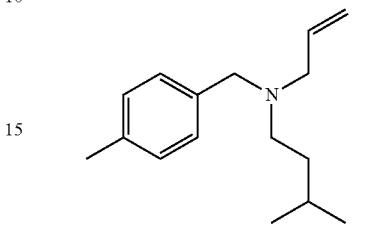
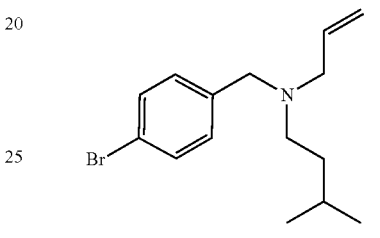
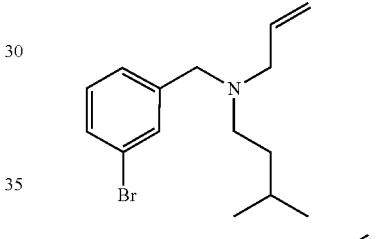
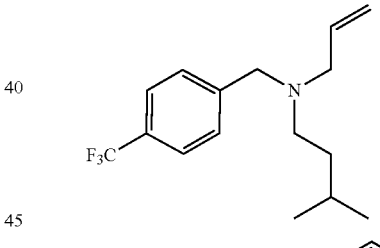
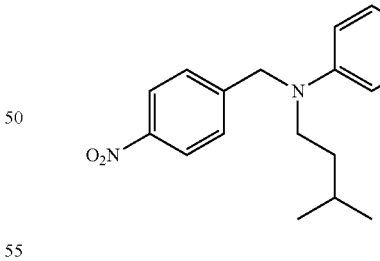
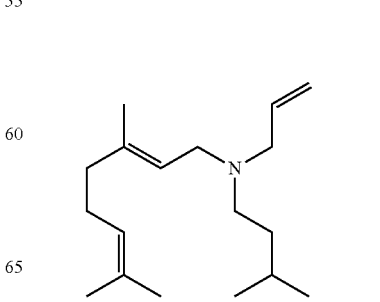

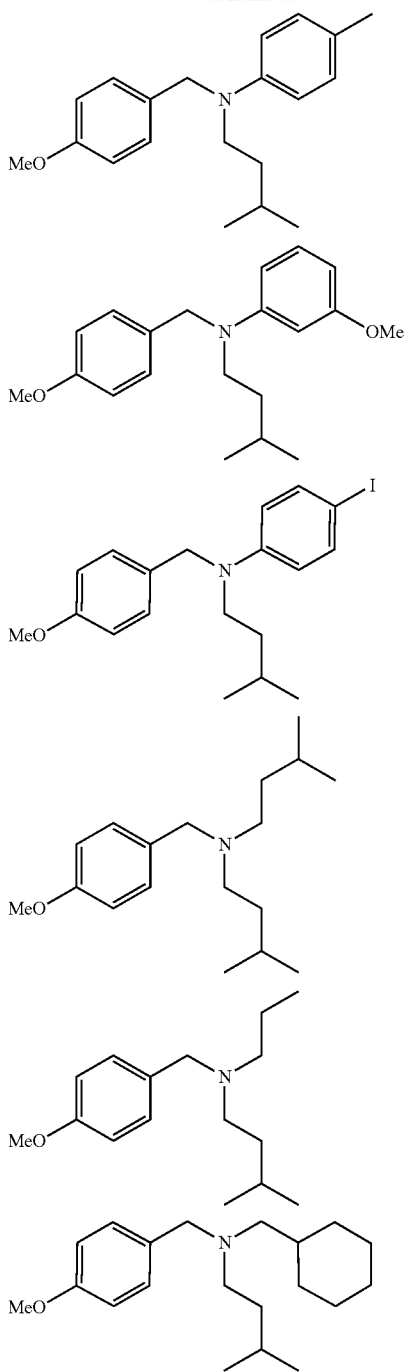
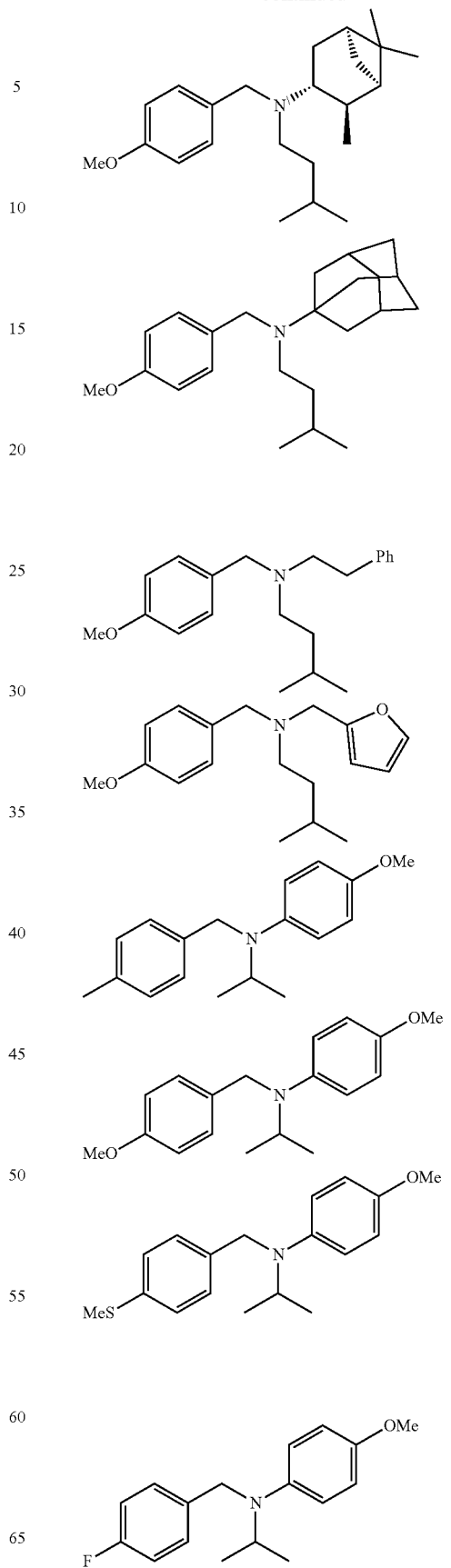

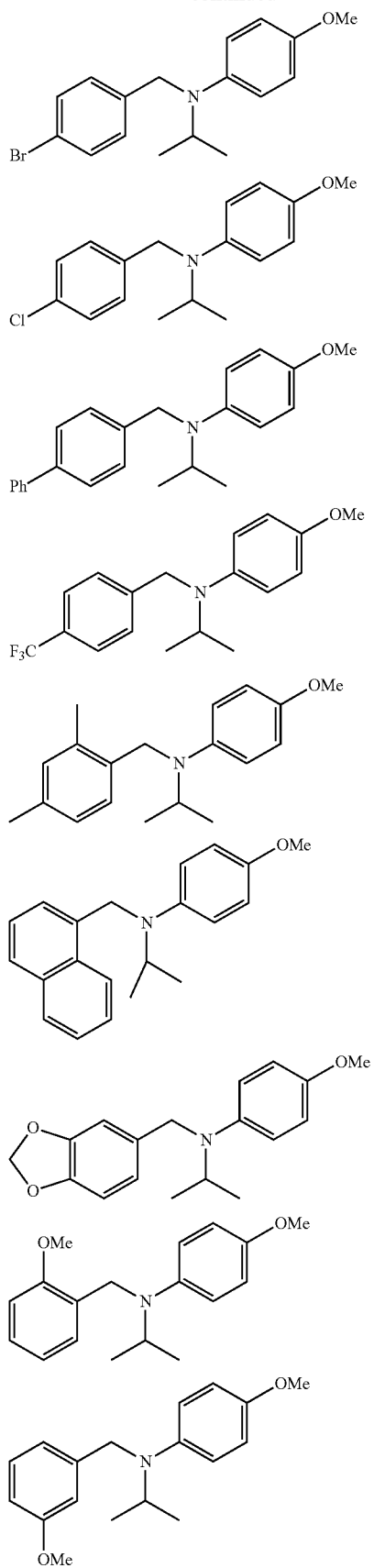
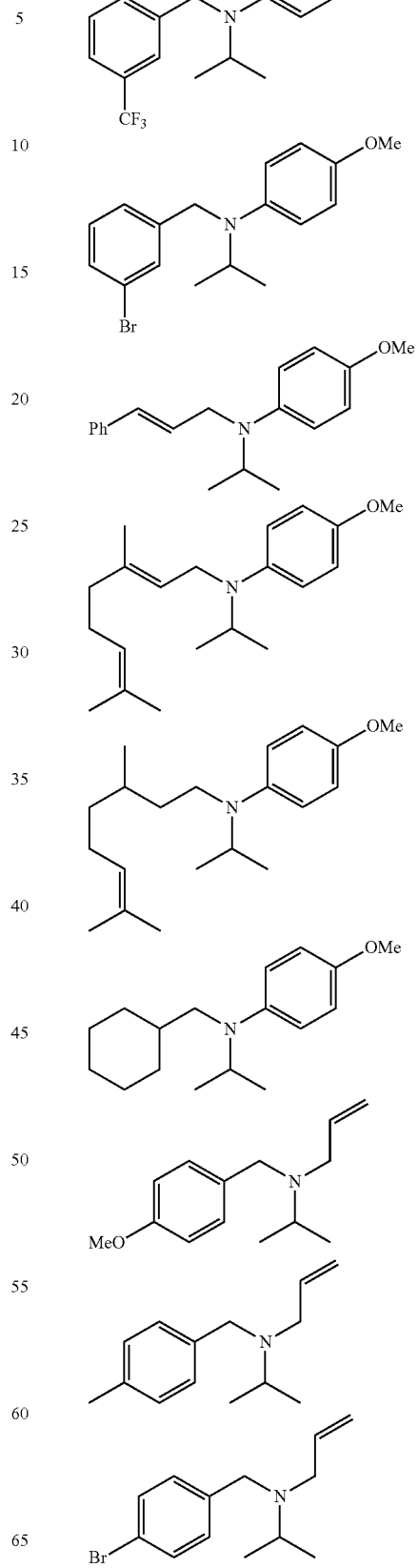

87
-continued
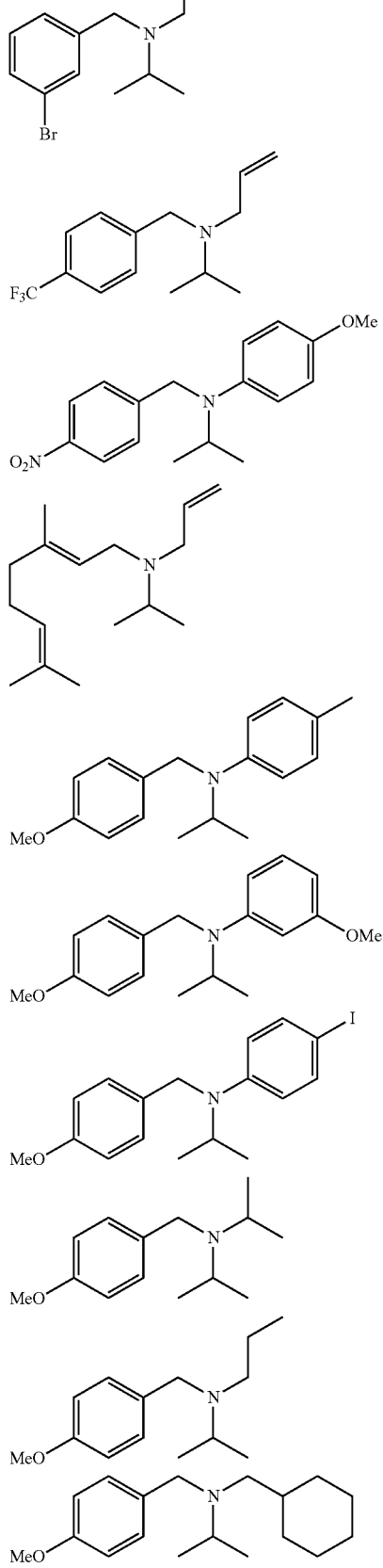
88
-continued
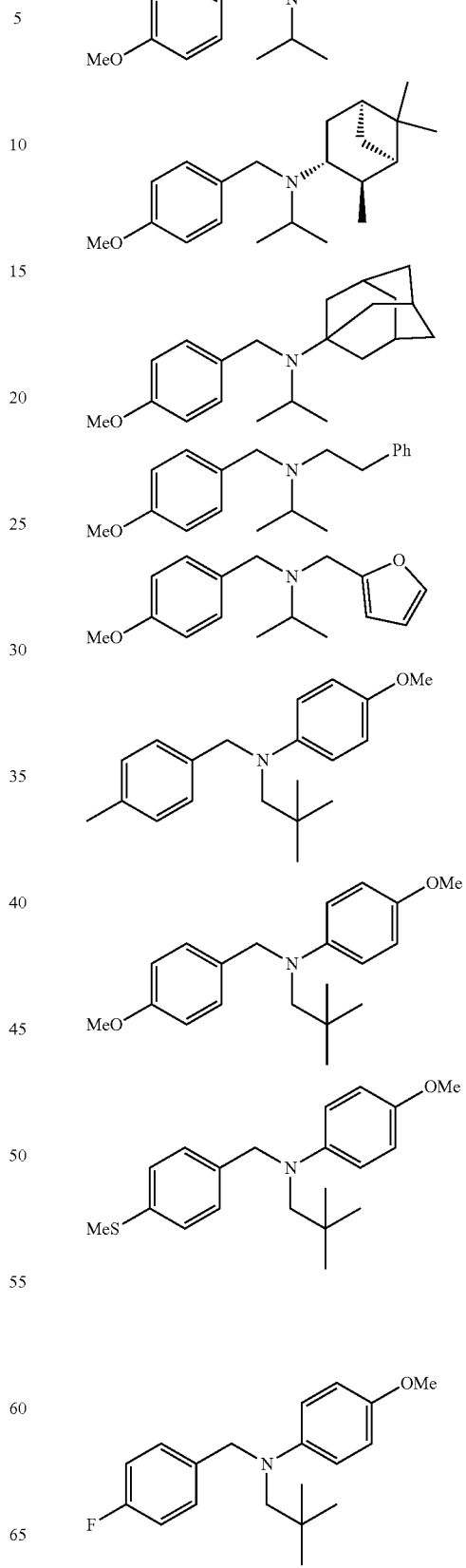

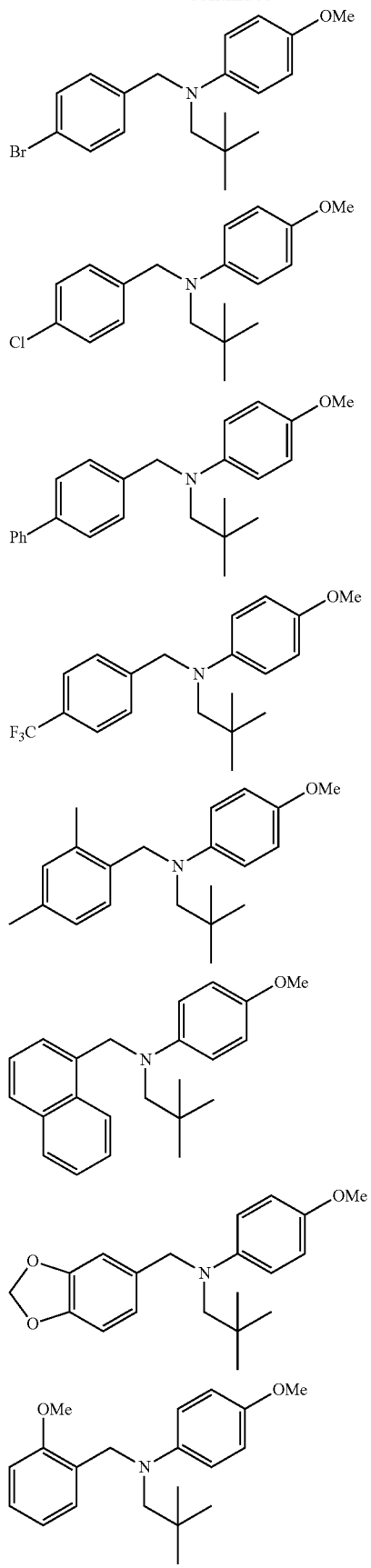
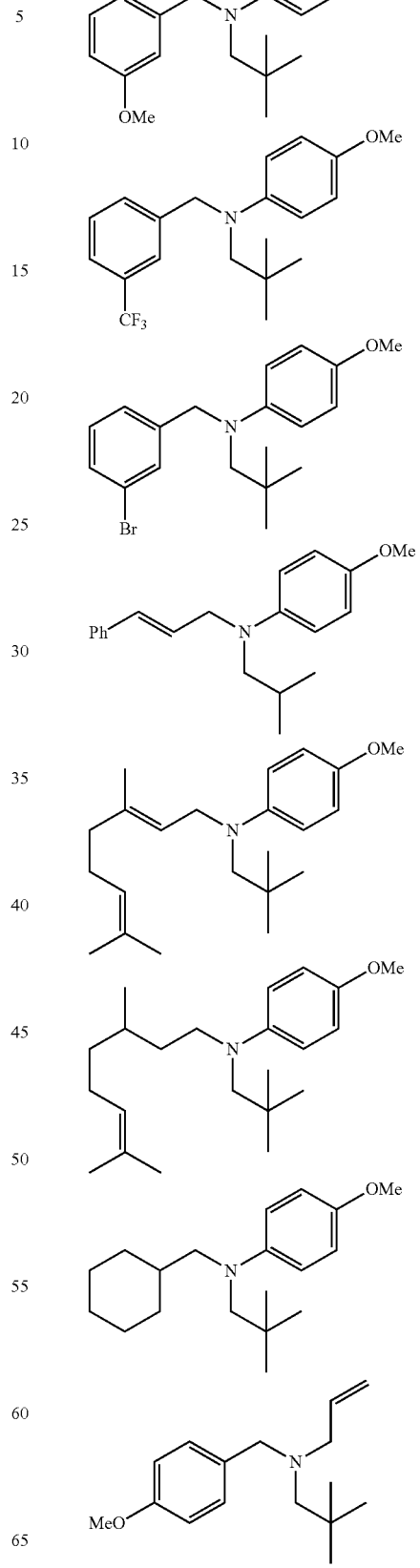

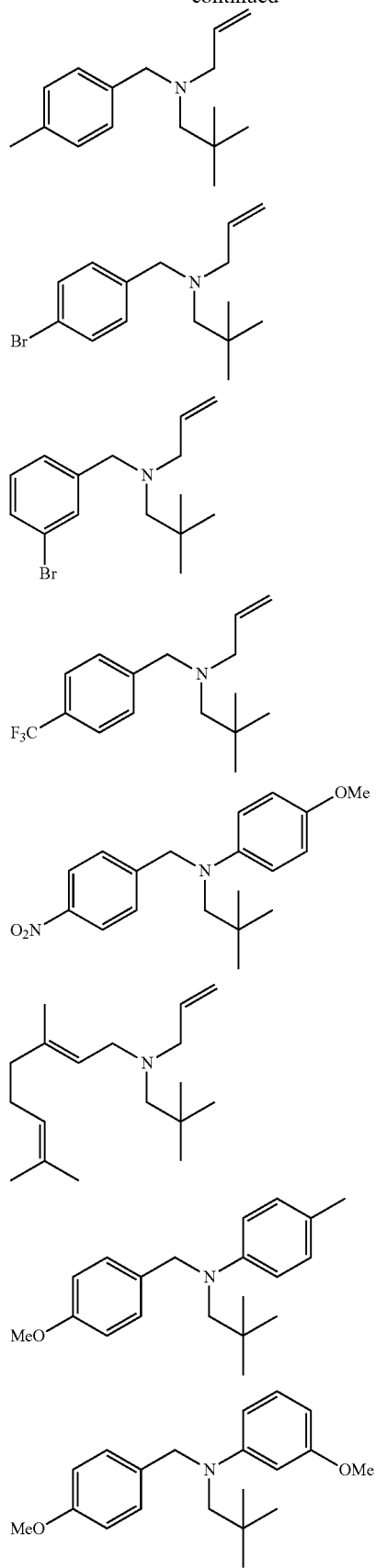
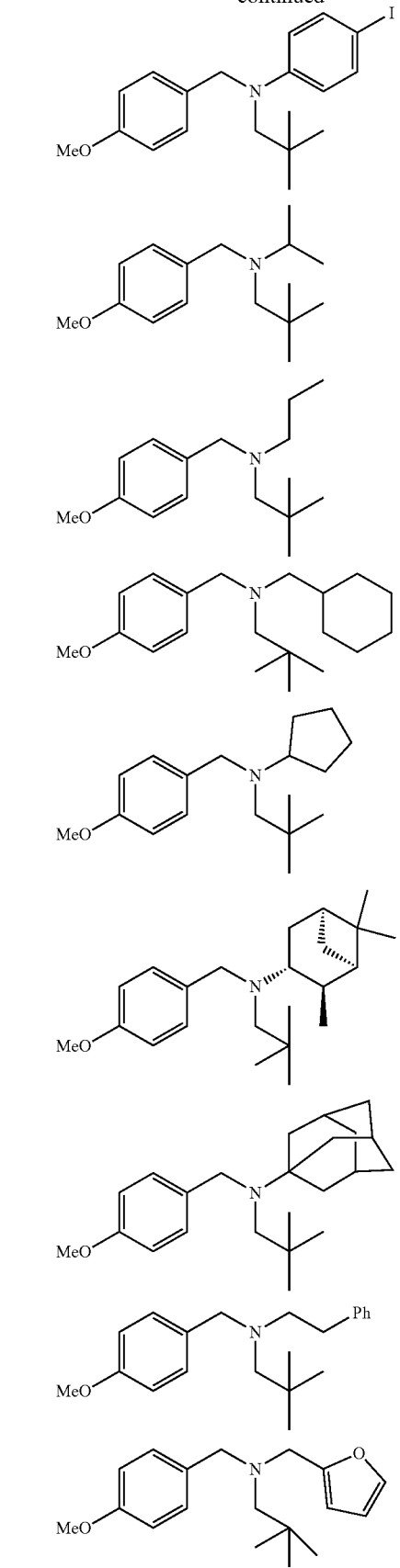

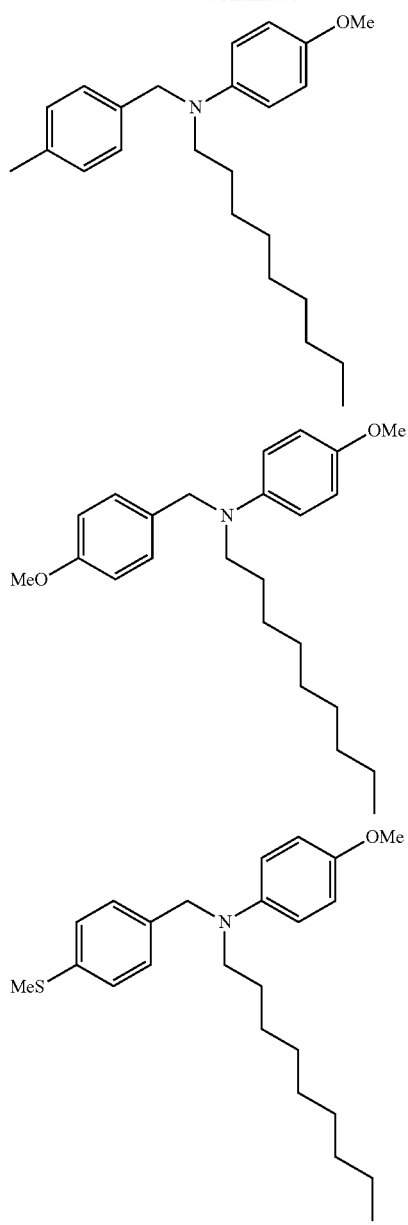
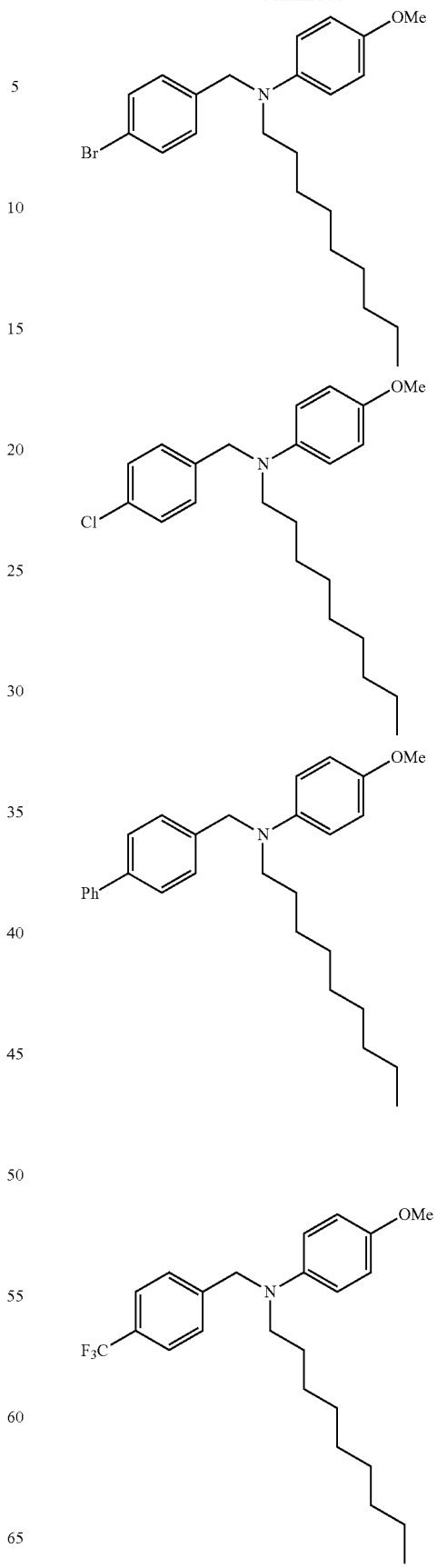

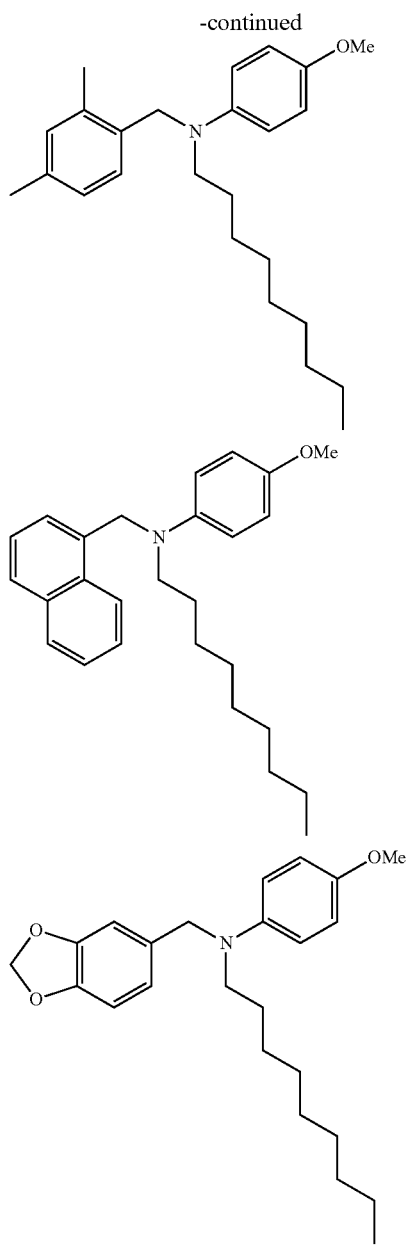
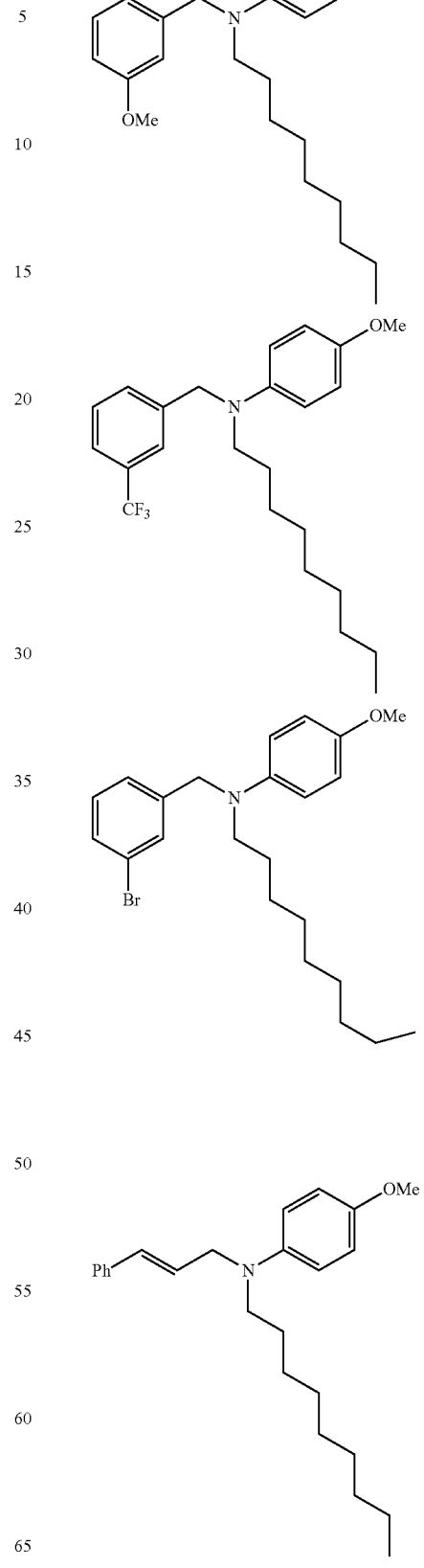

97
-continued
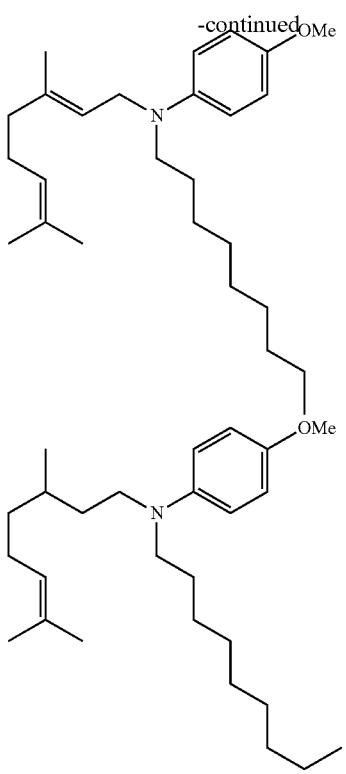
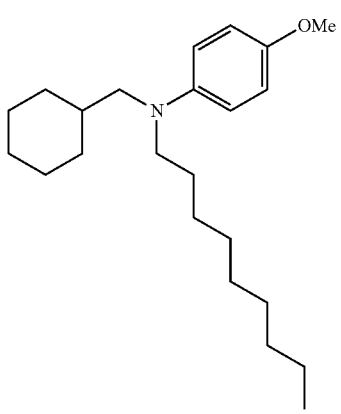
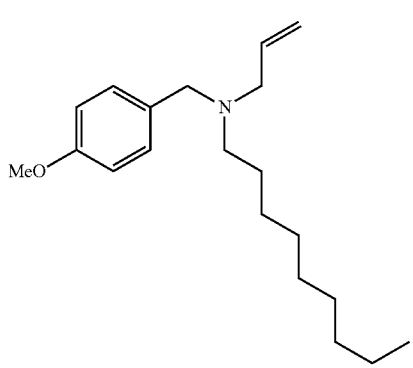
98
-continued
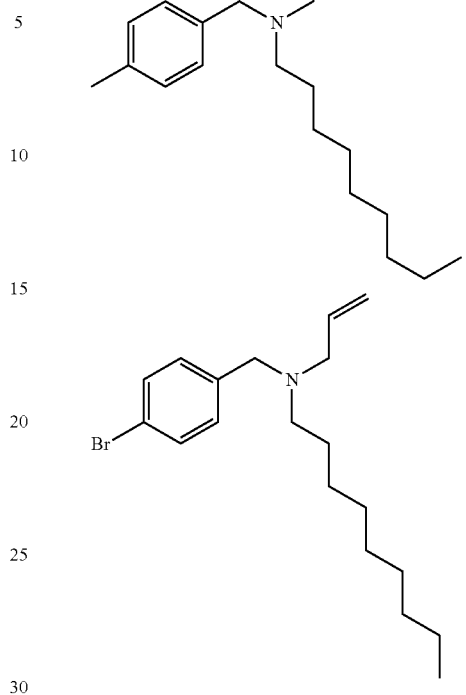
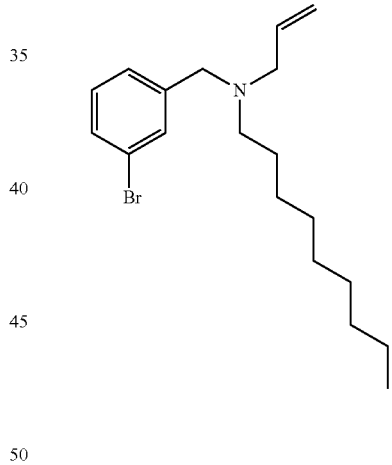
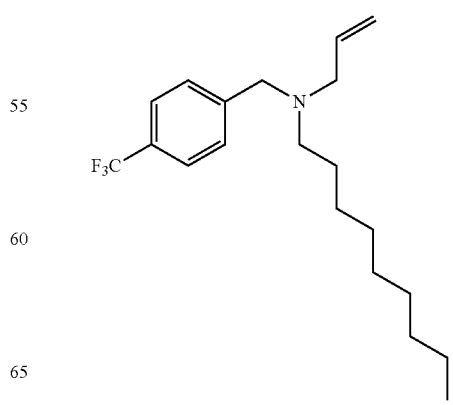

99
-continued
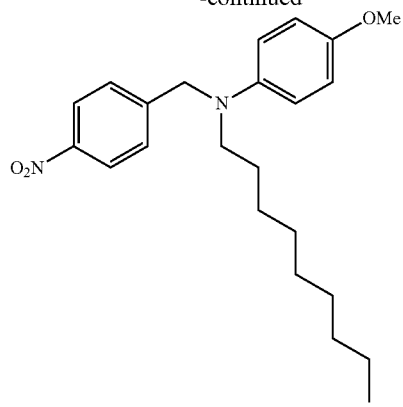
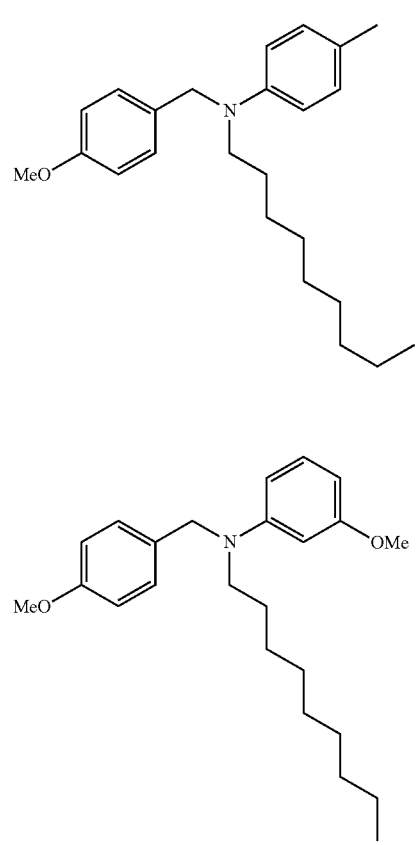
100
-continued
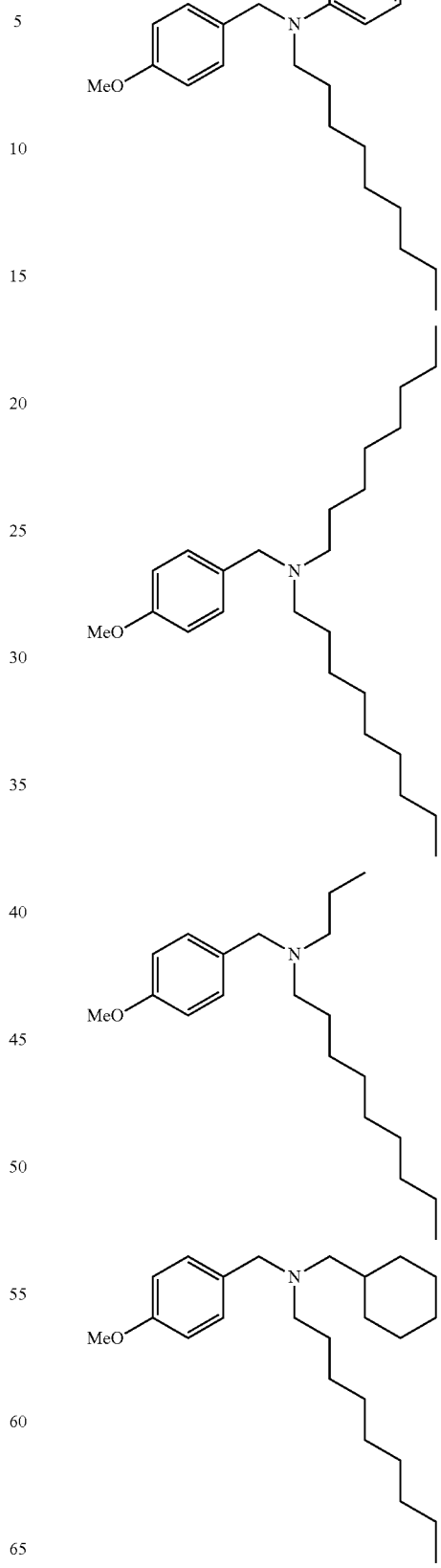

101
-continued
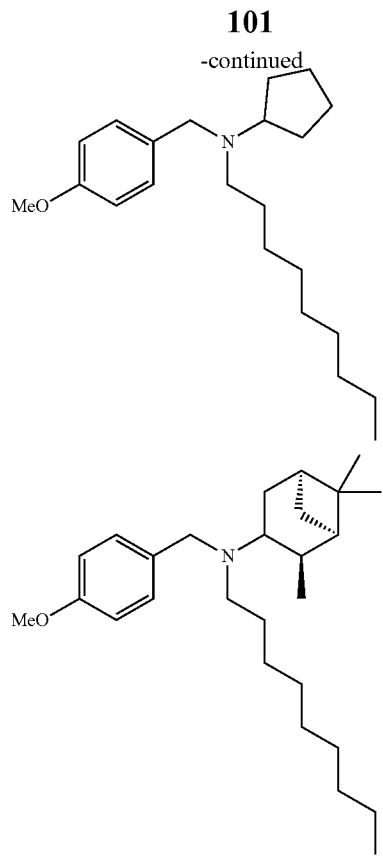
102
-continued
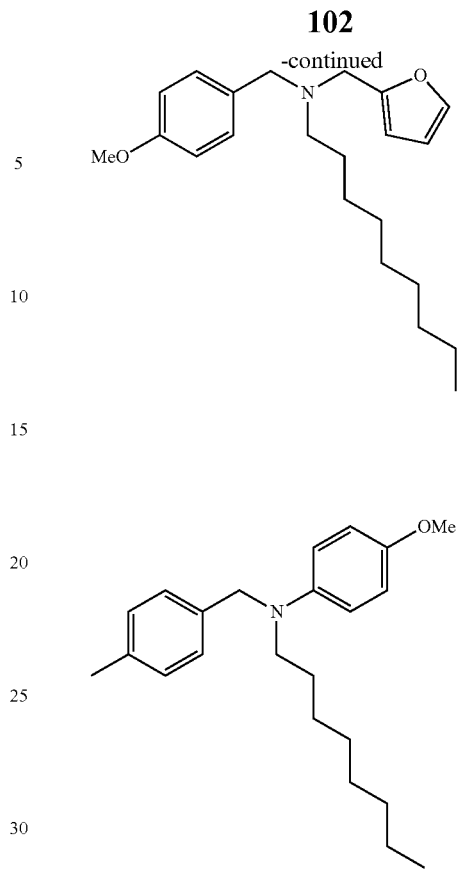
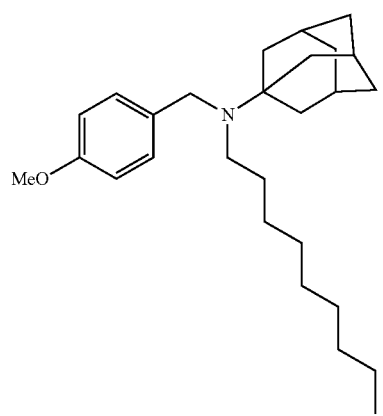
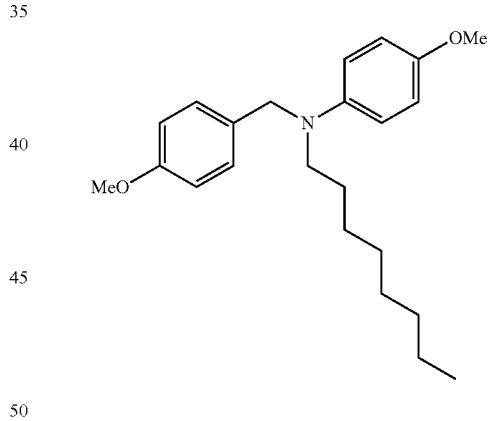
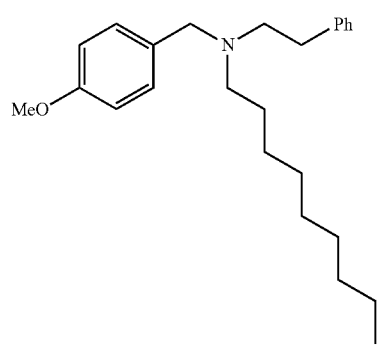
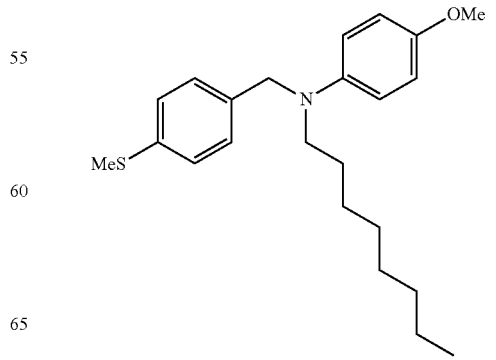

-continued
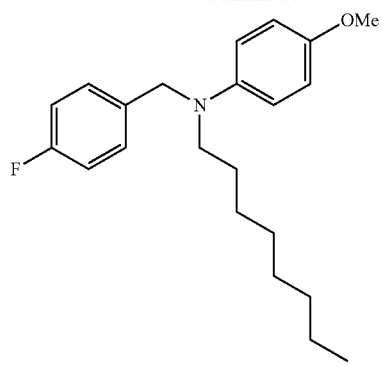
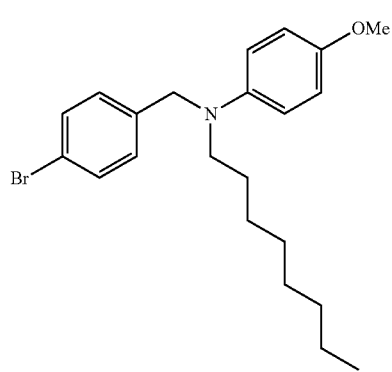
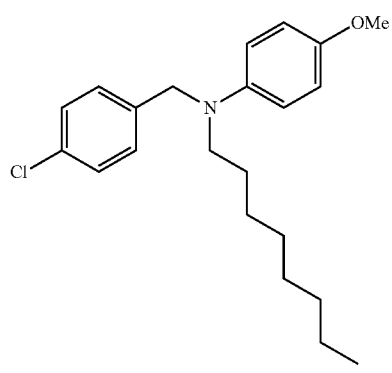
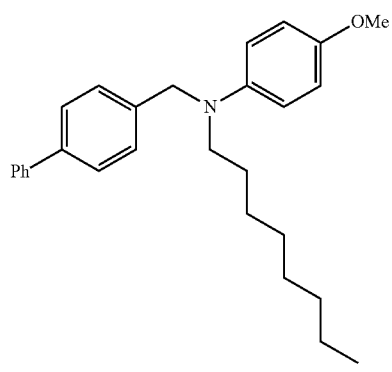
-continued
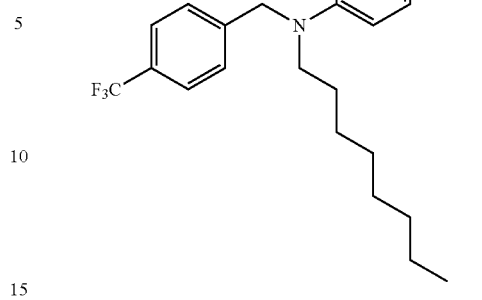
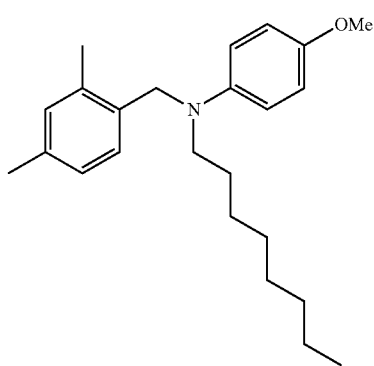
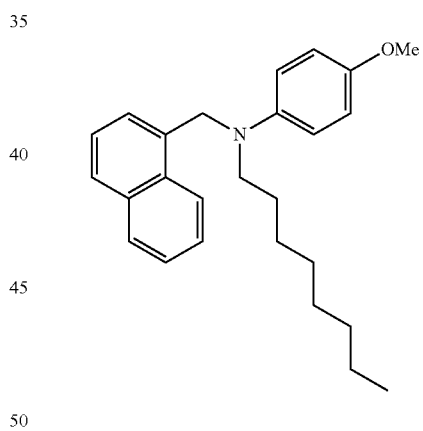
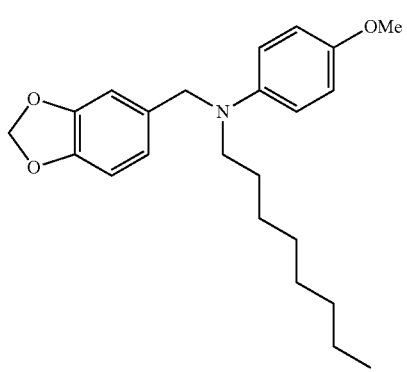

-continued
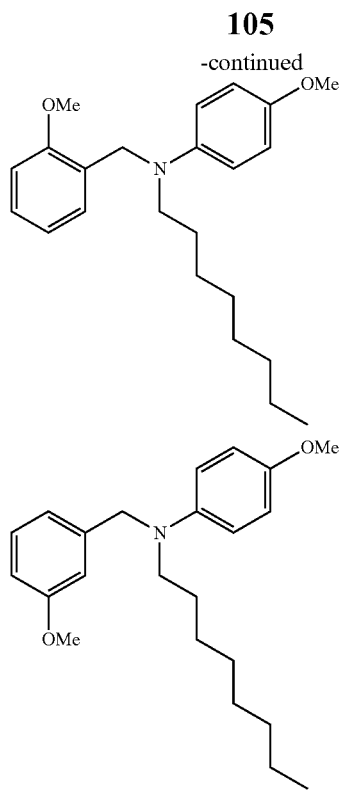
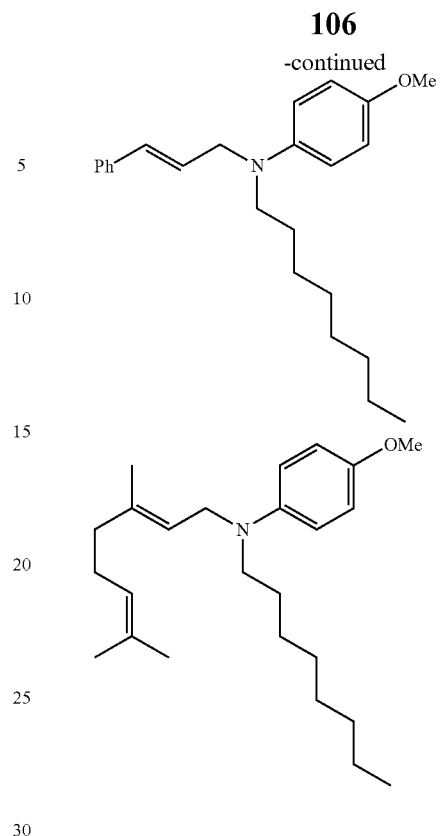
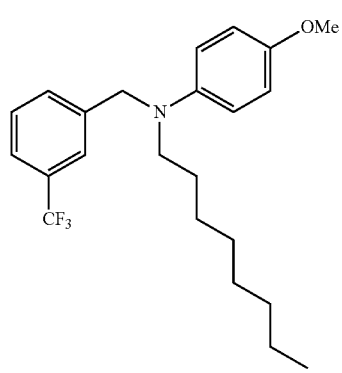
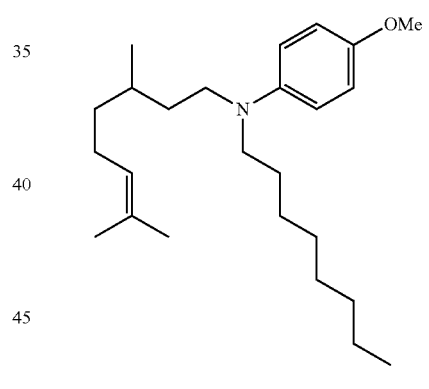
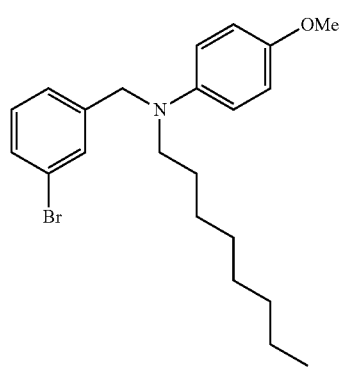
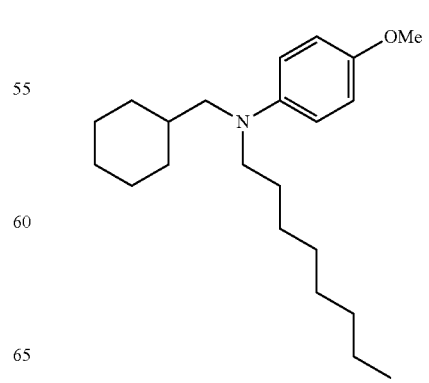

107
-continued
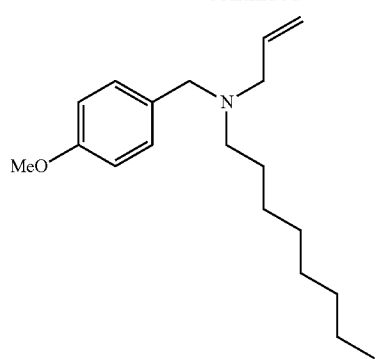
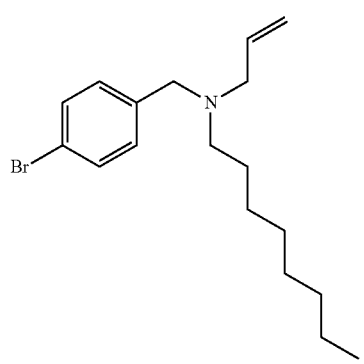
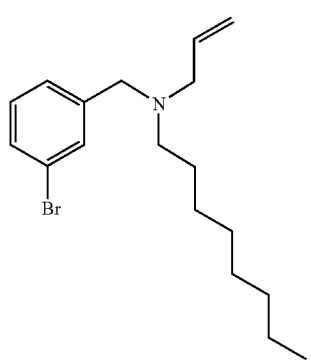
108
-continued
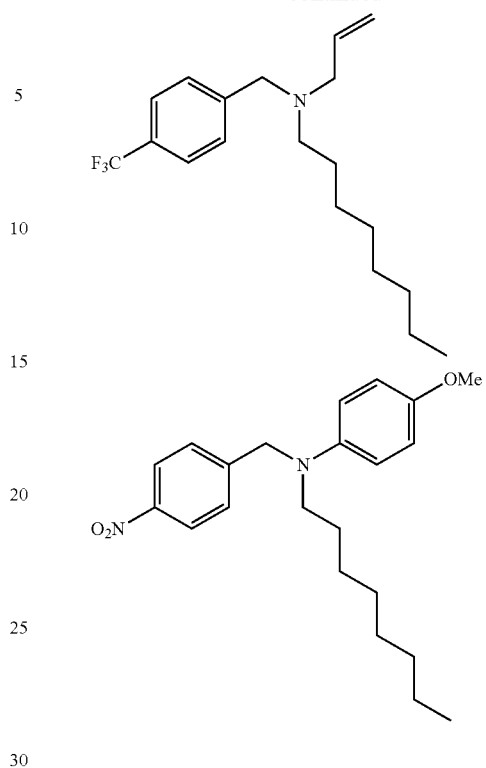
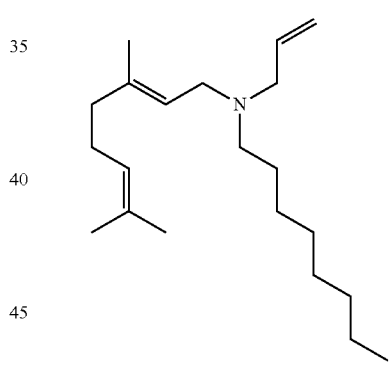
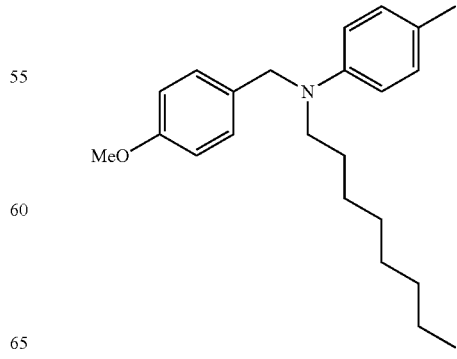

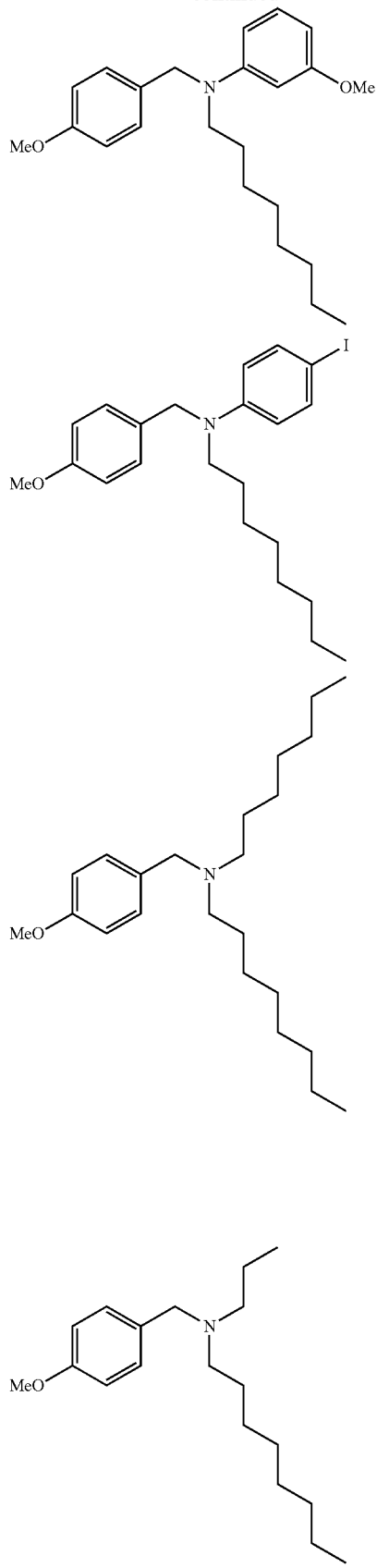
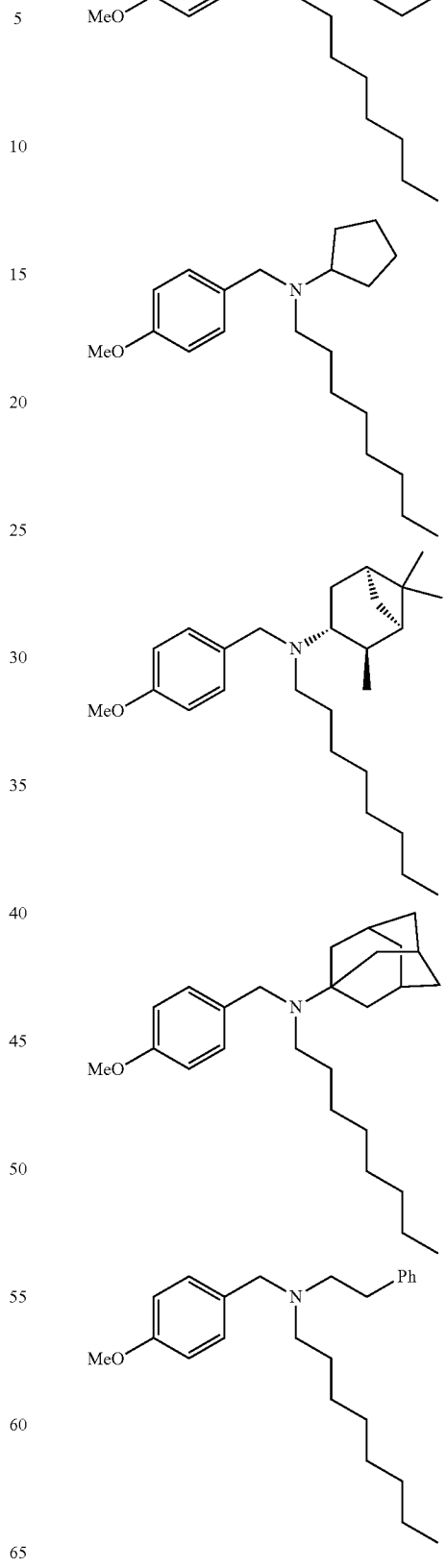

111
-continued
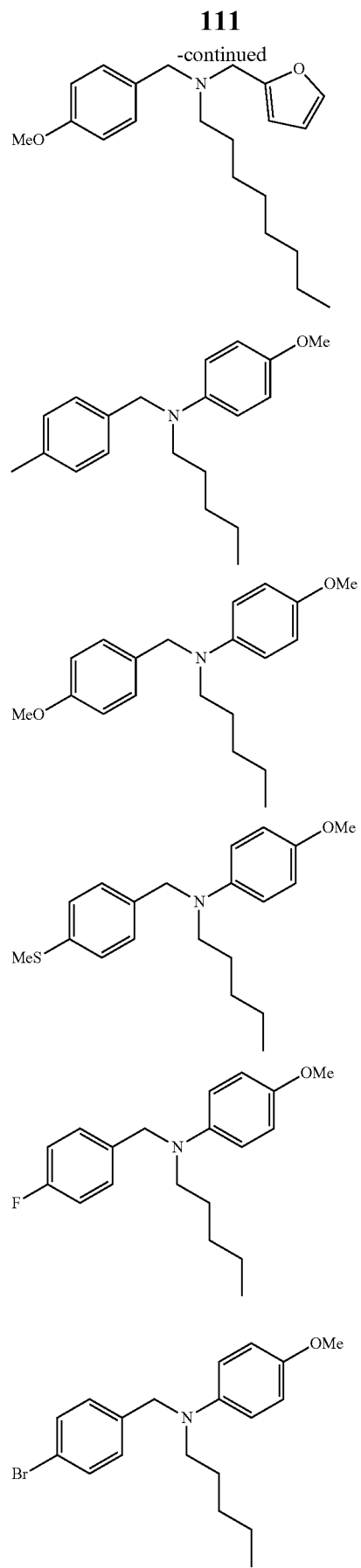
112
-continued
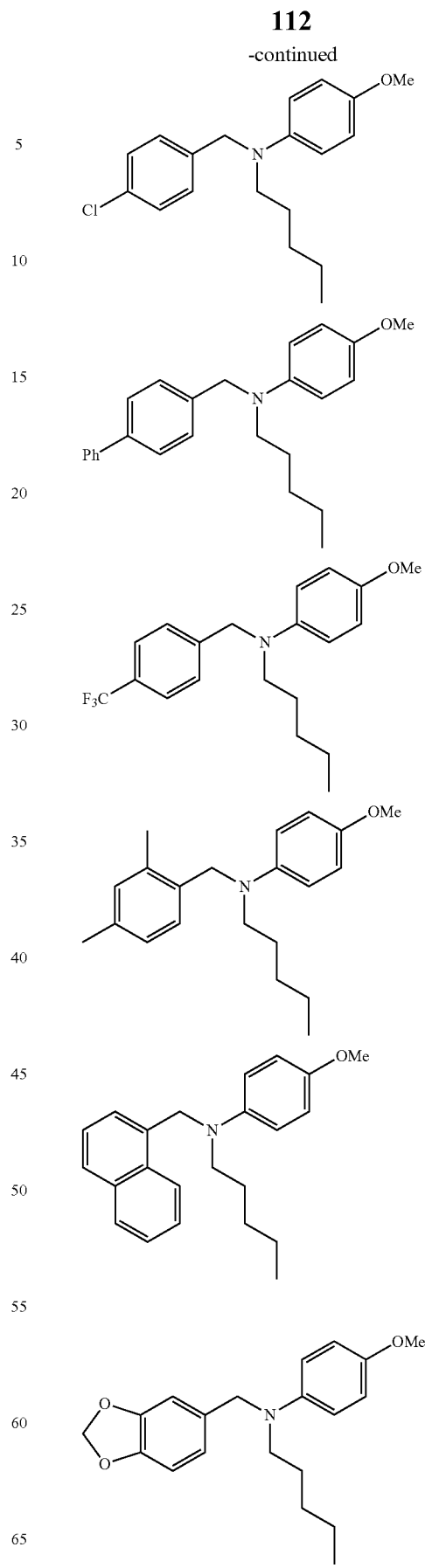

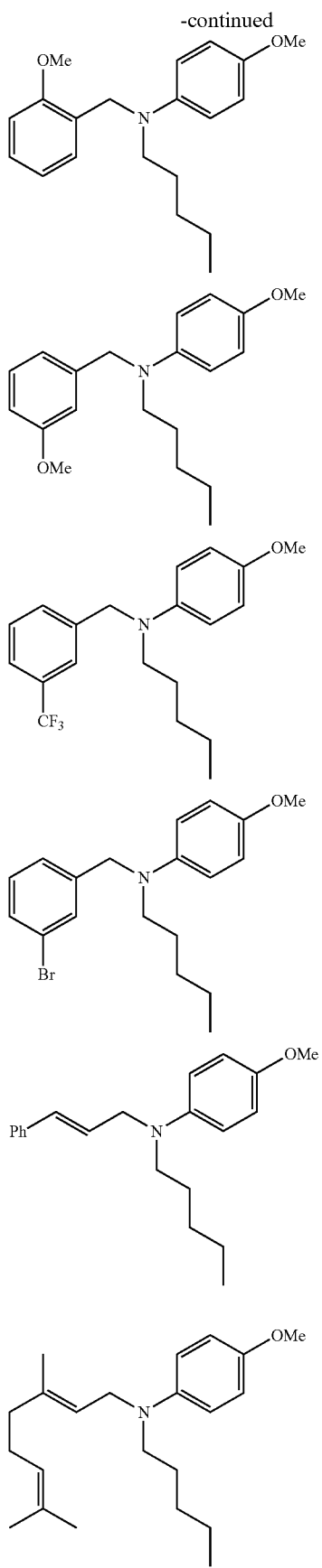
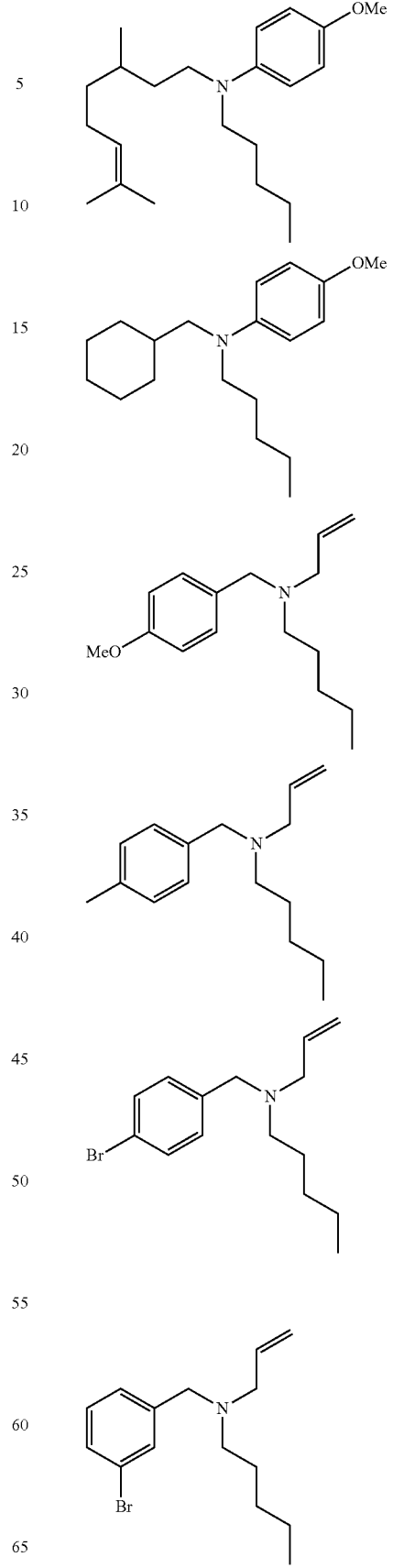

115
-continued
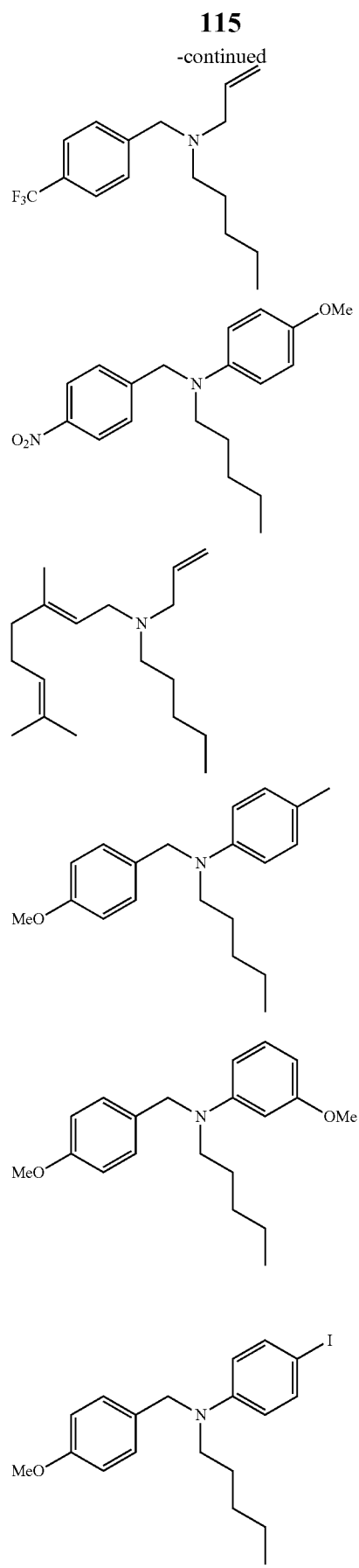
116
-continued
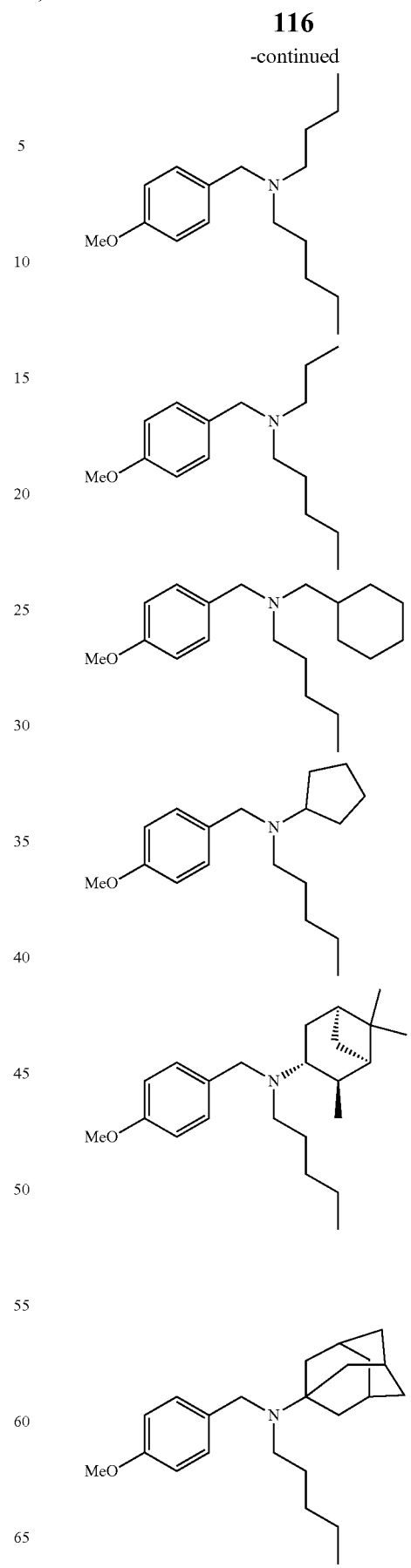

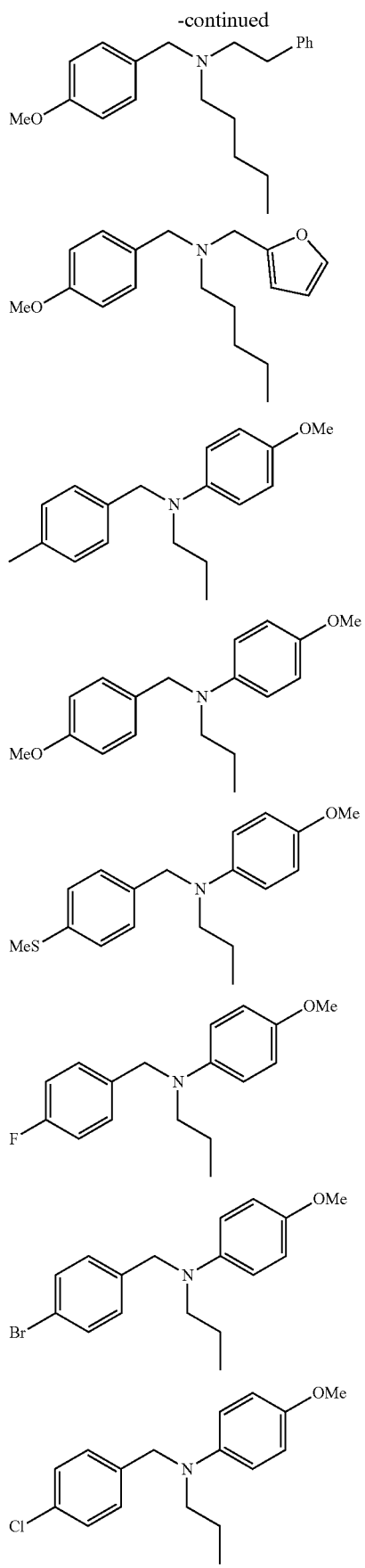
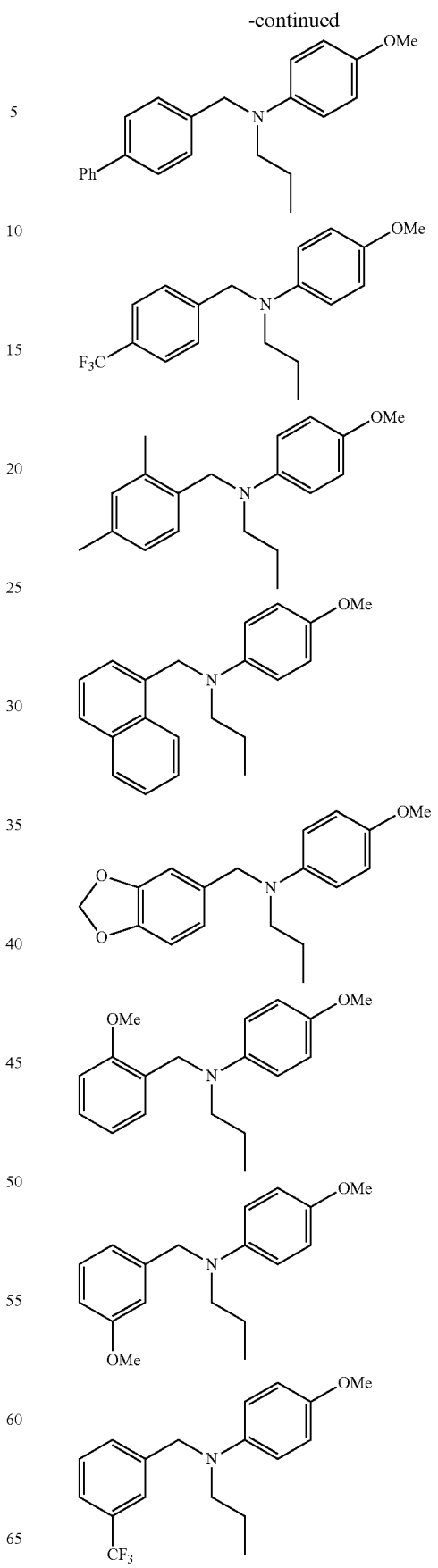

119
-continued
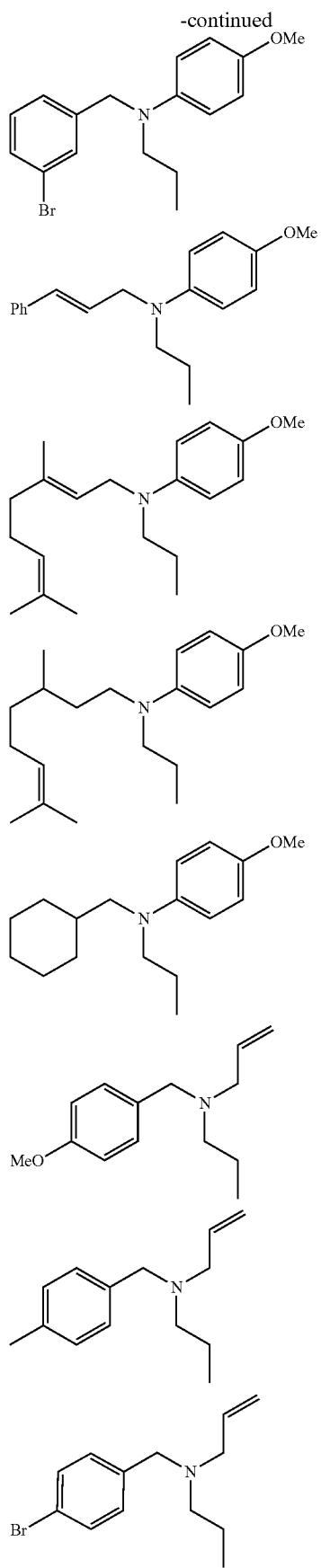
120
-continued
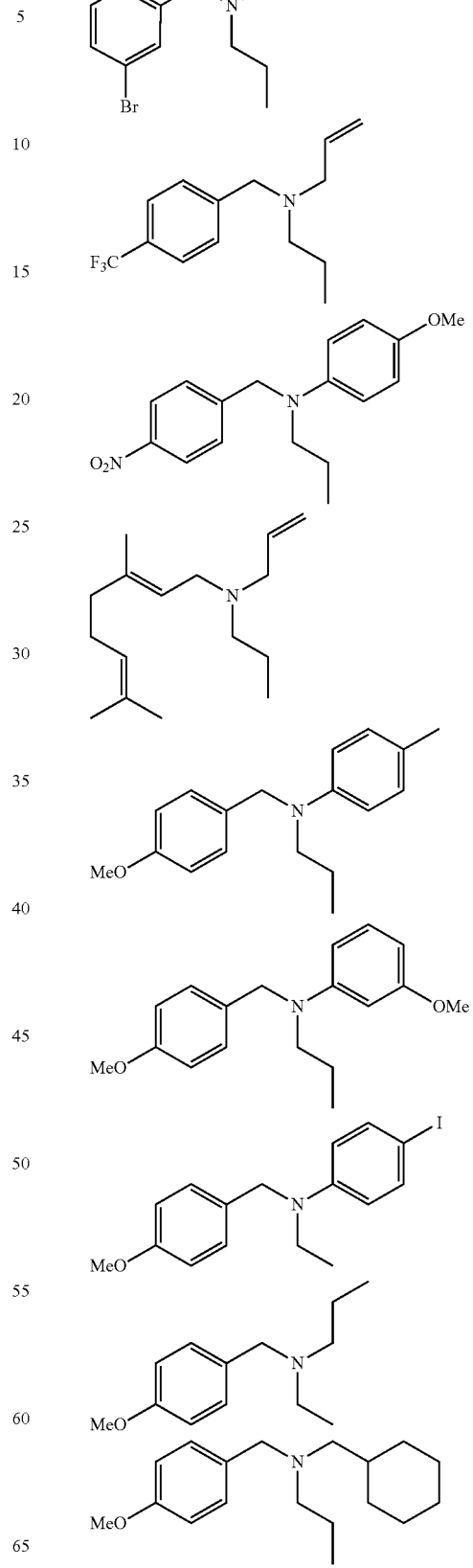

121
-continued
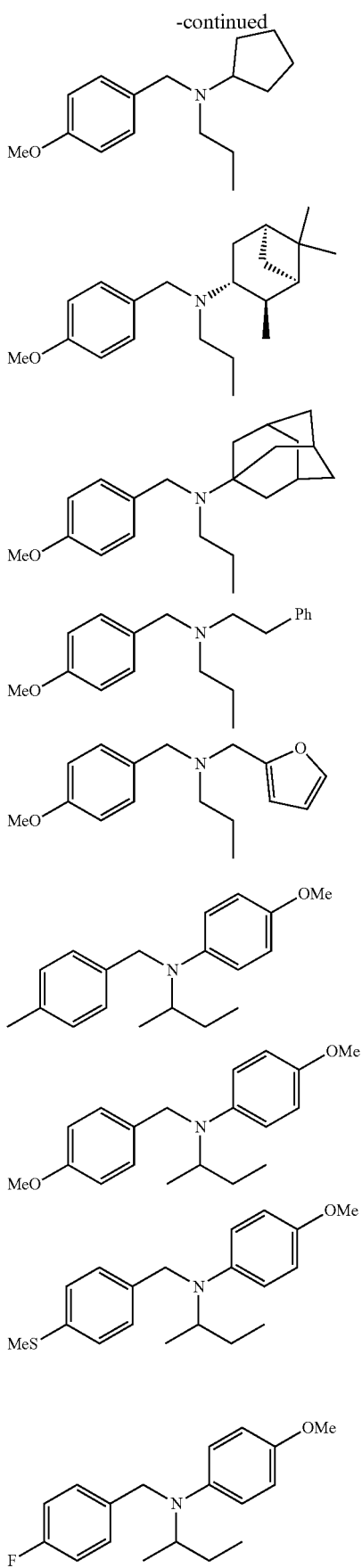
122
-continued
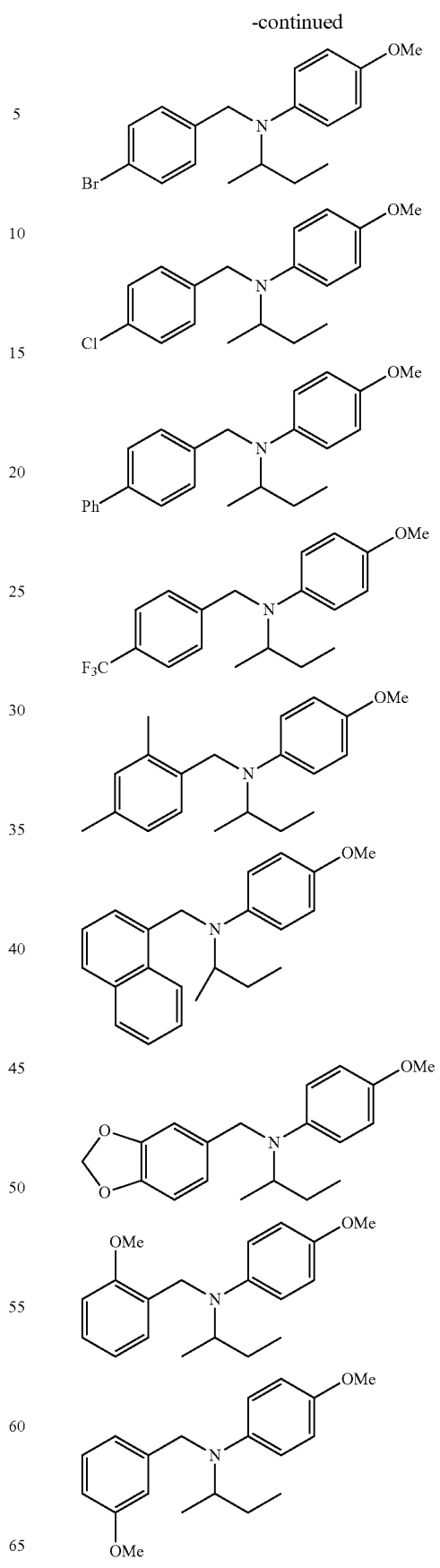

123
-continued
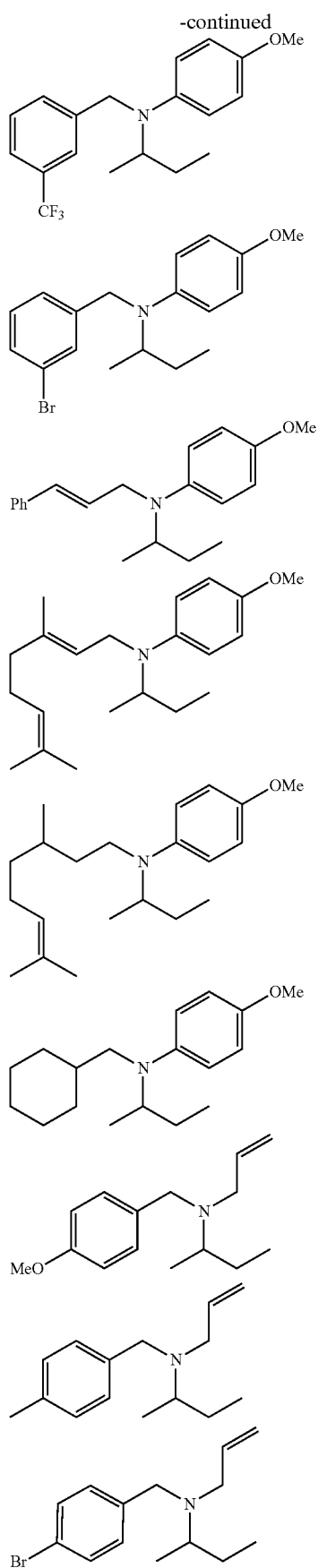
124
-continued
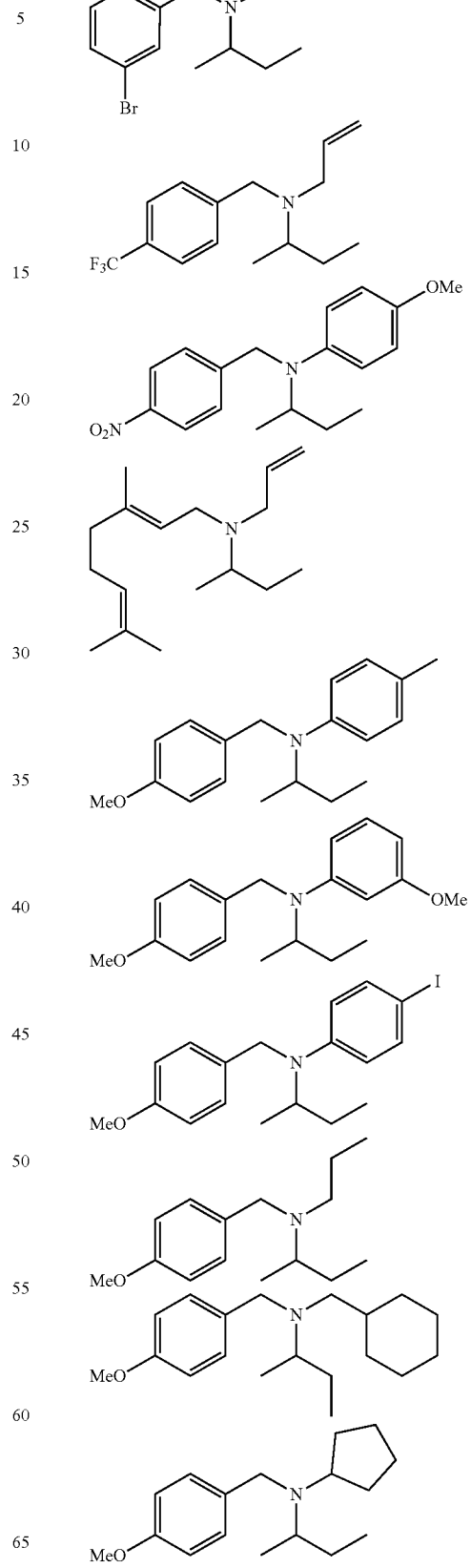

-continued
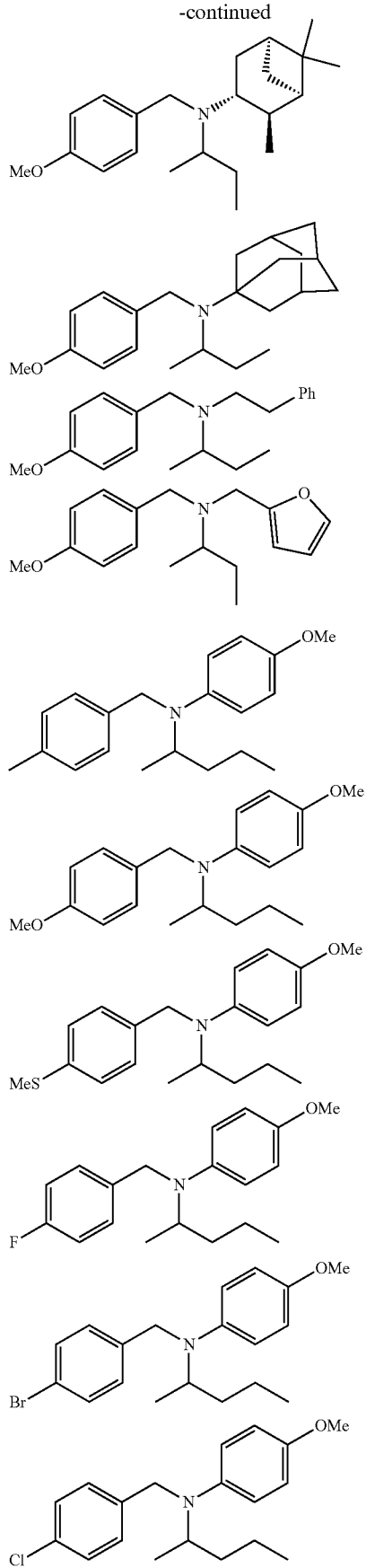
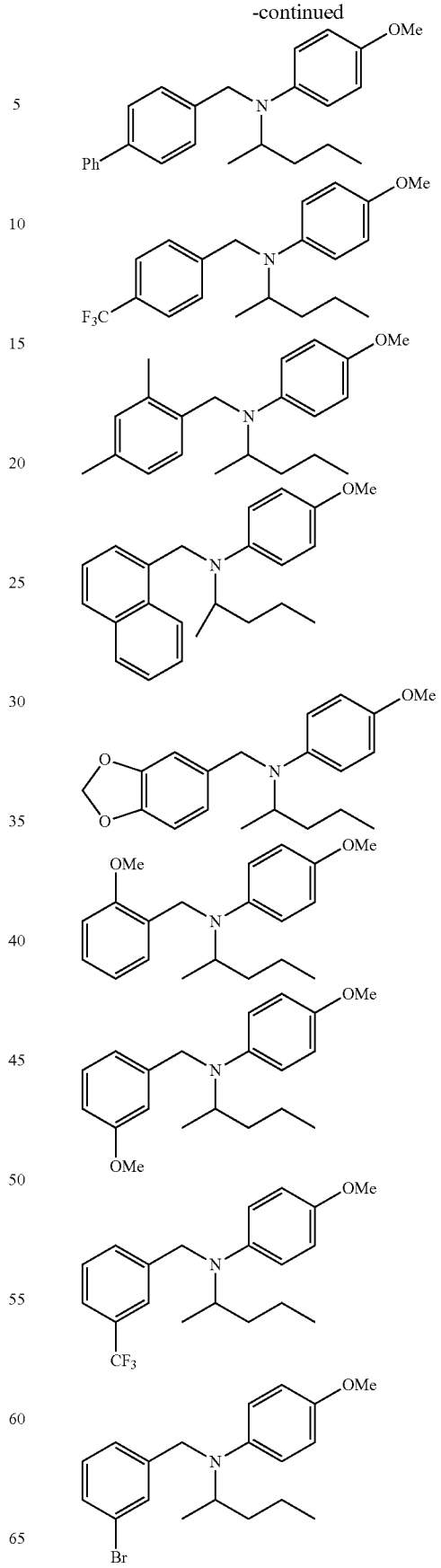

127
-continued
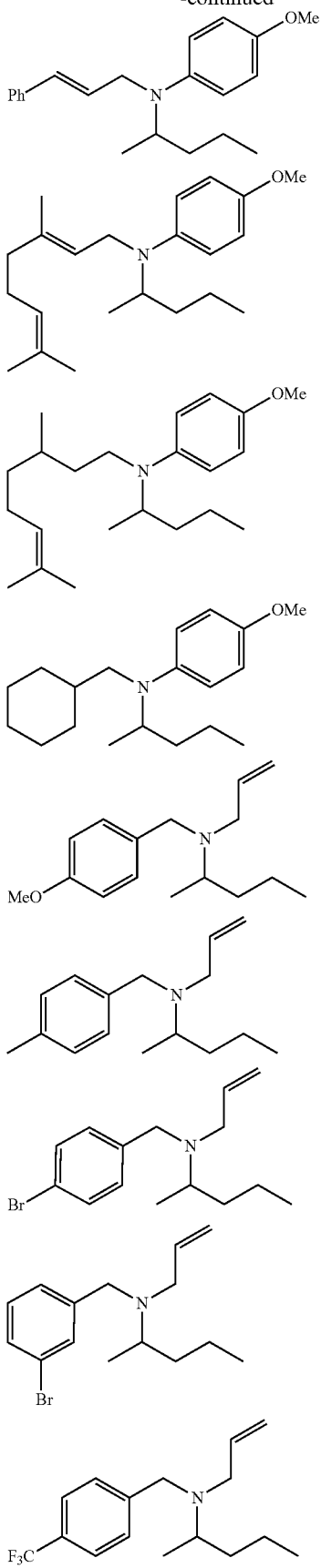
128
-continued
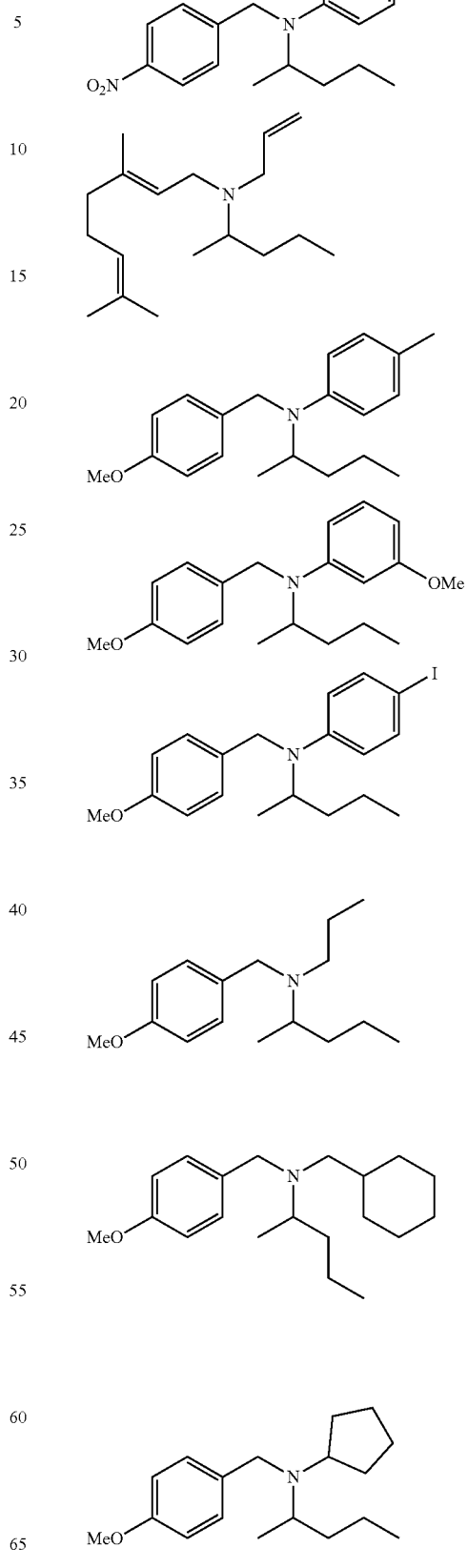

-continued

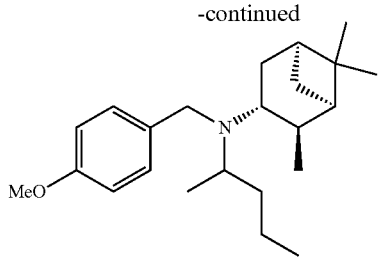

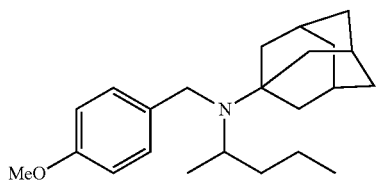

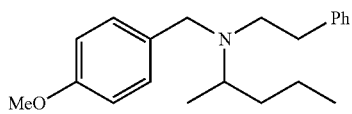

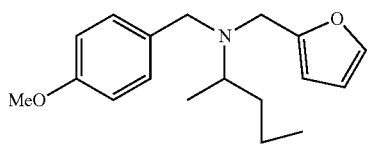

Amines having long carbon chains, especially tertiary, are of great industrial interest. They are used in the synthesis of chemical compounds, as surfactants (corrosion inhibitors, detergents, flotation agents, emollients, softeners, antistatics, germicides, insecticides, dispersant, anti-caking agents, emulsifiers, lubricants, water treatment agents, food additives, cosmetics, etc.).

Amines having long carbon chains, especially allylic, are fundamental elements of organic chemistry and their synthesis is an important industrial and synthetic objective. The allyl amine moiety can be found in natural products, but often, allylamine is converted into a range of products by functionalization, reduction or oxidation of the insaturation. Thus, amines can be used as raw materials for the synthesis of many compounds such as amino acids, alkaloids and carbohydrate derivatives.

Tertiary amines are important intermediates for the preparation of asymmetric quaternary ammonium salts of formula

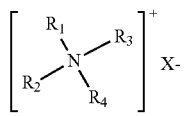

$R_1 \neq R_2 \neq R_3 \neq R_4$ = alkyl, phenyl
$C_1$ to $C_{10}$ alkyl or $C_3$ to $C_{10}$ cycloalky
X = Cl, Br, I, $BF_4$, $SbF_6$, $PF_5$, $ClO_4$ to access active agents whether for pharmaceutical or cosmetic use. They are used as surfactants, biocides for water treatment, flotation agent, petrol based detergent, corrosion inhibitors, processing rubber additives or emulsifiers for herbicides.

EXAMPLES

Example 1 Study of the Catalyst

TABLE 1

Tests with different iron catalysts

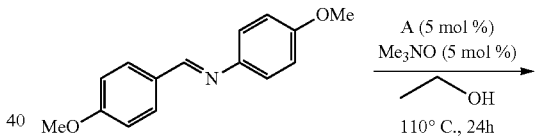

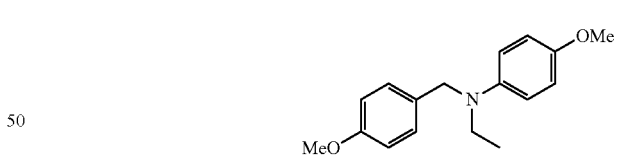

| Catalyst. | Additive | Ratio GC (starting/ reduction/alkylation) | Yield [%] |
|---|---|---|---|
| A | Me₃NO | 0/0/100 | 97 |
| B | — | 0/0/100 | 99 |

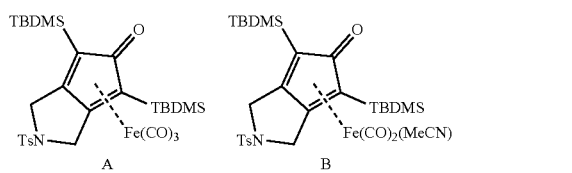

Example 2 Study of the Solvent

TABLE 2

Tests with different solvents

| Solvent | Temperature [° C.] | Ratio GC(starting/reduction/alkylation/dialkylation) |
|---|---|---|
| DCE/EtOH (svt/3 eq) | 80 | 18/72/10/0 |
| THF/EtOH (svt/3 eq) | 80 | 27/65/8/0 |
| THF/EtOH (1/1) | 80 | 15/1/79/5 |
| THF/EtOH (1/1) | 110 | 23/5/72/0 |
| CPME/EtOH (1/2) | 110 | 73/18/9/0 |

Example 3: Study of the Alcohol

TABLE 3

Study of several alcohols as alkylating agents

| Catalyst | Alcool | Ratio GC(starting/reduction/alkylation/dialkylation) | Yield [%] |
|---|---|---|---|
| B | ethylene glycol | 0/0/100/0 | 18 |
| B | ethanol | 0/0/100/0 | 99 |

Example 4: Aromatic Imines

TABLE 4

Exemplification with various aromatic aldehydes, substituted in the para position

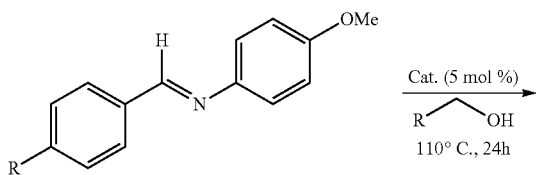

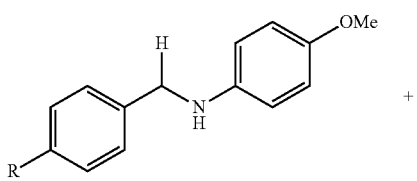

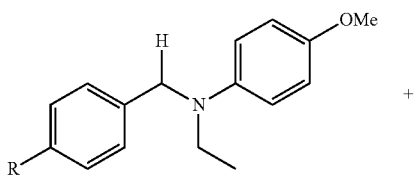

TABLE 4-continued

[Structure: N,N-diethyl-4-methoxyaniline]

| Product | Catalyst | Ratio GC (starting/reduction/ akylation/dialkylation) | Alkylation yield [%] |
|---|---|---|---|
| [N-benzyl-N-ethyl-4-methoxyaniline] | A/Me₃NO<br>B | 16/23/48/13<br>5/20/74/1 | 28<br>68 |
| [N-(4-methylbenzyl)-N-ethyl-4-methoxyaniline] | A/Me₃NO<br>B | 0/0/100/0<br>0/0/88/12 | 88<br>55 |
| [N-(4-methoxybenzyl)-N-ethyl-4-methoxyaniline] | A/Me₃NO<br>B | 0/0/100/0<br>0/0/100/0 | 97<br>99 |
| [N-(4-fluorobenzyl)-N-ethyl-4-methoxyaniline] | A/Me₃NO<br>B<br>B à 130° C. | 35/25/40/0<br>45/37/18/0<br>6/39/55/0 | 33<br>15<br>50 |
| [N-(4-bromobenzyl)-N-ethyl-4-methoxyaniline] | A/Me₃NO<br>B | 3/50/35/12<br>8/13/75/4 | 26<br>68 |
| [N-(4-chlorobenzyl)-N-ethyl-4-methoxyaniline] | A/Me₃NO<br>B | 48/33/19/0<br>0/0/86/14 | 12<br>74 |
| [N-(4-methylthiobenzyl)-N-ethyl-4-methoxyaniline] | A/Me₃NO<br>B | 34/19/43/4<br>0/0/84/16 | 54<br>85 |

TABLE 4-continued

| Product | Catalyst | Ratio GC (starting/reduction/akylation/dialkylation) | Alkylation yield [%] |
|---|---|---|---|
| 4-Ph-C6H4-CH2-N(Et)(4-MeO-C6H4) | A/Me3NO | — | — |
|  | B | 0/29/41/30 | 38 |
| 4-F3C-C6H4-CH(H)-N(Et)(4-MeO-C6H4) | B | 36/39/25/0 | 20 |

TABLE 5

Exemplification with various aromatic aldehydes

R—C6H4—CH=N—C6H4—OMe  →(Cat. (5 mol %), EtOH, 110° C., 24 h)→

R—C6H4—CH2—NH—C6H4—OMe  +

R—C6H4—CH2—N(Et)—C6H4—OMe  +

Et2N—C6H4—OMe

| Product | Catalyst | Ratio GC (starting/reduction/akylation/dialkylation) | Alkylation yield [%] |
|---|---|---|---|
| 2,4-Me2-C6H3-CH2-N(Et)(4-MeO-C6H4) | A/Me3NO | — | — |
|  | B | 19/3/78/0 | 70 |
| 1-Naphthyl-CH2-N(Et)(4-MeO-C6H4) | A/Me3NO | — | 70 |
|  | B | — | 72 |

TABLE 5-continued
| Structure | Conditions | Ratio | Yield |
|---|---|---|---|
| 2-OMe-C6H4-CH(H)-N(Et)-C6H4-OMe | A/Me₃NO | 0/0/83/17 | 49 |
| | B | 0/0/72/28 | 55 |
| 3-MeO-C6H4-CH(H)-N(Et)-C6H4-OMe | A/Me₃NO | 0/0/92/8 | 78 |
| | B | 0/0/90/10 | 70 |
| 3,4-methylenedioxy-C6H3-CH(H)-N(Et)-C6H4-OMe | A/Me₃NO | — | — |
| | B | 5/0/90/5 | 78 |
| 3-Br-C6H4-CH(H)-N(Et)-C6H4-OMe | A/Me₃NO | — | — |
| | B | 0/31/29/40 | 21 |
| 3-F3C-C6H4-CH(H)-N(Et)-C6H4-OMe | B | 0/0/15/85 | 10 |
Example 5: Allylated Imines
TABLE 6
Exemplification with various conjugated aldehydes
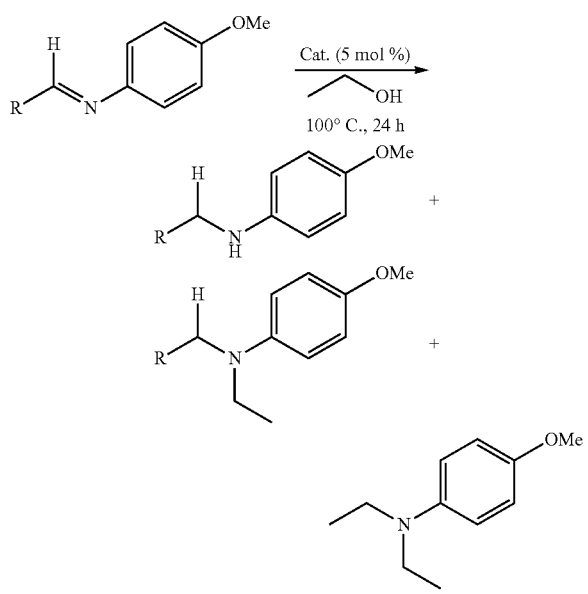

TABLE 6-continued

| Product | Catalyst | Ratio GC (starting/reduction/akylation/dialkylation) | Alkylation yield [%] |
|---|---|---|---|
| (cinnamyl-N(Et)-C6H4-OMe) | A/Me₃NO B | — | — 67 |
| (geranyl-N(Et)-C6H4-OMe) | A/Me₃NO B | — | 48 30 |

Example 6: Alkylated Imines

TABLE 7

Exemplification with various aliphatic aldehydes

R-CH=N-C6H4-OMe →(Cat. (5 mol %), EtOH, 110° C., 24 h)→ R-CH2-NH-C6H4-OMe + R-CH2-N(Et)-C6H4-OMe + Et2N-C6H4-OMe

| Product | Catalyst | Ratio GC (starting/reduction/akylation/dialkylation) | Alkylation yield [%] |
|---|---|---|---|
| (citronellyl-N(Et)-C6H4-OMe) | A/Me₃NO B | — 0/0/78/22 | 52 54 |

TABLE 7-continued
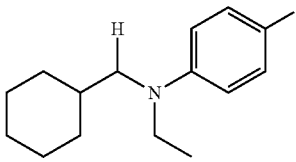
| | | | |
|---|---|---|---|
| A/Me₃NO B | — | — | |
| | 0/40/17/43 | 14 | |
| | | 10 | |
Example 7: Aromatic Imines
TABLE 8
Exemplification with various aromatic amines
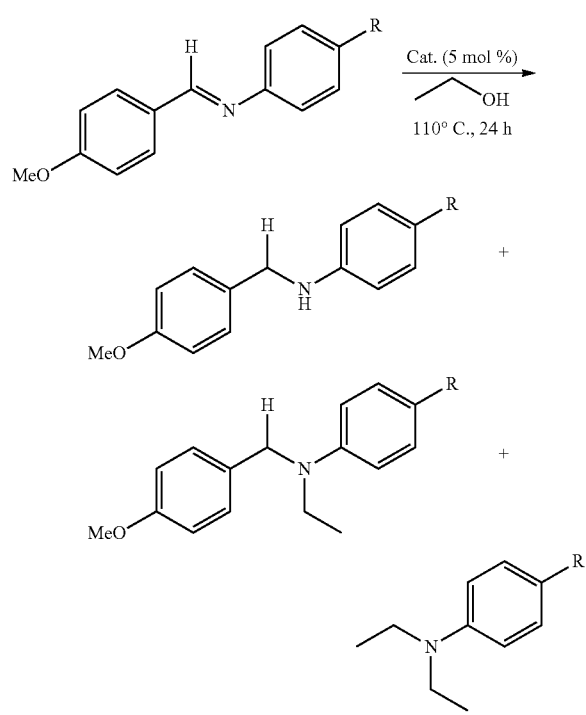
| Product | Ratio GC (starting/reduction/ akylation/dialkylation) | Alkylation yield [%] |
|---|---|---|
| (MeO-C₆H₄-CH₂-N(Et)-C₆H₅) | 0/58/42/0 | 30 |
| (MeO-C₆H₄-CH₂-N(Et)-C₆H₄-Me) | 0/10/90/0 | 88 |

TABLE 8-continued
| Product | Ratio GC | Alkylation yield [%] |
|---|---|---|
| 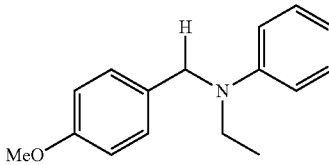 | 45/37/18/0 | 12 |
| | 0/34/36/30 | 18 |
TABLE 9
Exemplification with various aliphatic amines
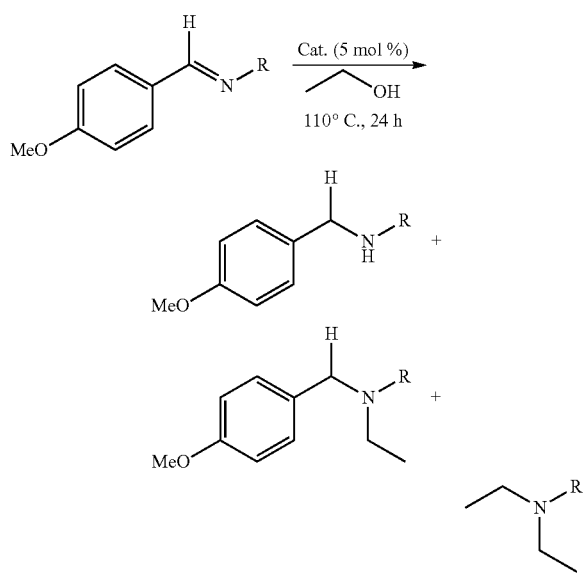
| Product | Ratio GC (starting/reduction/ akylation/dialkylation) | Alkylation yield [%] |
|---|---|---|
| 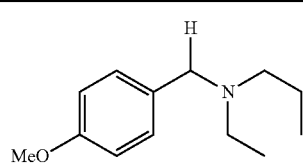 | 0/0/100/0 | 85 |
| 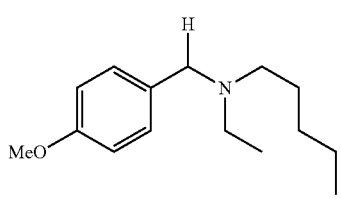 [SMILES: CCCCCN(CC)Cc1ccc(OC)cc1] | 0/0/100/0 | 85 |
| 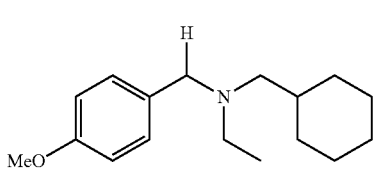 [SMILES: CCN(Cc1ccc(OC)cc1)CC1CCCCC1] | 0/0/67/33 | 51 |

TABLE 9-continued

| Structure | Ratio | Yield |
|---|---|---|
| 4-MeO-C6H4-CH(H)-N(Et)-cyclopentyl | 0/0/100/0 | 75 |
| 4-MeO-C6H4-CH(H)-N(Et)-pinanyl | 0/0/100/0 | 47 |
| 4-MeO-C6H4-CH(H)-N(Et)-adamantyl | 39/9/52/0 | 18 |

Example 8: Allylated Imines

TABLE 10

Exemplification with various substituted aromatic amines $$\text{R}-\text{C}_6\text{H}_4-\text{CH}=\text{N}-\text{CH}_2\text{CH}=\text{CH}_2 \xrightarrow[\text{110° C., 24 h}]{\text{Cat. (5 mol \%)}\atop \text{EtOH}}$$

R–C6H4–CH(H)–NH–allyl +

R–C6H4–CH(H)–N(Et)–allyl +

Et2N–allyl

| Product | Catalyst | Ratio GC (starting/reduction/alkylation/dialkylation) | Alkylation yield [%] |
|---|---|---|---|
| Ph-CH(H)-N(Et)-allyl | A/Me3NO | — | — |
|  | B | 0/0/100/0 | 57 |
| 4-MeO-C6H4-CH(H)-N(Et)-allyl | A/Me3NO | — | — |
|  | B | 0/0/100/0 | 85 |

TABLE 10-continued

| Structure | Conditions | Ratio | Yield |
|---|---|---|---|
| 4-methylbenzyl-N-ethyl-N-allylamine | A/Me₃NO / B | — / Incomplete conversion | — / 38 |
| 4-bromobenzyl-N-ethyl-N-allylamine | A/Me₃NO / B | — / 0/0/100/0 | — / 88 |
| 2-bromobenzyl-N-ethyl-N-allylamine | A/Me₃NO / B | — / 0/0/100/0 | — / 72 |
| 4-trifluoromethylbenzyl-N-ethyl-N-allylamine | A/Me₃NO / B | — / 0/0/100/0 | — / 55 |
| 4-(methoxycarbonyl)benzyl-N-ethyl-N-allylamine | A/Me₃NO / B | — / 0/8/92/0 | — / 76 |
| 4-nitrobenzyl-N-ethyl-N-allylamine  B53 | B | 0/0/100/0 | 15 |

TABLE 11

Exemplification with various allylic or aliphatic amines

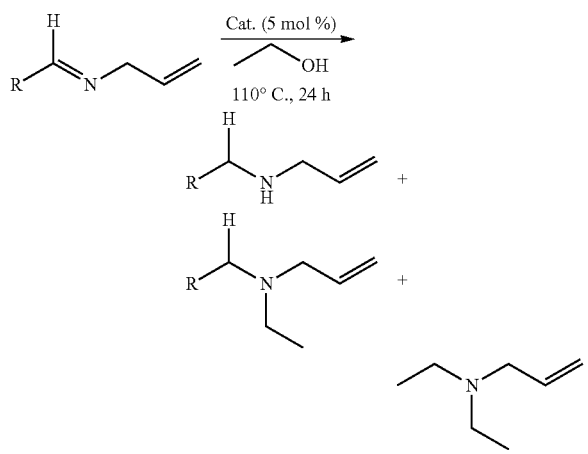

TABLE 11-continued
| Product | Catalyst | Ratio GC (starting/reduction/akylation/dialkylation) | Alkylation yield [%] |
|---|---|---|---|
| 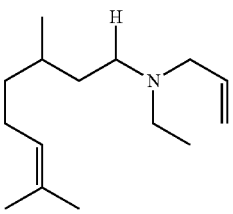 [SMILES: C=CCN(CC)CCC(C)CCC=C(C)C] | B | 0/0/100/0 | 22 |
Example 9 Other Imines
TABLE 12
Exemplification with various imines
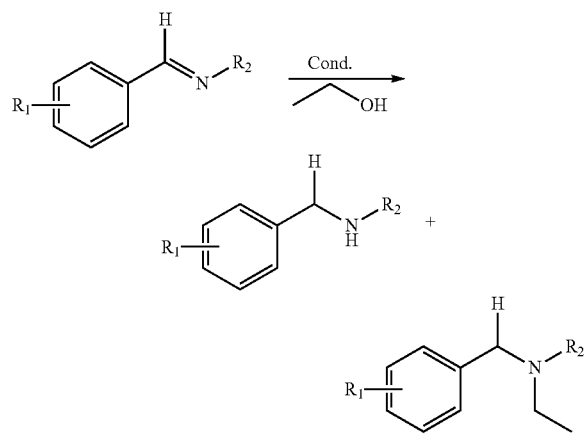
| Product | Catalyst | Ratio GC (starting/reduction/akylation/dialkylation) | Alkylation yield [%] |
|---|---|---|---|
| 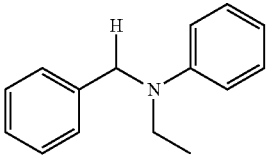 [SMILES: CCN(Cc1ccccc1)c1ccccc1] | A<br>B | —<br>23/42/35/0 | —<br>30 |
| 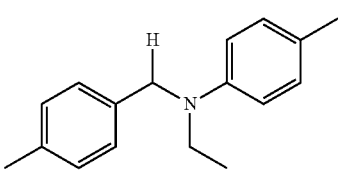 | A<br>B | —<br>0/4/96/0 | —<br>78 |
| 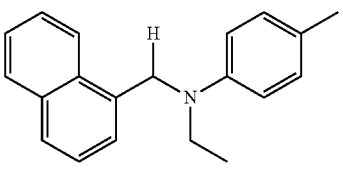 [SMILES: CCN(Cc1cccc2ccccc12)c1ccc(C)cc1] | A<br>B | —<br>0/47/35/18 | —<br>35 |
| 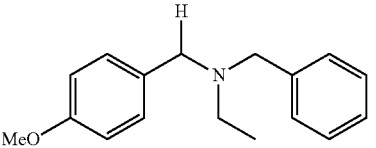 [SMILES: CCN(Cc1ccccc1)Cc1ccc(OC)cc1] | A<br>B | —<br>0/0/90/10 ou 0/0/83/17 | —<br>71 |

TABLE 12-continued

| Structure | Cond | Ratio GC | Yield [%] |
|---|---|---|---|
| 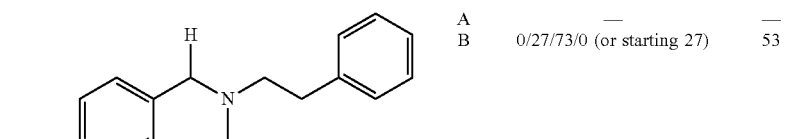 | A<br>B | —<br>0/27/73/0 (or starting 27) | —<br>53 |
| 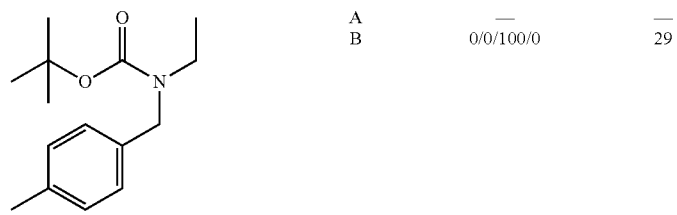 | A<br>B | —<br>0/0/100/0 | —<br>29 |
| 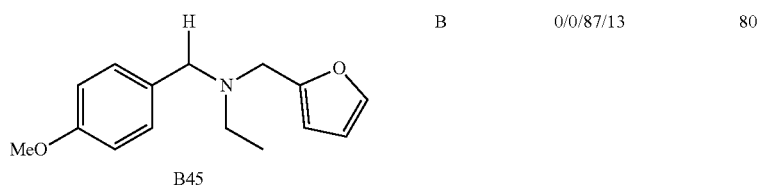<br>B45 | B | 0/0/87/13 | 80 |

Cond A: [Fe] (5 mol %), Me₃NO (5 mol %), EtOH 110° C.
Cond B: [Fe][MeCN] (5 mol %), EtOH 110° C.

Example 10: Intermolecular Version

TABLE 13

Optimization of the intermolecular version on the model substrates

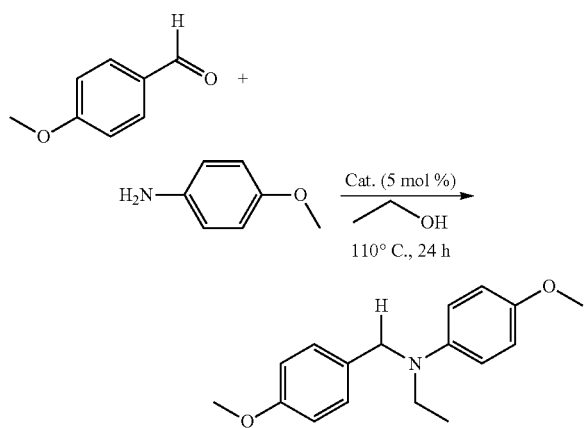

| Catalyst | Additive | Temperature [° C.] | Ratio GC (starting/reduction/akylation/dialkylation) | Yield [%] |
|---|---|---|---|---|
| B | — | 110 | 0/0/68/32 | 65 |

TABLE 4

Exemplification of the intermolecular version of the reaction

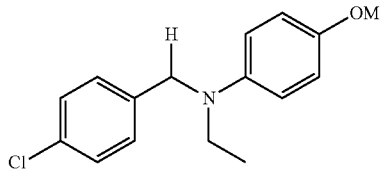

| Product | Ratio GC (starting/reduction/akylation/dialkylation) | Alkylation yield [%] |
|---|---|---|
| 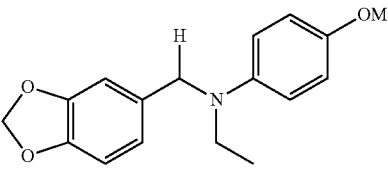 | 18/0/34/48/ ou 0/18/34/48 | 10 |
| 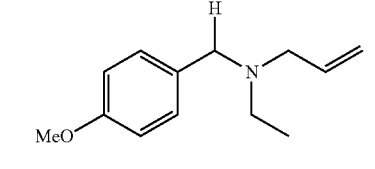 | 48/0/34/19 | 26 |
| 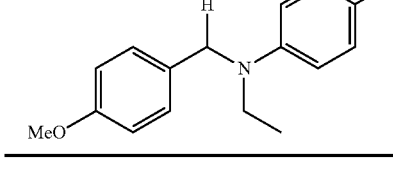 | 0/0/54/46 | 35 |
|  | 51/0/29/20 | 19 |

Alkylation Reactions of Imines (Conditions A)

In the glove box, catalyst A (0.05 eq.), trimethylamine oxide (0.05 eq.), previously distilled and degassed ethanol (0.05 M) were introduced into a tube equipped with a magnetic stirrer. The reaction mixture was stirred at room temperature for 30 minutes. The substrate (50 mg, 1 eq.) was then added, the tube was sealed with a Teflon plug and removed from the glovebox. Thereafter, the reaction tube is immersed in a bath preheated to 110° C. and stirred for 24 hours. After returning to ambient temperature, the reaction is stopped by adding methanol (1 ml) and sodium hydroxide (1 ml, 1 M). The organic phases are extracted with 3×5 ml of diethyl ether, washed with a saturated solution of sodium chloride (5 ml), then dried over magnesium sulfate and concentrated under reduced pressure. The crude product is purified by chromatography on silica gel column (12 g SiO$_2$ already treated with 5% triethylamine, cyclohexane/ethyl acetate, 95/5) to obtain the desired alkyl amine.

Alkylation Reactions of Imines (Conditions B)

In a catalyst tube (10 ml), equipped with a magnetic stirrer, the substrate (50 mg, 1 eq.), the catalyst B (0.05 eq.) and ethanol previously distilled and degassed (0.05 M) are introduced. The tube was placed under argon and then sealed with a Teflon stopper. Thereafter, the reaction tube is immersed in a bath preheated to 110° C. and stirred for 24 hours. After returning to ambient temperature, the reaction is stopped by adding methanol (1 ml) and sodium hydroxide (1 ml, 1 M). The organic phases were extracted with 3×5 ml of diethyl ether, washed with a saturated solution of sodium chloride (5 ml), then dried over magnesium sulfate and

The invention claimed is:

1. A method of preparation of unsymmetrical tertiary amines comprising using an alcohol and an imine as reactants, wherein the alcohol is a primary or secondary alcohol of formula (C)

$$R_4OH \quad (C)$$

wherein $R_4$ represents a $C_2$ to $C_{10}$ alkyl, or a $C_3$ to $C_{10}$ cycloalkyl, and wherein the imine is an imine of formula (D)

(D)

wherein $R_1$ and $R_2$ represent a hydrogen, aryl, allyl, $C_1$ to $C_{10}$ alkyl, or $C_3$ to $C_{10}$ cycloalkyl, $R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, wherein the tertiary amines are of formula (E)

(E)

wherein $R_1$, $R_2$, $R_3$ and $R_4$ are as defined above, wherein the tertiary amines carry three different substituents, said method comprising a step of alkylation of an alcohol of formula (C)

$$R_4OH \quad (C)$$

on an imine of formula (D)

(D)

to obtain the compound of formula (E)

wherein the step of alkylation is catalyzed by an iron(0) complex.

2. The method according to claim 1, wherein the iron(0) complex is chosen from the following formulas:

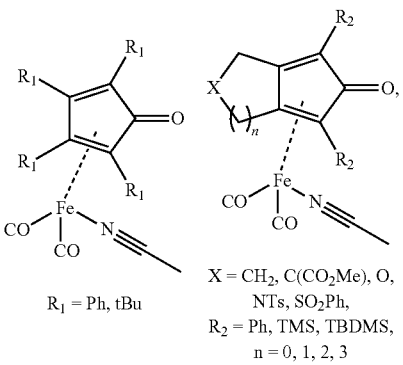

$R_1$ = Ph, tBu $X = CH_2, C(CO_2Me), O,$
$NTs, SO_2Ph,$
$R_2$ = Ph, TMS, TBDMS,
$n = 0, 1, 2, 3$ wherein Ts=tosyl

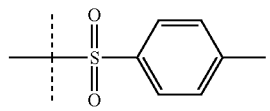

TMS=trimethylsilyl

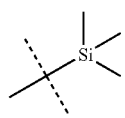

TBDMS=tert-butyldimethylsilyl

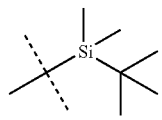

TIPS=triisopropylsilyl

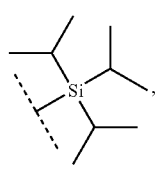, or the following formula (B):

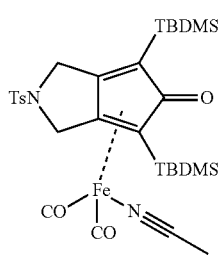
(B)

in which

TBDMS=tert-butyldimethylsilyl

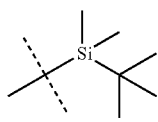

Ts=tosyl

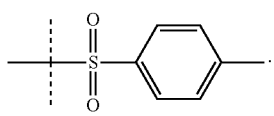

3. The method according to claim 1, wherein the step of alkylation is catalyzed either by the complex of formula (B) formed prior to the preparation of tertiary amines,

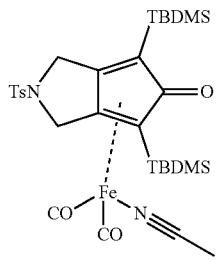
(B)

in which

TBDMS=tert-butyldimethylsilyl

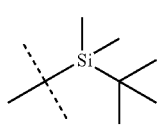

Ts=tosyl

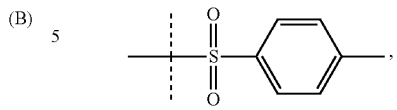

or by the catalyst formed in situ during said preparation of tertiary amines by adding trimethylamine oxide to the complex of formula (A)

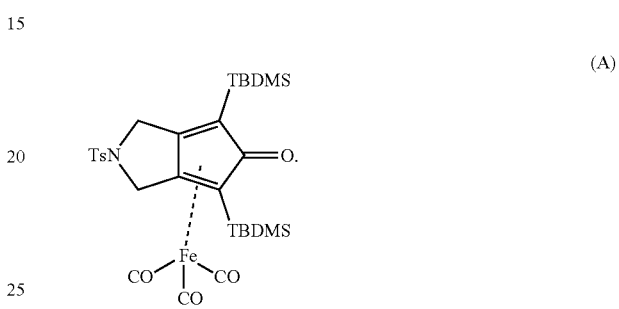
(A)

4. The method according to claim 1, wherein the step of alkylation is performed in an organic solvent, or in ethanol, or ethylene glycol, or in a mixture of solvents, or in a mixture of solvents composed of THF and of ethanol or of ethylene glycol.

5. The method according to claim 1, wherein the primary alcohol of formula (C), is also used as solvent for the step of alkylation.

6. The method according to claim 1, wherein the primary alcohol of formula (C), is also used as solvent for the step of alkylation, in a number of equivalents higher than 10 equivalents.

7. The method according to claim 1, wherein the imine of formula (D) is either formed prior to the preparation of the tertiary amines, or is formed in situ during said preparation of tertiary amines by a method comprising contacting an aldehyde or ketone of formula (F)

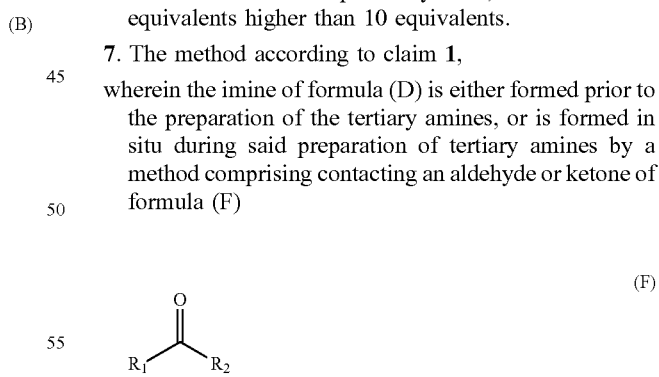
(F)

wherein $R_1$, $R_2$ represents a hydrogen, aryl, allyl, $C_1$ to $C_{10}$ alkyl, or $C_3$ to $C_{10}$ cycloalkyl, and an amine of formula (G)

$$R_3—NH_2 \quad (G)$$

wherein $R_3$ represents an aryl, allyl, $C_1$ to $C_{10}$ alkyl, $C_3$ to $C_{10}$ cycloalkyl, a $C_1$ to $C_{10}$ carbonyl derivative or a $C_3$ to $C_{10}$ formate.

8. The method according to claim 1,
wherein the step of alkylation is performed in the presence of a catalyst of formula (B)

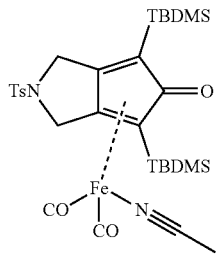
(B)

to obtain the compound of formula (E) as defined above,
or
comprising a first step of preparing of the catalyst
comprising a step of adding trimethylamine oxide on the complex of formula (A)

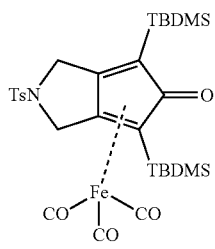
(A)

and a second step of alkylation of an alcohol of formula (C)

$R_4OH$     (C)

wherein $R_4$ represents a $C_2$ to $C_{10}$ alkyl, or a $C_3$ to $C_{10}$ cycloalkyl,
on an imine of formula (D)

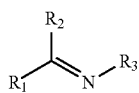
(D)

wherein $R_1$ and $R_2$ represent a hydrogen, aryl, allyl, $C_1$ to $C_{10}$ alkyl or a $C_3$ to $C_{10}$ cycloalkyl,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
in the presence of a catalyst of formula (B) prepared during the preceding step and as defined above,
to obtain the compound of formula (E)

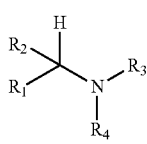
(E)

wherein $R_1$, $R_2$, $R_3$ and $R_4$ are as defined above,
or
comprising a first step of preparing imines of formula (D)

(D)

wherein $R_1$ and $R_2$ represent a hydrogen, aryl, allyl, $C_1$ to $C_{10}$ alkyl, or cycloalkyl $C_3$ to $C_{10}$,
$R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate,
comprising a step of contacting with an aldehyde or a ketone of formula (F)

(F)

wherein $R_1$ and $R_2$ are as defined above,
and an amine of formula (G)

$R_3$—$NH_2$     (G)

wherein $R_3$ is as defined above,
to obtain the imine of formula (D) as defined above;
and a second step of alkylation of an alcohol of formula (C)

$R_4OH$     (C)

wherein $R_4$ represents a $C_2$ to $C_{10}$ alkyl, or a $C_3$ to $C_{10}$ cycloalkyl,
on an imine of formula (D) prepared in the preceding step and as defined above, in the presence of a catalyst of formula (B)

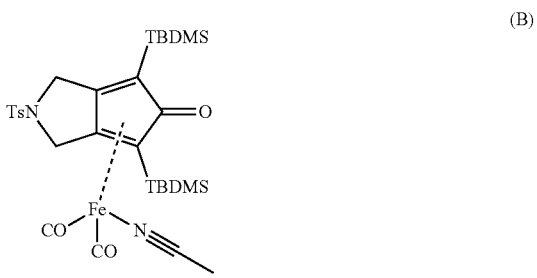
(B)

to obtain the compound of formula (E)

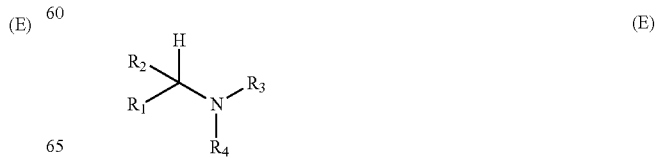
(E)

wherein $R_1$, $R_2$, $R_3$ and $R_4$ are as defined above,
or
comprising a prior step of preparing of imines of formula (D)

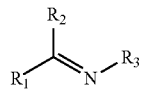
(D)

wherein $R_1$ and $R_2$ represent a hydrogen, aryl, allyl, $C_1$ to $C_{10}$ alkyl, or $C_3$ to $C_{10}$ cycloalkyl, $R_3$ represents an aryl, allyl, $C_1$ to $C_{10}$ alkyl, $C_3$ to $C_{10}$ cycloalkyl, a $C_1$ to $C_{10}$ carbonyl derivative, or a $C_3$ to $C_{10}$ formate, comprising a step of contacting an aldehyde or ketone of formula (F)

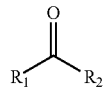
(F)

wherein $R_1$ and $R_2$ are as defined above,
and an amine of formula (G)

(G)

wherein $R_3$ is as defined above,
to obtain the imine of formula (D) as defined above;
a prior step of preparing the catalyst
comprising a step of adding trimethylamine oxide to the complex of formula (A):

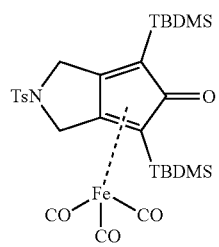
(A)

said two prior steps may occur in any order,
and a step of alkylation of an alcohol of formula (C)

(C)

wherein $R_4$ represents a $C_2$ to $C_{10}$ alkyl, or a $C_3$ to $C_{10}$ cycloalkyl,
on an imine of formula (D) prepared in the previous step

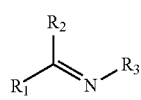
(D)

wherein $R_1$, $R_2$ and $R_3$ are as defined above,
in the presence of catalyst of formula (B) prepared in the preceding step and as above,
to obtain the compound of formula (E)

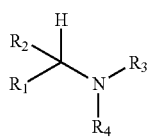
(E)

wherein $R_1$, $R_2$, $R_3$ and $R_4$ are as defined above.

9. The tertiary amines having one of the following formulae:

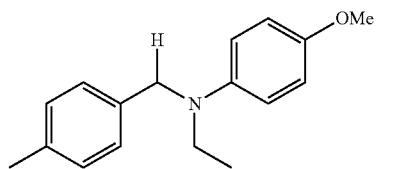

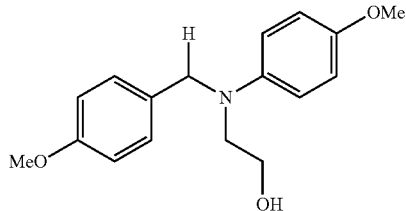

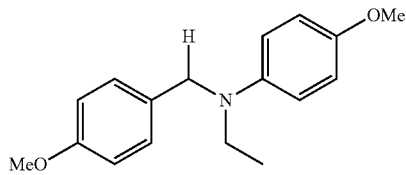

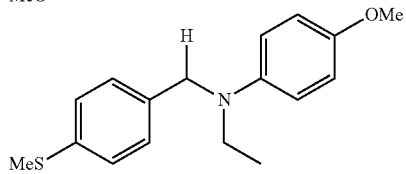

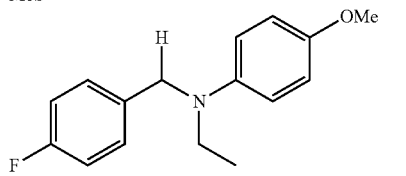

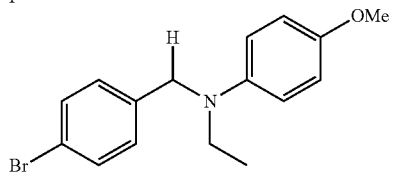

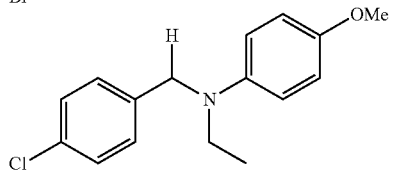

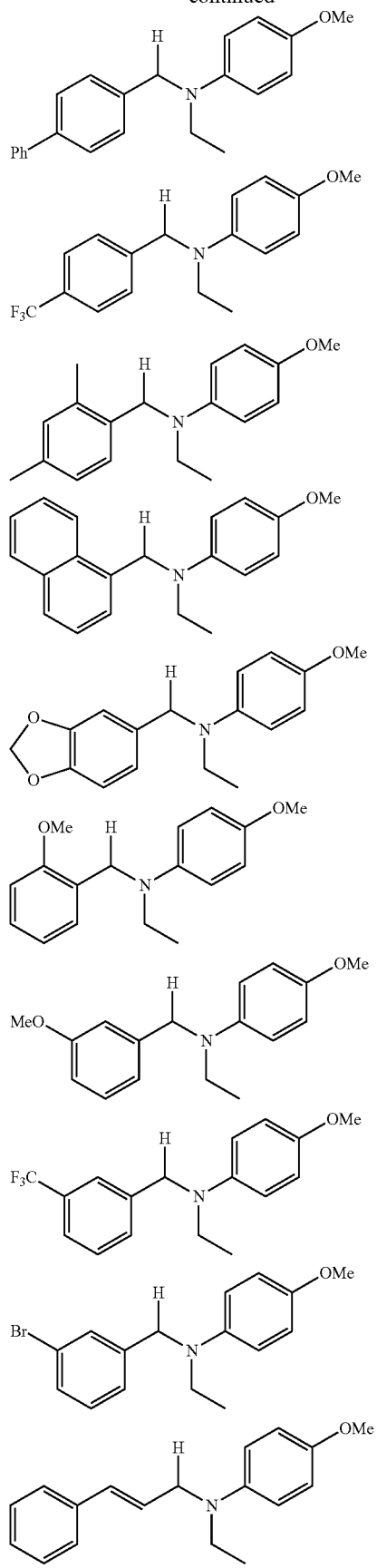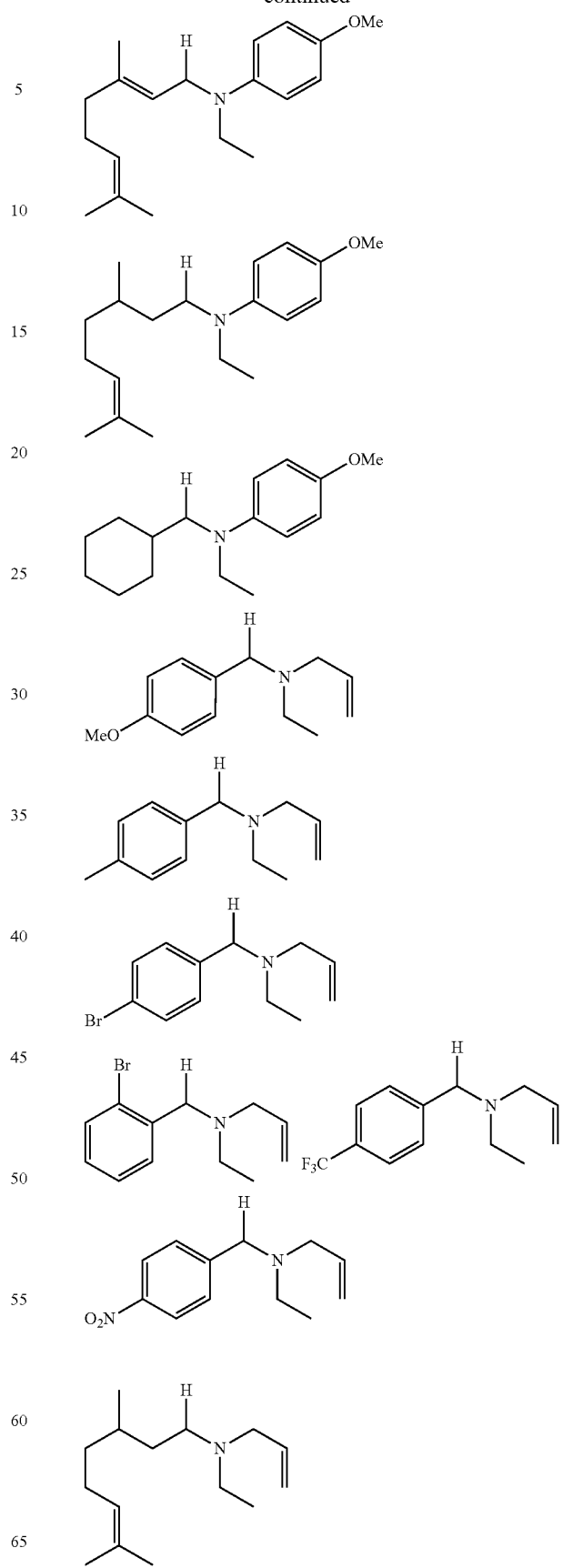

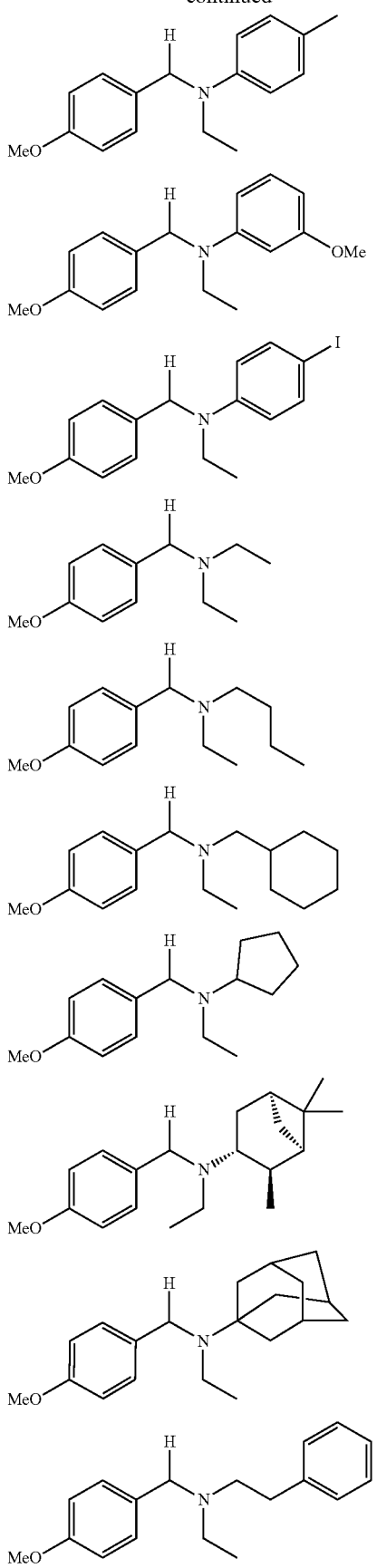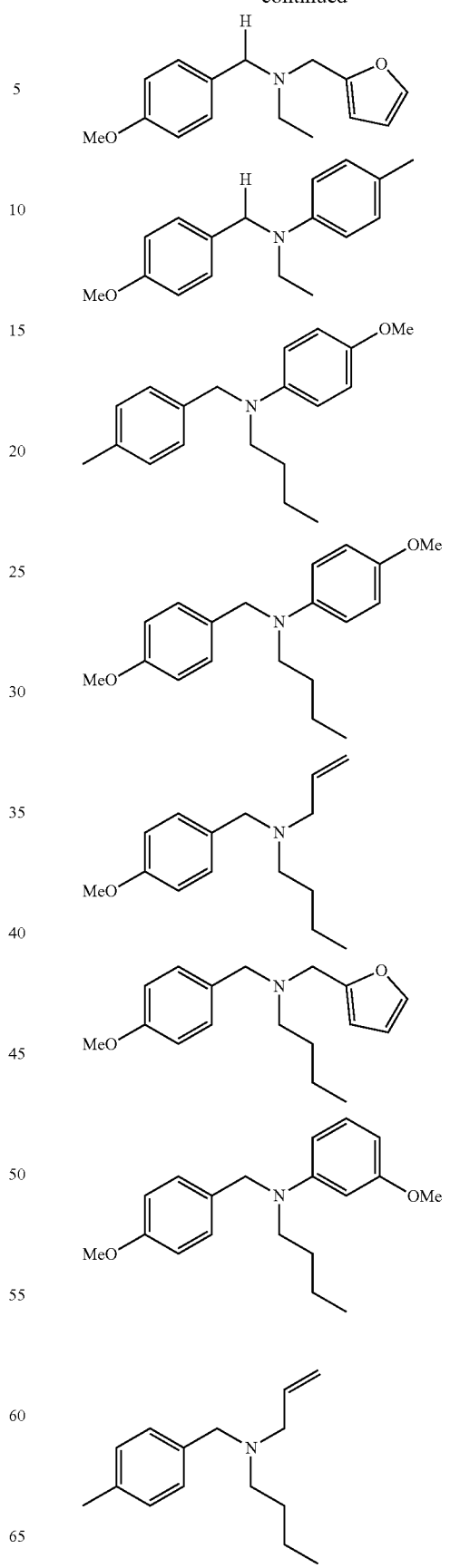

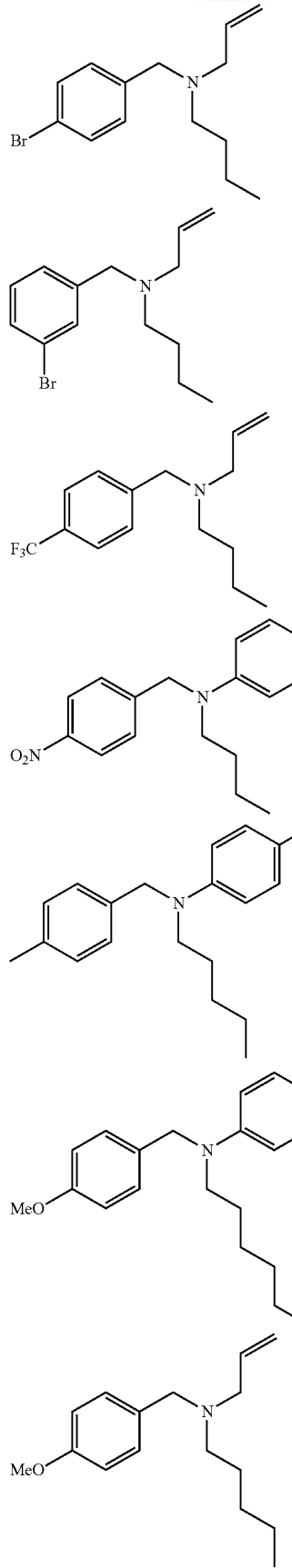
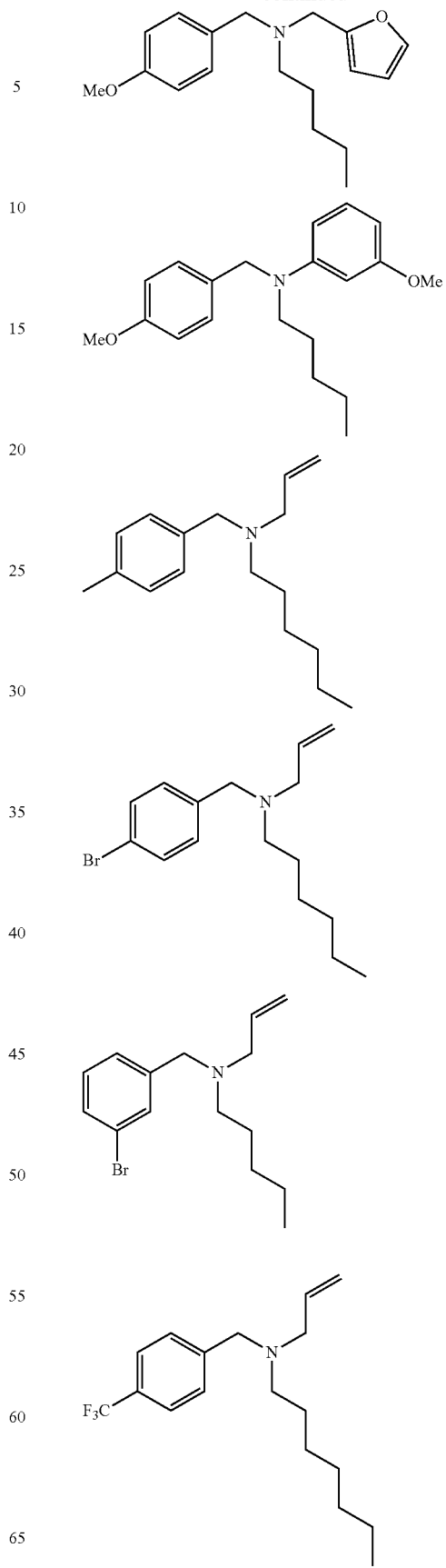

169
-continued
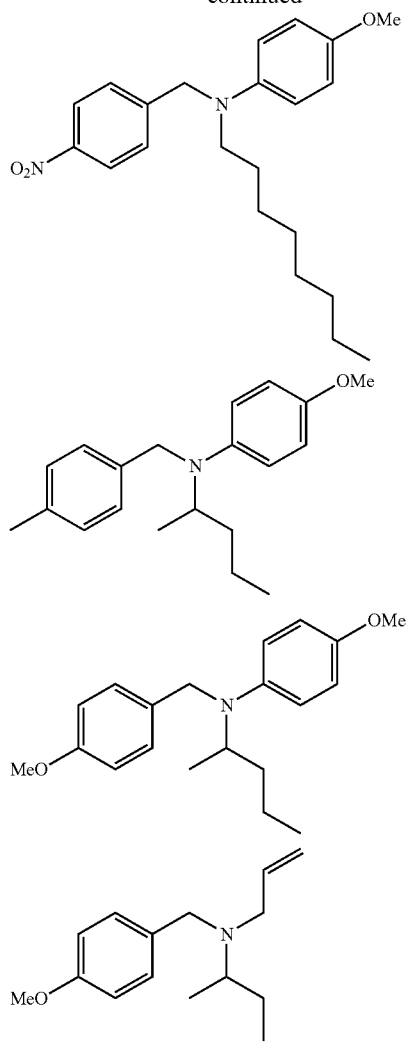
170
-continued
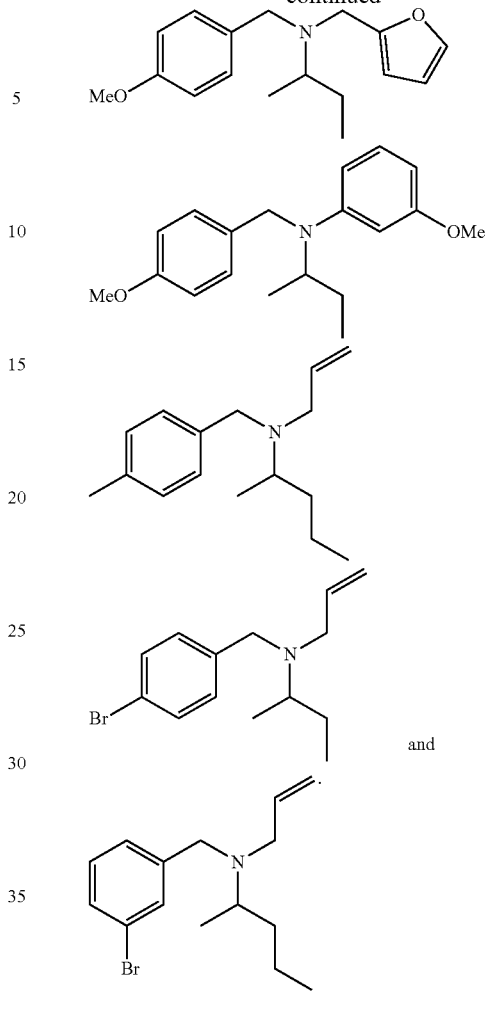
and
* * * * *